(12) United States Patent
Green et al.

(10) Patent No.: US 10,406,174 B2
(45) Date of Patent: *Sep. 10, 2019

(54) METHODS AND COMPOSITIONS FOR WOUND HEALING

(71) Applicant: OCUNEXUS THERAPEUTICS, INC., San Diego, CA (US)

(72) Inventors: Colin R. Green, Epsom (NZ); Bradford J. Duft, Rancho Santa Fe, CA (US); David L. Becker, Boxmoor (GB)

(73) Assignee: OCUNEXUS THERAPEUTICS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/284,389

(22) Filed: Oct. 3, 2016

(65) Prior Publication Data

US 2017/0296571 A1  Oct. 19, 2017

Related U.S. Application Data

(63) Continuation of application No. 13/590,113, filed on Aug. 20, 2012, now Pat. No. 9,457,044, which is a continuation of application No. 11/985,717, filed on Nov. 15, 2007, now Pat. No. 8,247,384.

(60) Provisional application No. 60/859,437, filed on Nov. 15, 2006.

(51) Int. Cl.
| | | |
|---|---|---|
| *A61K 31/711* | (2006.01) | |
| *A61K 35/33* | (2015.01) | |
| *C12N 15/113* | (2010.01) | |
| *A61K 38/17* | (2006.01) | |
| *A61K 38/18* | (2006.01) | |
| *A61K 35/36* | (2015.01) | |
| *A61K 45/06* | (2006.01) | |

(52) U.S. Cl.
CPC ............ *A61K 31/711* (2013.01); *A61K 35/33* (2013.01); *A61K 35/36* (2013.01); *A61K 38/1754* (2013.01); *A61K 38/1825* (2013.01); *A61K 38/1841* (2013.01); *A61K 38/1858* (2013.01); *A61K 45/06* (2013.01); *C12N 15/1138* (2013.01); *C12N 2310/11* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,861,757 A | 8/1989 | Antoniades et al. |
| 5,034,506 A | 7/1991 | Summerton et al. |
| 5,044,810 A | 9/1991 | Matsuoka et al. |
| 5,166,195 A | 11/1992 | Ecker |
| 6,319,907 B1 | 11/2001 | Ferguson |
| 6,331,298 B1 | 12/2001 | Ferguson |
| 6,387,364 B1 | 5/2002 | Ferguson |
| 6,455,569 B1 | 9/2002 | Ferguson |
| 6,506,559 B1 | 1/2003 | Fire et al. |
| 6,566,339 B1 | 5/2003 | Ferguson et al. |
| 6,696,433 B2 | 2/2004 | Ferguson et al. |
| 6,752,987 B1 | 6/2004 | Hammond et al. |
| 6,855,505 B2 | 2/2005 | Ferguson et al. |
| 6,900,181 B2 | 5/2005 | Ferguson et al. |
| 6,903,078 B1 | 6/2005 | Williams |
| 7,052,684 B2 | 5/2006 | Ferguson |
| 7,098,190 B1 | 8/2006 | Becker et al. |
| 7,153,822 B2 | 12/2006 | Jensen et al. |
| 7,250,397 B2 | 7/2007 | Gourdie et al. |
| 2003/0148968 A1 | 8/2003 | Hammond et al. |
| 2003/0215424 A1 | 11/2003 | Seul |
| 2004/0259768 A1 | 12/2004 | Lauermann |
| 2005/0026836 A1 | 2/2005 | Dack et al. |
| 2005/0119211 A1 | 6/2005 | Chowrira et al. |
| 2007/0021704 A1 | 1/2007 | Hariri et al. |
| 2007/0254828 A1 | 11/2007 | Dubreucq et al. |
| 2008/0159979 A1 | 7/2008 | Moore et al. |

FOREIGN PATENT DOCUMENTS

| | | |
|---|---|---|
| EP | 1100529 B1 | 6/2005 |
| JP | H11-502853 | 3/1999 |
| JP | 2002-529421 | 9/2002 |
| JP | 2002-535377 | 10/2002 |
| JP | 2003-529567 | 10/2003 |
| JP | 2005-509621 | 4/2005 |
| WO | WO-94/12633 | 6/1994 |
| WO | WO-98/24797 | 6/1998 |
| WO | WO-00/44409 | 8/2000 |
| WO | WO-02/056910 A1 | 7/2002 |
| WO | WO-03/032964 A2 | 4/2003 |
| WO | WO-2005/119211 A1 | 12/2005 |
| WO | WO-2006/032847 A1 | 3/2006 |
| WO | WO-2005/053600 A2 | 6/2006 |
| WO | WO-2006/069181 A2 | 6/2006 |

(Continued)

OTHER PUBLICATIONS

Agrawal, ed., "Antisense Oligonucleotides, toward clinical trials," *Protocols and Analogs, Synthesis and Properties*, 1993, Human Press Inc, New Jersey.
Aguayo et al., *J. Exp. Biol.*, 1981, 95:231-240.
Ahmadi et al., *Into. Opththalmol. Clinics*, 2002, 42(3):13-22.

(Continued)

*Primary Examiner* — Sean McGarry

(74) *Attorney, Agent, or Firm* — Duane Morris LLP

(57) ABSTRACT

Methods and compositions comprising combinations of one or more anti-connexin agents and one or more other agents useful for the promotion and/or improvement of wound healing and/or tissue repair.

18 Claims, 19 Drawing Sheets

Specification includes a Sequence Listing.

(56) References Cited

FOREIGN PATENT DOCUMENTS

| WO | WO-2006/134494 A2 | 12/2006 |
|---|---|---|
| WO | WO-2008/073479 A2 | 6/2008 |

OTHER PUBLICATIONS

Altschul, *J. Mol. Biol.*, 1990, 214:403-410.
Altschul, *J. Mol. Evol.*, 1993, 36:290-300.
Arnold et al., *Seminars in Ophthalmology*, 2002, 17:39-46.
Ashcroft et al., *Nat. Cell Biol.*, 1999, 1:260-266.
Ausubel et al., *Current Protocols in Molecular Biology*, 1987 (including supplements through 2001).
Baker et al., "ACC/AHA Guidelines for the Evaluation and Management of Chronic Heart Failure in the Adult," 2001, American College of Cardiology and the American Heart Association.
Baldwin et al., "Growth factors in corneal wound healing following refractive surgery: A Review," *ACTA Ophthalmologica Scandinavica*, Jun. 2002, 80(3):2002-2006.
Barany et al., *The Peptides*, Gross et al., eds., vol. 2, 1980, Academic Press, pp. 3-285.
BBC News, "Gels 'heal wounds more quickly,'" May 26, 2006, accessed online at http://news.bbc.co.uk/1/hi/health/3243633.stm.
Beaucage et al., eds., *Current Protocols in Nucleic Acid Chemistry*, 2000, John Wiley & Sons, Inc., New York.
Becker et al., "Gap junction-mediated interactions between cells," Chapter 3 from *Cell-Cell Interactions—A Practical Approach*, Fleming, ed., 2001, Oxford University Press, pp. 47-70.
Becker et al., "The role of gap junctions in the development of the preimplantation mouse embryo," in *Microscopy of Intercellular Communicating Junctions*, Gourdie, ed., 1995, *Microsc. Res. Tech.*, 31:364-374.
Becker et al., "Connexin alpha1 and cell proliferation in the developing chick retina," *Expl. Neurol.*, 1999, 156(2):326-332.
Becker et al., "Roles for α1 connexin in morphogenesis of chick embryos revealed using a novel antisense approach," *Devel. Genetics*, 24:33-42.
Becker et al., "Connexin expression in homotypic and heterotypic cell coupling in the developing cerebral cortex," *J. Compo. Neurol.*, 2002, 443:201-212.
Becker et al., "Cell coupling in the retina: Patterns and purpose," *Cell Biol. Int.*, 1998, 22:781-792.
Becker et al., "Changing patterns of ganglion cell coupling and connexin expression during chick retinal development," *J. Neurobiol.*, 2002, 52:280-293.
Becker et al., "Use of pIRES vectors to express EGFP and connexin constructs in studies of the role of gap junctional communication in the early development of the chick retina and brain," *Cell Commun. Adhes.*, 2002, 8:355-359.
Becker et al., "Expression of major gap junction connexin types in the working myocardium of eight chordates," *Cell Biol. Int.*, 1993, 22:527-543.
Becker et al., "The relationship of gap junctions and compaction in the preimplantation mouse embryo," *Development Suppl.*, 1992, 113-118.
Becker et al., "Functional analysis of amino acid sequences in connexin 43 involved in intercellular communication through gap junctions," *J. Cell Sci.*, 1995, 108:1455-1467.
Becker et al., "Functional block of gap junctional communication using antipeptide antibodies: Molecular localization of the putative binding sites," from *Intercellular communication through gap junctions*, Kanno, ed., *Progress in Cell Research*, 1995, 4:427-430.
Becker et al., "Pluronic gel as a means of antisense delivery," from *Antisense techniques in the CNS: A practical approach*, Leslie et al., eds., 1999, pp. 149-157.
Becker/Cook Lab, "Welcome to the lab of David Becker and Jeremy Cook," accessed online May 26, 2006 at http://www.anat.ucl.ac.uk/research/becker/people.htm.
Beeley, *Trends Biotechnol.*, Jun. 1994, 12(6):213-216.
Bennett et al., "Electrical coupling and neuronal synchronization in the Mammalian brain," *Neuron.*, Feb. 19, 2004, 41(4):495-511.
Berge et al., *J. of Pharma. Sci.*, 1977, 66:1-19.
Berkovitz et al., "The detailed morphology and distribution of gap junction protein associate with cells from the intra-articular disc of the rat temporomandibular joint," *Conn. Tiss. Res.*, 2003, 44:12-18.
Bernstein et al., *Invest. Ophthalmol. Vis. Sci.*, 2003, 44:4153-4162.
Berthoud et al., *Am. J. Physiol. Lung Cell Mol. Physiol.*, 2000, 279:L619-L622.
Blackburn et al., "Connexin43 gap junction levels during development of the thoracic aorta are temporally correlated with elastic laminae deposition and increased blood pressure," *Cell Biol. Int.*, Feb. 1997, PMID: 9080656 [PubMed—indexed for Medline], 21(2):87-97.
Blackburn et al., "Upregulation of connexin43 gap junctions during early stages of human coronary atherosclersis," *Arterioscler. Thromb. Vasc. Biol.*, Aug. 1995, PMID: 7627716 [PubMed—indexed for Medline], 15(8):1219-1228.
Boitano et al., *Am. J. Physiol. Lung Cell Mol. Physiol.*, 2000, 279:L623-L630.
Braasch et al., *Biochemistry*, 2002, 41:4503-4510.
Braet et al., "Pharmacological sensitivity of ATP release triggered by photoliberation of inositol-1,4,5-triphosphate and zero extracellular calcium in brain endothelial cells," *Journal of Cellular Physiology*, 2003, 197(2):205-213.
Branch, *Hepatology*, 1996, 24:1517-1529.
Brandner et al., "Connexins 26, 30, and 43: Differences Among Spontaneous, Chronic, and Accelerated Human Wound Healing," *J. Invest. Dermatol.*, 2004, 122:1310-1320.
Brummelkamp et al., *Science*, 2002, 296:550-553.
Brunton, Chapter 38 from *The Pharmacological Basis of Therapeutics*, 9$^{th}$ ed., Goodman et al., eds.
Brysch, *Antisense Technology in the Ventral Nervous System*, Robertson, ed., 1999, Oxford University Press, pp. 21-41.
Buono et al., *Survey of Ophthalmology*, 2005, 50:15-26.
Buur et al., *J. Control Rel.*, 1990, 14:43-51.
Cairns et al., *Nat. Biotech.*, 1999, 17:480-486.
Camelliti et al., "Spatially and temporally distinct expression of fibroblast connexins after sheep ventricular infarction," *Cardiovasc. Res.*, May 1, 2004, PMID: 15094361 [PubMed—indexed for Medline], 62(2):415-425.
Camelliti et al., "Structural and functional coupling of cardiac myocytes and fibroblasts," *Adv. Cardiol.*, 2006, PMID: 16646588 [PubMed—indexed for Medline], 42:132-149.
Canadian Paraplegic Association, "A Chinese procedure involving stem cell transplants is providing some very interesting results," Oct. 24, 2003, accessed, online Sep. 27, 2006 at http://www.canparaplegic.org/national/level12.tpi?var1=story&var2=20031024154627.
Caplen et al., *Proc. Natl. Acad. Sci.*, 2001, 98:9742-9747.
Care Cure Community Postings, "Gel is helping wounds heal in half the time/nexagon," Collaborative Neuroscience The Spinal Cord Injury Project, accessed online Sep. 29, 2006 at http://scirutgers.edu/forum/showthread.php?t=6653.
Cech, "Group I Introns: New Molecular Mechanisms for MRNA repair," *Biotechnology*, 1995, 13:323.
Chakraborti et al., *Mol. Ther.*, 2003, 7:817-826.
Chanson et al., "Gap junctional communication in tissue inflammation and repair," Biochim. Biophys. Acta., 2005, 1711(2):197-207.
Cheng et al., *J. Biol. Chem.*, Oct. 15, 1998, 263(29):15110-15117.
Cheng et al., *Science*, 273:510-513.
Chonn et al., *Current Op. Biotech.*, 1995, 6:698-708.
Chou et al., *Ad. Enzyme Res.*, 1984, 22:27-55.
Chunmao et al., "Optimal time for the administration of rhGH in severely burned patients—analysis of the dynamic changes in IGF axis and blood sugar," *Chin. J. Burns*, Aug. 31, 2003, 19(4):213-215.
Coffey et al., "Molecular profiling and cellular localization of connexin isoforms in the rat ciliary epithelium," *Exp. Eye Res.*, Jul. 2002, PMID: 12123633 [PubMed—indexed for Medline], 75(1):9-21.

(56) References Cited

OTHER PUBLICATIONS

Coligan et al., eds., *Current Protocols in Immunology*, vol. 1, Chapter 1.
Collignon et al., Ophthalmology, 2004, 111:1663-1672.
Common et al., "Functional studies of human skin disease- and deafness-associated Connexin 30 mutations," *Biochem. Biophys. Res. Commun.*, 298:651-656.
Cook et al., "Gap Junctions in the vertebrate retina," from *Microscopy of Intercellular Communication Junctions*, Gourdie, ed., 1995, *Microsc. Res. Tech.* 31:408-419.
Cotrina et al., "Astrocytic gap junctions remain open during eschemic conditions," *J. Neurosci.*, 18:2520-2537.
Courtman et al., *J. Biomed. Mater. Res.*, 1994, 28:655-666.
Coutinho et al., "Dynamic Changes in connexin expression correlate with key events in the wound healing process," *Cell Biology International*, 2003, 27:525-541.
Coutinho et al., "Limiting wound extension by transient inhibition of connexin43 expression at the site of injury," *Brit. J. Plast. Surg.*, 2005, 58:658-667.
Cronin et al., *Antisense delivery and protein knockdown within the intact central nervous system*.
Crooke et al.., eds., *Antisense Research and Applications*, Chapters 2, 19, 28, and 32, 1993, CRC Press.
Crooke et al., *J. Pharmacol. Exp. Ther.*, 277:923-937.
Crowe, M. et al., "Delayed Wound Healing in Immunodeficient TGF-β1 Knockout Mice", *J. Invest. Dermatol.*, 2000, 115:3-11.
Cutroneo, K., "How Is Type I Procollagen Synthesis Regulated at the Gene Level During Tissue Fibrosis", *J. Cell. Biochem.*, 2003, 90:1-5.
Dagle et al., *Nucleic Acids Research*, 1991, 19:1805.
Dahl et al., *Biophys. J.*, 1994, 67:1816-1822.
Davis et al., "Modulation of Connexin43 Expression: Effects On Cellular Coupling," *Journal of Cardiovascular Electrophysiology* (Futura Publishing Co.) , 1995, 6(2):103-114.
De Vriese et al., *Kidney Int.*, 2001, 61:177-185.
Devereux et al., *Nucleic Acids Research*, 1984, 12:387-395.
Devlin et al., "An ovine model of chronic stable heart failure," *J. Card. Fail.*, 2000, 6:140-143.
DeVries et al., "Hemi-gap-junction channels in solitary horizontal cells of the catfish retina," *Journal of Physiology*, 1992, 445:201-230.
Di et al., "Oestriol and oestradiol increase cell to cell communication and connexin 43 protein expression in cultured human myometrial cells," *Mol. Human Reprod.*, 2001, 7:671-679.
Dias et al., *Mol. Cancer Thor.*, 2002, 1347-1355.
Dietz et al., *Ophthalmology*, 1986, 93:1284.
Dovi et al., *J. Leukoc. Biol.*, 2003, 73:448-455.
Eckstein, ed., *Oligonucleotides and Analogues, A Practical Approach*, 1991, IRL Press at Oxfor University Press.
Edgington, *Biotechnology*, 1992, 10:256.
Einarson et al., "Identification of Protein-Protein Interactions with Glutathione S-Transferase Fusion Proteins," from *Protein-Protein Interactions: A Molecular Cloning Manual*, 2002, Cold Springs Harbor Laboratory Press, pp. 37-57.
Elbashir et al., "Duplexes of 21-nucleotide RNAs mediate RNA interference in cultured mammalian cells," *Nature*, 2001, 411:494-498.
El-Hariri et al., *J. Pharm. Pharmacol.*, 1992, 44:651-654.
Englisch et al., *Angewandte Chemie*, International Edition, 1991, 30:613-722.
Evans et al., *J. Med. Chem.*, 1987, 30:1229.
Evans et al., *Biochem. Soc. Trans.*, 2001, 29:606-612.
Fauchere, *J. Adv. Drug Res.*, 1986, 15:29.
Ferrin et al., *Science*, 1991, 354:1494.
Flower et al., "A new type of gap junction in the phylum Brachiopoda," *Cell Tissue Res.*, 1982, 227(1):231-234.
Fonseca et al., "Upregulation in astrocytic connexin 43 gap junction levels may exacerbate generalized seizures in mesial temporal lobe epilepsy," *Brain Res.*, Mar. 1, 2002, PMID: 11852037 [PubMed—indexed for Medline], 929(1):105-116.
Foote et al., *J. Cell Biol.*, 1998, 140(5):1187-1197.
Forge et al., "Gap junctions and connexin expression in the inner ear," from *Gap junction-mediated intercellular signalling in health and disease*, 1999, Novartis foundation symposium 219, Wiley, pp. 134-156.
Forge et al., "Distribution and connexin composition of gap junctions in the inner ear: Evidence for heteromeric Cx26/Cx30 connexons," *J. Compo. Neurol.*, 2003, 467:207-231.
Forge et al., "Connexins and gap junctions in the inner ear," *Audiol. Neuro. Otol.*, 2002, 7:141-145.
Forge et al., "The inner ear contains heteromeric channels composed of Cx26 and Cx30 and deafness-related mutations in Cx26 have a dominant negative effect on Cx30," *Cell Commun. Adhes.*, 2003, 10:341-346.
Fortes et al., *Proc. Natl. Acad. Sci. USA*, 2003, 100:8264-8269.
Foulkes et al., *Stroke*, 1988, 19:547-554.
Frantseva et al., "Ischemia-Induced Brain Damage Depends on Specific Gap-Junctional Coupling," *Journal of Cerebral Blood Flow and Metabolism*, 2002, 22:453-462.
Fraser et al., "Selective disruption of gap junctional communication interferes with a patterning process in hydra," *Science*, Jul. 3, 1987, PMID: 3037697 [PubMed—indexed for Medline], 237(4810):49-55.
Gait, ed., *Oligonucleotide Synthesis*, Chapter 1, 1984.
Galasso et al, *Seminars in Ophthalmology*, 2004, 19:75-77.
Garcia-Dorada et al., *Circulation*, 1997, 96:3579-3586.
Gee et al., *Molecular and Immunologic Approaches*, Huber et al., eds., 1994, Futura Publishing Co., Mt. Kisco, NY.
Gerrits et al., *Pediatr. Res.*, 2005, 57(3):342-346.
Giaume et al., "Control of gap junctional communication in astrocytic networks," *TINS*, 19:319-325.
Giepmans, *J. Biol. Chem.*, Mar. 16, 2001, 276(11):8544-8549.
Gil et al., "Induction of apoptosis by the dsRNA-dependent protein kinase (PKR): Mechanisms of action," *Apoptosis*, 2000, 5:107-114.
Goodenough, *J. Cell., Biol.*, 1988, 107:1817-1824.
Görbe et al., "In differentiating prefusion myoblasts connexin43 gap junction coupling is upregulated before myoblast alignment then reduced in postmitotic cells," *Histochem. Cell Biol.*, 2005, 123:573-583 [Epub May 14, 2005].
Görbe et al., "Transient upregulation of connexin 43 gap junction coupling in myoblasts may synchronize cell cycle control preceding syncytial fusion during skeletal muscle differentiation," *Histochem. Cell Biol.*, 2005, 123:573-583.
Gourdie et al., "Evidence for a distinct gap junctional phenotype in ventricular conduction tissues of the developing and mature avian heart," *Circ. Res.*, Feb. 1993, PMID: 8380357 [PubMed—indexed for Medline], 72(2):278-289.
Gourdie et al., "Immunolabelling patterns of gap junction connexins in the developing and mature rat heart," *Anat. Embryol. (Berl)*, 1992, PMID: 1319120 [PubMed—indexed for Medline], 185(4):363-378.
Gourdie et al., "Gap junction distribution in adult mammalian myocardium revealed by an anti-peptide antibody and laser scanning confocal microscopy," *J. Cell Sci.*, May 1991, PMID: 1661743 [PubMed—indexed for Medline], 99(1):41-55.
Gourdie et al., "Cardiac gap junctions in rat ventricle: localization using site-directed antibodies and laser scanning confocal microscopy," *Cardioscience*, Mar. 1990, PMID: 1966373 [PubMed—indexed for Medline], 1(1):75-82.
Gourdie et al., "The spatial distribution and relative abundance of gap-junctional connexin40 and connexin43 correlate to functional properties of components of the cardiac atrioventricular conduction system," *Journal of Cell Science*, 1993, 105:985-991.
Grazul-Bilska et al., *Biology Reproduction* (abstract), 1998, 58(1):78.
Green et al., "Spatiotemporal depletion of connexins using antisense oligonucleotides: Techniques in the study of gap junctions—Connexin methods and protocols," *Methods in Molecular Biology*, Bruzzone et al, eds., 2001, 154:175-185.
Green et al., "Expression of the connexin43 gap junctional protein in tissues at the tip of the chick limb bud is related to the epithelial-mesenchymal interactions that mediate morphogenesis," *Dev. Biol.*, Jan. 1994, PMID: 8293868 [PubMed—indexed for Medline], 161(1):12-21.

(56) References Cited

OTHER PUBLICATIONS

Green et al., "Analysis of the rat liver gap junction protein: clarification of anomalies in its molecular size," *Proc. R. Soc. Lond. B. Biol. Sci.*, Mar. 22, 1988, PMID: 2898146 [PubMed—indexed for Medline], 233(1271):165-174.
Green et al., "Validation of immunohistochemical quantification in confocal scanning laser microscopy: a comparative assessment of gap junction size with confocal and ultrastructural techniques," *J. Histochem. Cytochem.*, Sep. 1993, PMID: 2898146 [PubMed—indexed for Medline], 41(9):1339-1349.
Green et al., "Connexon rearrangement in cardiac gap junctions: evidence for cytoskeletal control?" *Cell Tissue Res.*, 1984, PMID: 6090023 [PubMed—indexed for Medline], 237(1):185-186.
Green et al., "Gap junction connexon configuration in rapidly frozen myocardium and isolated intercalated disks," *J. Cell Biol.*, Aug. 1984, 99(2):453-463.
Green et al., "Distribution and role of gap junctions in normal myocardium and human ischaemic heart disease," *Histochemistry*, Feb. 1993, 99(2):105-120.
Green, "Evidence mounts for the role of gap junctions during development," *Bioessays*, Jan. 1988, PMID:2835035 [PubMed—indexed for Medline], 8(1):7-10.
Grose, R. et al.., "Wound-Healing Studies in Transgenic and Knock-out Mice", *Molecular Biotechnology*, 2004, 28:147-166.
Guan et al., *Neuroscience*, 1999, 95(3):831-839.
Gunn et al., *J. Clin. Invest.*, 1997, 99(2):248-256.
Gunn et al., *Pediatr. Res.*, 1999; 46(3):274-280.
Haefliger et al., "*Homo sapiens* 43 (CX43) gene, complete cds," from "Sporadic cases of dilated cardiomyopathesis associated with atrioventricular conduction defects are not linked to mutation within the connexins 40 and 43 genes," *Eur. Heart J.*, 1999, 20(24):1843 (NCBI Genbank Accession No. AF151980, Dec. 19, 2000).
Hall, "Gel is helping wounds heal in half the time," *Telegraph UK*, Oct. 20, 2003, accessed online at http://www.telegraph.co.uk/news/main.jhtml?xml=/news/2003/10/20/nge120.xml&sSheet=. . . .
Hardman et al., 1996, McGraw-Hill, New York, pp. 934-935.
Hardy et al., "Cell death (Apoptosis) in human blastocysts," Chapter 9 from *An Atlas of Human Blastocysts*, Veeck et al., eds., 2003, CRC Press, pp. 185-202.
Hardy et al., "Expression of intercellular junctions during the preimplantation development of the human embryo," *Molec. Human Reprod.*, 1996, 2:621-632.
Harfst et al., "Cardiac myocyte gap junctions: evidence for a major connexon protein with an apparent relative molecular mass of 70,000," *J. Cell Sci.*, Aug. 1990, 96(4):591-604.
Harlow et al., *Antibodies, A Laboratory Manual*, 1988, Cold Spring Harbor Publication, New York.
Haseloff et al., *Nature*, Aug. 18, 1988, 334(6183):585-591.
Heasman, *J. Dev. Biol.*, 2002, 243:209-214.
Henikoff et al., *Proc. Natol. Acad. Sci. USA*, 1992, 89:10915-10919.
Hennemann et al., *Eur. J. Cell Biol.*, 58(1):81-89.
Hermanson, ed., *Bioconjugate Techniques*, Chapters 2 and 17, 1996, Academic Press.
Ho et al., *Journal of Neurosurgical Anesthesiology*, 2005, 17:38-44.
Hodgins, "Connecting Wounds with Connexins," *J. Invest. Dermatol.*, 2004, 122(5):ix-x.
Huang et al., *J. Cell Biol.*, 1998, 143:1725-1734.
Goliger et al., *Molecular Biology of the Cell*, 1995, 6:1491-1501.
Janes, "Speed healing," *Unlimited*, Dec. 1, 2004, Issue 67, accessed online on Sep. 29, 2006 at http://unlimited.co.nz/unlimited.nsf/ulfuture/250EA628CE599A70CC256F6B00046325.
Jen et al., *Stem Cells*, 2000, 18:307-319.
Jester et al., *Cornea*, 1992, 11:191.
Jiang-Depeng et al., "The expression of secretory leukocyte protease inhibitor in dermal pluripotent stem cells," *Chin. J. Crit. Care Med.*, May 31, 2006, 26(5):345-348.
Jyung, et al., "Increased wound-breaking strength induced by insulin-like growth factor I in combination with insulin-like growth factor binding protein-1", *Surgery*, 1994,115:233-239.
Kabanov et al., *FEBS Lett.*, 1990, 259:327-300.

Kandel et al., *Principles of Neural Science*, 4th Ed., 2000, McGraw-Hill, New York, pp. 178-180.
Karlin et al., *Proc. Natl. Acad. Sci. USA*, 1993, 90:5873-5787.
Keirstead et al., *Exp. Neurol.*, 1999, 159:225-236.
Khosla et al., *Journal of Postgraduate Medicine*, 2004, 50:219-221.
Kieber-Emmons et al., *Curr. Opin. Biotechnol.*, Aug. 1997, 8(4):435-441.
Kurpakus-Wheater et al., *Biotech. Histochem.*, 1999, 74:146-159.
Lampugnani, "Cell Migration into a wounded area in vitro," *Methods Mol. Biol.*, 96:177-182.
Laux-Fenton et al, "Connexin expression patterns in the rat cornea: molecular evidence for communication compartments," *Cornea*, Jul. 2003, PMID: 12827052 [PubMed—indexed for Medline], 22(5):457-464.
Law et al., "Knockdown of Connexin 43 mediated regulation of ZPA activity in the developing chick limb bud leads to digit truncation," *Dev. Growth Differ.*, 2002, 44:537-547.
Laxat, "Nice blurb on biologics on cbsnews.com," accessed online Sep. 9, 2006 at http://www.laxat.com/Nice-blurb-on-biologics-on-cbsnews-com-1219610.html.
Lee et al., *Critical Reviews in Therapeutic Drug Carrier Systems*, 1991, 8:91-192.
Lepisto, J. et al., "Platelet-Derived Growth Factor Isoforms PDGF-AA, -AB and -BB Exert Specific Effects on Collagen Gene Expression and Mitotic Activity of Cultured Human Wound Fibroblasts", *Biochem. Biophys. Res. Comm.*, 1995, 209(2):393-399.
Letsinger et al., *Proc. Natl. Acad. Sci. USA*, 1989, 86:6553-6556.
Leybeart et al., *Cell Commun. Adhes.*, 2003, 10:251-257.
Li et al., *Dev.*, 2002, 129:2031-2042.
Li et al., "Properties and regulation of gap junctional hemichannels in the plasma membranes of cultured cells," *Journal of Cell Biology*, 1996, 134(4):1019-1030.
Lin et al., "Gap-Junction-mediated propagation and amplification of cell injury," *Nature Neurosci.*, 1998, 1:431-432.
Makarenkova et al., "Fibroblast growth factor 4 directs gap junction expression in the mesenchyme of the vertebrate limb bud," *J. Cell Biol.*, 1997, 138:1-13.
Malone et al., *J. Vasc. Surg.*, 1984, 1:181-191.
Manoharan et al., *Nucleosides & Nucleotides*, 1995, 14(3-5):969-973.
Manoharan et al., *Bioorg. Med. Chem. Lett.*, 1993, 3(12):2765-2770.
Manoharan et al., *Bioorg. Med. Chem. Lett.*, 1994, 4:1053-1060.
Manoharan et al., *Tetrahedron Lett.*, 1995, 36(21):3651-3654.
Martin et al., *Helv. Chim. Acta*, 1995, 78:486-504.
Martin, *Science*, 1997, 276:75-81.
Martin et al., *Curr. Biol.*, 2003, 13:1122-1128.
Martin, P. et al., "Inflammatory cells during wound repair: the good, the bad and the ugly", *Trends in Cell Biology*, Nov. 2005, 15(11):599-607/.
Marx, "Interfering with Gene Expression," *Science*, 2000, 288:1370-1372.
Marziano et al., "Deafness-related mutations in gap junction protein connexin 26 have a dominant negative effect on connexin 30," *Human Molecular Genetics*, 2003, 203:805-812.
Masseyeff et al., eds., *Methods of Immunological Analysis*, vol. I, Chapters 1-4 and vol. III, Chapter 4, 1993, VCH Verlags gesellschaft mbH, Weinheim.
McDonald et al., *Scientific American*, Sep. 1999, 55-63.
McDonnel et al., *Arch. Ophthalmol.*, 1988, 106:212.
McGonnell et al., "Communication through connexin 43 gap junction channels contributes to the normal development of the embryonic face," *Dev. Dynam.*, 2001, 222:420-438.
Meienhofer, *Hormonal Proteins and Peptides*, vol. 2, Li, ed., 1973, Academic Press, pp. 48-267.
Melton, ed., *Antisense RNA and DNA*, 1988, Cold Spring Harbor Laboratory, Cold Spring Harbor, NY.
Merrifield, *J. Am. Chem. Soc.*, 1963, 85:2149.
Meyer, *J. Cell. Biol.*, 1992, 119:179-189.
Miller et al., eds., *Gene Transfer Vectors for Mammalian Cells, Introduction*, 1987.
Mishra et al., *Biochim. Biophys. Acta*, 1995, 1264:229-237.
Moore et al., *Am. J. Physiology*, Nov. 1, 1994, 267(5):C1371-1388.

(56) References Cited

OTHER PUBLICATIONS

Mori et al., "Impairment of skin wound healing in beta-1,4-galactosyltransferase-deficient mice with reduced leukocyte recruitment," *Am. J. Pathol.*, 164:1303-1314.

Morrisey et al., *J. Neuroscience*, 1991, 11:2433-2442.

Mullis et al., eds., *PCR: The Polymerase Chain Reaction*, Chapters 1-19, 1994.

Muranishi, *Critical Review in Therapeutic Drug Carrier Systems*, 1990, 7:1-33.

Mustoe et al., *Science*, 1987, 237:1333-1336.

Nadarajah et al., "Basic FGF increases communication between cells of the developing neocortex," *J. Neurosci.*, 1998, 18:7881-7890.

Neckers et al., "Anti-sense technology: biological utility and practical considerations," *Am. J. Physiol.*, 265:L1-L12.

Nickel et al., "Molecular and functional characterization of gap junctions in the avian inner ear," *J. Neurosci.*, Jun. 7, 2006, 26(23):6190-6199.

Nielsen et al., *Science*, 1991, 254:1497.

Oberhauser et al., *Nucl. Acids Res.*, 1992, 20:533-538.

Oviedo-Orta et al., "Gap Junctions and Connexin-Mediated Communication in the Immune System," *Biochimica et Biophysica Acta. Biomembranes (Amsterdam, NL)*, Mar. 23, 2004, 1662(1-2):102-112.

Oviedo-Orta, E. et al., "Immunoglobulin and cytokine expression in mixed lymphocyte cultures is reduced by disruption of gap junction intercellular communication", *FASBB J.*, May 2017, 15(3):768-774.

Oviedo-Orta, E. et al., "Intercellular communication in the immune system: differential expression of connexin40 and 43, and perturbation of gap junction channel functionsin peripheral blood and tonsil human lymphocyte subpopulations", *Immunology*, 2000, 99:578-590.

Paddison et al., "Short hairpin RNAs (shRNAs) induce sequence-specific silencing in mammalian cells," *Genes & Dev.*, 2002, 16:948-958.

Paddison et al., "Stable suppression of gene expression by RNAi in mammalian cells," *Proc. Natl. Acad. Sci. USA*, 2002, 99:1443-1448.

Parker et al., *Nucleic Acids Res.*, 1991, 19:3055-3060.

Pearson et al., Gap junctions modulate interkinetic nuclear migration in retinal progenitor cells, 2005, *J. Neurosci.*, 25:10803-10814.

Penn et al., *Autoimmunity Reviews*, 2003, 2:199-203.

Pepose et al., "The cornea," from *Adler's Physiology of the eye: Clinical application*, 9$^{th}$ Ed., 1992, Mosby Year Book, St. Louis, pp. 29-47.

Peters et al., "Cardiac arrhythmogenesis and the gap juncation," *J. Mol. Cell Cardiol.*, Jan. 1995, PMID: 7760358 [PubMed—indexed for Medline], 27(1):37-44.

Peters et al., "Reduced content of connexin43 gap junctions in ventricular myocardium from hypertrophied and ischemic human hearts," *Circulation*, Sep. 1993, PMID: 8394786 [PubMed—indexed for Medline], 88(3):864-875.

Peters et al., "The Wolff-Parkinson-White syndrome: the cellular substrate for conduction in the accessory atrioventricular pathway," *Eur. Heart J.*, Jul. 1994, PMID: 7925521 [PubMed—indexed for Medline], 15(7):981-987.

Peters et al., "Spatiotemporal relation between gap junctions and fascia adherens junctions during postnatal development of human ventricular myocardium," *Circulation*, Aug. 1994, PMID: 8044940 [PubMed—indexed for Medline], 90(2):713-725.

Peters et al., *EMBO J.*, 2005, 24:3400-3410.

Qiu et al., "Targeting connexin43 expression accelerates the rate of wound repair," *Current Biology*, 2003, 13:1697-1703.

Ruch et al., *Molecular Carcinogenesis*, 14:269-274.

Ramdas et al., *J. Biol. Chem.*, 1989, 264:17395.

Ramer et al., *Spinal Cord.*, 2000, 38:449-472.

Ramezani et al., *Frontiers in Bioscience*, 2002, 7:29-36.

Ratkay-Traub et al., "Regeneration of rabbit cornea following excimer laser photorefractive keratectomy: a study on gap junctions, epithelial junctions and epidermal growth factor receptor expression in correlation with cell proliferation," *Exp. Eye Res.*, 2001, 73:291-302.

Reddy et al., *Pediatric Research*, 1998, 43(5):674-682.

Reeck et al., "'Homology' in proteins and nucleic acids: A terminology muddle and a way out of it," *Cell*, Aug. 28, 1987, 50(5):667.

Rennick et al., "Expression of connexin43 gap junctions between cultured vascular smooth muscle cells is dependent upon phenotype," *Cell Tissue Res.*, Feb. 1993, PMID: 8384084 [PubMed—indexed for Medline], 271(2):323-332.

Reynolds et al., *Nat. Med.*, 2005, 11:167-174.

Rigas et al., *Proc. Natl. Acad. Sci. USA*, 1986, 83:9591.

Rininsland et al., *Proc. Natl. Acad. Sci. USA*, 1997, 94:5854.

Robbins et al., *Pathologic basis of disease*, 2$^{nd}$ edition, Chapters 1-3, 1979, WB Saunders Co., Philadelphia.

Roberts et al., *Proc. Natl. Acad. Sci. USA*, 1986, 83:4167-4171.

Roberts et al., "Follicle-stimulating hormone affects metaphase I chromosome alignment and increases aneuploidy in mouse oocytes matured in vitro," *Biol. Reprod.*, 2005, 72:107-118.

Roelfsema et al., *J. Cereb. Blood Flow Metab.*, 2004, 24(8):877-886.

Rosendaal et al., "Up-regulation of the connexin43+ gap junction network in haemopoietic tissue before the growth of stem cells," *J. Cell Sci.*, Jan. 1994, 107(1):29-37.

Rozenthal et al., "Stable Transfection With Connexin43 Inhibits Neuronal Differentiation of PC12 Cells," *Society For Neuroscience Abstracts*, Oct. 25, 1997, 23(1-3):22.

Rutherford, *Vascular Surgery*, 3$^{rd}$ Ed., 1989, WB Saunders Co.

Sabiston, *The Textbook of Surgery*, 3$^{rd}$ Ed., Chapter 56, 1991, WB Saunders Co.

Saison-Behmoaras et al., *EMBO J.*, 1991, 10:1111-1118.

Saitongdee et al., "Levels of gap junction proteins in coronary arterioles and aorta of hamsters exposed to cold and during hibernation and arousal," *J. Histochem. Cytochem.*, 2004, 52:603-615.

Saitongdee et al., "Increased connexin43 gap junction protein in hamster cardiomyocytes during cold acclimatization and hibernation," *Cardiovascular Res.*, 2000, 47:108-115.

Sambrook et al., *Molecular Cloning: A Laboratory Manual*, 3$^{rd}$ Edition, Chapter 10, 1989.

Sambrook et al., *Molecular Cloning: A Laboratory Manual*, Chapters 11-12, 1989.

Sanghvi, *Antisense Research and Applications*, Chapter 15, Crooke et al., eds., 1993, CRC Press, pp. 276-278.

Santoro et al., A General Purpose RNA-Cleaving DNA Enzyme, *Proc. Natl. Acad. Sci. USA*, 1997, 94:4262-4266.

Santoro et al., *Biochem.*, 1998, 37:13330-13342.

Scatchard et al., *Ann. N.Y. Acad. Sci.*, 1949, 51(4):660.

Shah, M. et al., "Role of Elevated Plasma Transforming Growth Factor-β1 Levels in Wound Healing", *Am. J. Pathol.*, 1999, 154(4):1115-1124.

Scherer et al., *Nature Biotechnol.*, 2003, 21(12):1457-1465.

Schmidt et al., *Ann. Rev. Biomed. Eng.*, 2003, 5:293-347.

Schubert et al., *Nucleic Acids*, 2003, 31:5982-5992.

Schuck, "Reliable determination of binding affinity and kinetics using surface plasmon resonance biosensor," *Current Opinions in Biotechnology*, 1997, 8(4):498-502.

Severs et al., Intercellular junctions and the application of microscopical techniques: the cardiac gap junction as a case model, *J. Microsc.*, Mar. 1993, PMID: 8478912 [PubMed—indexed for Medline], 169(3):299-328.

Severs et al., "Fate of gap junctions in isolated adult mammalian cardiomyocytes," *Circ. Res.*, Jul. 1989, PMID: 2736737 [PubMed—indexed for Medline], 65(1):22-42.

Severs et al., "Integrity of the dissociated adult cardiac myocyte: gap junction tearing and the mechanism of plasma membrane resealing," *J. Muscle Res. Cell Motil.*, Apr. 1990, PMID: 2351753 [PubMed—indexed for Medline], 11(2):154-166.

Shah et al., *Am. J. Pathol.*, 1999, 154:1115-1124.

Shea et al., *Nucl. Acids Res.*, 1990, 18:3777-3783.

Simons et al., "Anti-sense c-myb oligonucleotides inhibit intimal arterial smooth muscle cell accumulation in vivo," *Nature*, 359:67-70.

(56) References Cited

OTHER PUBLICATIONS

Smith et al., "Altered patterns of gap junction distribution in ischemic heart disease: An immunohistochemical study of human myocardium using laser scanning confocal microscopy," *Am. J. Pathol.*, Oct. 1991, PMID: 1656760 [PubMed—indexed for Medline], 139(4):801-821.
Sotozono, C. et al., "Keratinocyte Growth Factor Accelerates Corneal Epithelial Wound Healing In Vivo", *Investigative Opthalmology &Visual Science*, 1995, 36(8):1524-1529.
Spanos et al., "Caspase activity and expression of cell death genes during human preimplantation embryo development," *J. Reprod.*, 2002, 124:353-363.
Spencer, "The cornea," from *Ophthalmic Pathology: An atlas and textbook*, 4th Ed., 1996, WB Saunders Co., Philadelphia, pp. 157-165.
Stein et al, eds., *Applied Antisense Oligonucleotide Technology*, Chapters 7, 10, and 22, 1998, Wiley-Liss.
Stein, "Anti-sense oligodeoxynucleotides—promises and pitfalls," *Leukemia*, 6:967-974.
Stewart et al., *Solid Phase Peptide Synthesis*, Chapter 2, part B—Chapter 3, 1969, W.H. Freeman Co., San Francisco.
Stillnovic et al., "Texture analysis of collagen fibers in scar tissue," *Proc. Image Vision Computing New Zealand*, Nov. 21, 2004, pp. 185-190.
Strobel et al., *Science*, 1991, 254:1639.
Sui et al., *Proc. Natl. Acad. Sci. USA*, 2002, 99(8):5515-5520.
Sundstrom, *Drug Discovery Today*, 2005, 10:993-1000.
Svinarchuk et al., *Biochimie*, 1993, 75:49-54.
Takahashi et al., *J. Pharm. Pharmacol.*, 1998, 40:252-257.
Tan et al., *Ann. Neurol.*, 1992, 32(5):677-682.
Tanaka et al., *Jpn. J. Ophthalmol.*, 1999, 43:348-354.
Tarnow et al., *Scand. J. Plast. Reconstr. Hand Surg.*, 1994, 28:255-259.
Topol, ed., *The Textbook of Interventional Cardiology*, 2nd Ed., 1994, WB Saunders Co.
Uhlmann et al., *Chem. Reviews*, 1990, 90:543-584.
UCL Media Relations, "New bio-active gel cuts wound healing time in half," University College London, Oct. 20, 2003, accessed online Sep. 29, 2006 at http://www.ucl.ac.uk/media/library/nexagon0.
UCL News, "Wound-healing technology shortlisted for award," University College London, accessed online Sep. 27, 2006 at http://www.ucl.ac.uk/news-archive/archive/2003/october-2003/latest/newsitem.shtml?0309 . . . .
Veber et al., *TINS*, 1985, 392.
Vikis et al., "Glutathione-S-Transferase-Fusion Based Assays for Studying Protein-Protein Interactions" from *Protein-Protein Interactions, Methods and Application, Methods in Molecular Biology*, Fu, ed., 2004, pp. 175-186, Humana Press, Totowa, N.J.
Vis et al, "Connexin expression in Huntington's diseased human brain," *Cell Biol. Int.*, Nov. 1998, PMID: 10873295 [PubMed—indexed for Medline], 22(11-12):837-847.
Waggett et al., "Connexin 32 and 43 gap junctions differentially modulate tenocyte esonse to cyclic mechanical load," *Eur. J. Cell. Biol.*, 2006, 85:1145-1154.
Wagner et al., "Gene inhibition using anti-sense oligodeoxynucleotides," *Nature*, 1994, 372:333-335.
Walker et al., *Dev. Biol.*, 2005, 284:479-498.
Waring et al., *Amer. J. Opthalmol.*, 1991, 111:133.
Wei, C.J. et al., "Connexins and Cell Signaling in Development and Disease", *Am. Rev. Cell Dev. Biol.*, 2004, 20:811-838.
Wild, ed., *The Immunoassay Handbook*, 1994, Stockton Press, New York.
Willecke et al., "Structural and functional diversity of connexin genes in the mouse and human genome," *Biological Chemistry*, May 2002, 383(5):2002-2005.
Willecke et al., *Biol. Chem.*, 2002, 383:725-737.
Wilson et al., "Accellular Matrix," *Trans. Am. Soc. Artif. Intern*, 1990, 36:340-343.
Wright et al., "Stage-specific and differential expression of gap junctions in the mouse ovary: connexin-specific roles in follicular regulation," *J. Reprod. Fert.*, 2001, 121:77-88.
Wyngaarden et al., eds., *The Cecil Textbook of Medicine*, 19th Ed., 1992, WB Saunders.
Xu et al., *J. Comp. Neurol.*, 1995, 351:145-160.
Xianyuan et al., "The studies on thymosin β4 and the prospect thereof," *Foreign Medical Sciences (Section of Biologics for Phophylaxis, Diagnosis and Therapy)*, Dec. 31, 2002, 25(3):126-129.
Xu et al., *J. Neuroscience*, 1999, 11:1723-1740.
Yamashita et al., *J. Pharm. Pharmacol.*, 1987, 39:621-626.
Yang et al., *Proc. Natl. Acad. Sci. USA*, Sep. 1, 1998, 95(18):10836-10841.
Yick et al., *Exp. Neurol.*, 1999, 159:131-138.
Zhang et al., "Use of surface plasmon resonance for the measurement of low affinity binding interactions between HSP72 and measles virus nucleocapsid protein," *Biological Procedures Onlin.*, 2003, 5(1):170-181.
Zimmer et al., "Topological analysis of the major protein in isolated intact rat liver gap junctions and gap junctions-derived single membrane structures," *J. Biol. Chem.*, Jun. 5, 1987, PMID: 3034905 [PubMed—indexed for Medline], 262(16):7751-7763.
Zlotnik et al., *Annu. Rev. Immunol.*, 2000, 18:217-242.
Zon, *Ann. N.Y. Acad. Sci.*, 1990, 616:161-172.
Official Action, AU 2004294824, dated May 28, 2009.
Examiner's First Report, CA 2,361,251, dated Apr. 11, 2006.
Examiner's Second Report, CA 2,361,251, dated Nov. 20, 2006.
Examiner's Third Report, CA 2,361,251, dated Jun. 27, 2007.
Examiner's Fourth Report, CA 2,361,251, dated Mar. 17, 2008.
Examiner's Fifth Report, CA 2,361,251, dated Dec. 10, 2008.
Examiner's Sixth Report, CA 2,361,251, dated Oct. 23, 2009.
First Official Action, CN 200480041251.9, dated Jul. 4, 2008.
First Official Action, CN 200780049832.0, dated Nov. 18, 2007.
Examination Report, EA 200601071, dated Jul. 19, 2007.
Examination Report, NZ 548204, dated Aug. 5, 2009.
Examination Report, NZ 561098, dated Mar. 17, 2009.
Written Opinion, PCT/IB2006/001961, dated May 13, 2008.
International Preliminary Report on Patentability, PCT/GB00/00238, dated Apr. 10, 2001.
International Search Report, PCT/GB00/00238, dated Jun. 19, 2000.
Final Office Action, U.S. Appl. No. 09/890,363, dated Jul. 22, 2005.
Final Office Action, U.S. Appl. No. 11/447,599, dated Sep. 18, 2009.
Final Office Action, U.S. Appl. No. 11/510,498, dated Feb. 4, 2010.
Final Office Action, U.S. Appl. No. 11/512,725, dated Aug. 27, 2009.
Final Office Action, U.S. Appl. No. 11/512,730, dated Nov. 26, 2008.
Final Office Action, U.S. Appl. No. 11/512,735, dated Nov. 26, 2008.
Non-final Office Action, U.S. Appl. No. 09/890,363, dated Apr. 30, 2003.
Non-final Office Action, U.S. Appl. No. 11/447,599, dated Mar. 13, 2008.
Non-final Office Action, U.S. Appl. No. 11/510,496, dated Mar. 14, 2008.
Non-final Office Action, U.S. Appl. No. 11/510,498, dated Dec. 2, 2008.
Non-final Office Action, U.S. Appl. No. 11/512,725, dated Nov. 26, 2008.
Non-final Office Action, U.S. Appl. No. 11/512,730, dated Feb. 8, 2008.
Non-final Office Action, U.S. Appl. No. 11/512,735, dated Feb. 7, 2008.
Non-final Office Action, U.S. Appl. No. 10/581,813, dated Dec. 22, 2008.
Office Action dated Mar. 26, 2015 from related Japanese Patent Application No. 2009-537229 (with translation of list of cited references), 6 total pages.
Office Action dated May 15, 2015, from related Japanese Patent Application No. 2013-051646, 3 total pages.
Office Action dated Jan. 4, 2017, from related Japanese Patent Application No. 2016-0847398, 4 total pages.

(56) References Cited

OTHER PUBLICATIONS

Preliminary Rejection in Korean Patent Application No. 10-2015-7015461, dated Nov. 4, 2015, 8 pages.
Requirement for Restriction/Election, U.S. Appl. No. 10/581,813, dated Nov. 5, 2009.
International Search Report, WO 2006/134494, dated May 13, 2008.
International Search Report, WO 2005/053600, dated Jun. 16, 2005.
International Search Report, WO 2008/073479, dated Jul. 15, 2008.
*Concise Encylopedia of Polymer Science and Engineering*, 1990, pp. 858-859.
"Medical Futures—Innovation Awards," accessed online May 26, 2006 at http://www.medicalfutures.co.uk/runner.php?txtWin=1.
Postlethwaite et al., "Stimulation of the chemotactic migration of human fibroblasts by transforming growth factor β," *J. Exp. Med.*, Jan. 1987, 165:251-256.
Weir et al., eds., *Handbook of Experimental Immunology*, vol. 3: Genetics and Molecular Immunology, $4^{th}$ edition, Chapters 85 and 86, 1986, Blackwell Scientific Publications, Oxford, UK.
NCBI Genbank Accession No. AF151980, defined as "*Homo sapiens* connexin 43 (CX43) gene, complete cds," dated Dec. 19, 2000, in 2 pages.
Notification of Second Office Action dated Apr. 3, 2013 from corresponding Chinese Patent Application No. 200780049832.0, 24 total pages.
Notice of Final Rejection dated Jul. 17, 2013 from corresponding Japanese Patent Application No. 2009-537229, 4 total pages.
First Examination Report dated Sep. 3, 2013 from corresponding Australian Patent Application No. 614724, 3 pages.
Examiner's Report dated Nov. 6, 2013, from related Canadian Patent Application No. 2,669,832, 5 pages.
Examination Report dated Apr. 14, 2014, from related European Patent Application No. 07862038.8, 8 pages.
Office Action dated May 19, 2014, from related Japanese Patent Application No. 2013-051646, 3 total pages.
First Examination Report dated Jul. 26, 2013, in corresponding New Zealand Patent Application No. 613395, 2 pages.

FIG. 1A
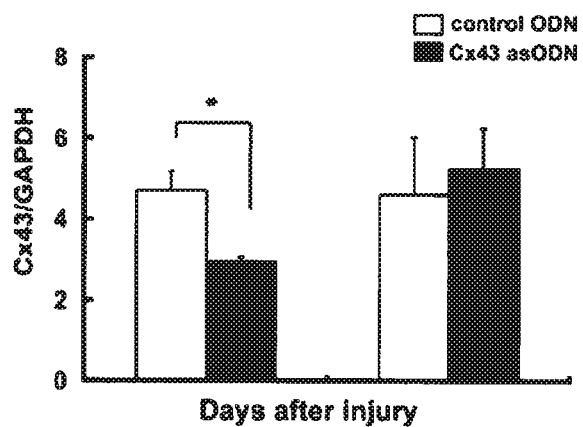
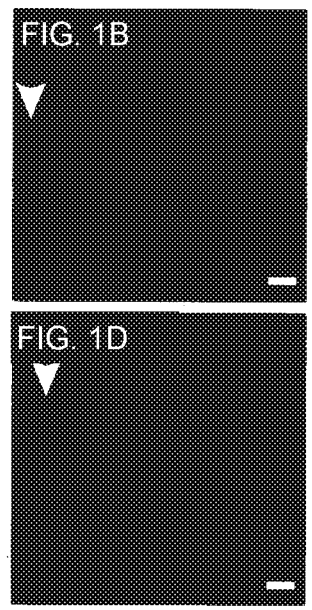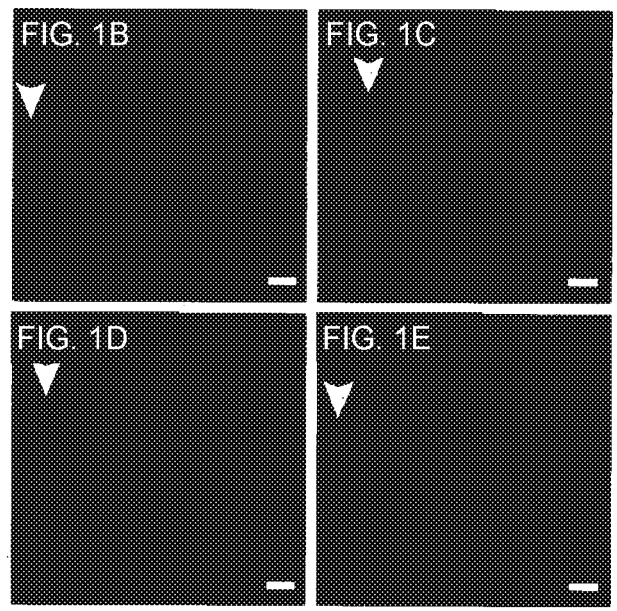
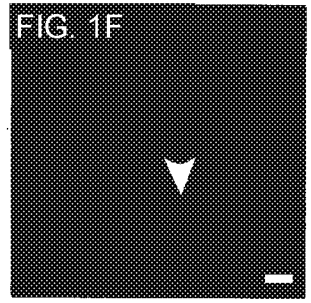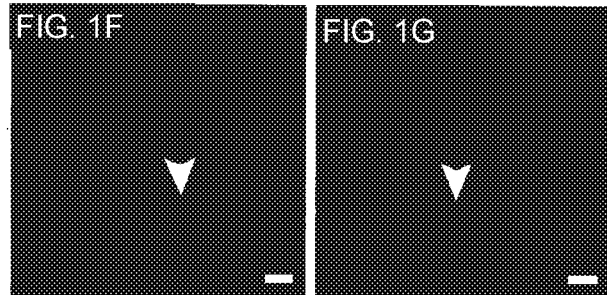
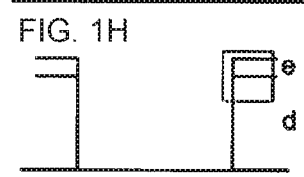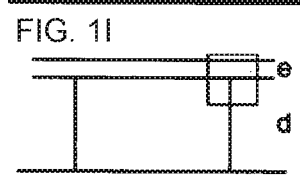

FIG. 6A
FIG. 6B  FIG. 6C
FIG. 6D 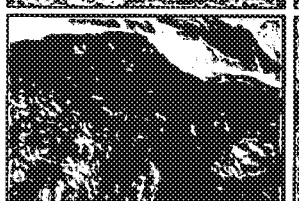 FIG. 6E
FIG. 6F
FIG. 6G  FIG. 6H
FIG. 6I  FIG. 6J
FIG. 6K
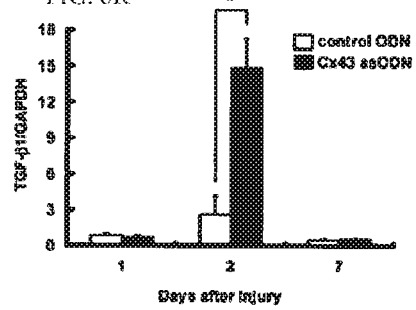

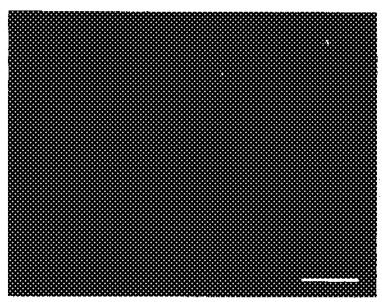
FIG. 7A
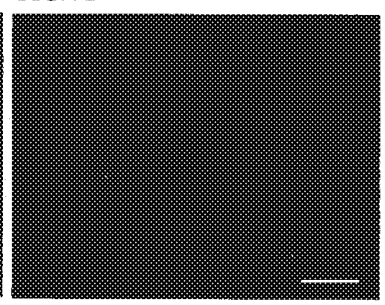
FIG. 7B
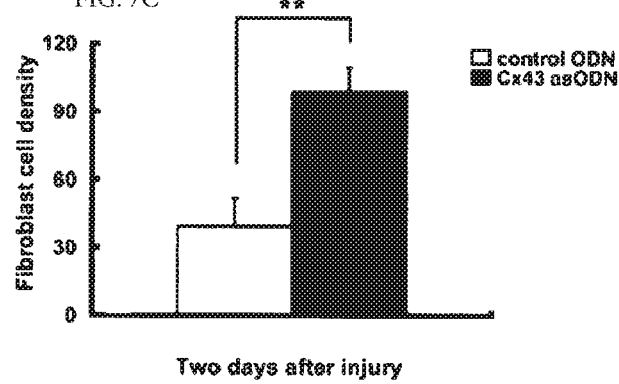
FIG. 7C
Two days after injury
FIG. 7D
Four hours after injury
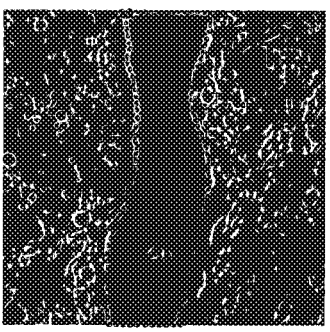
FIG. 7E
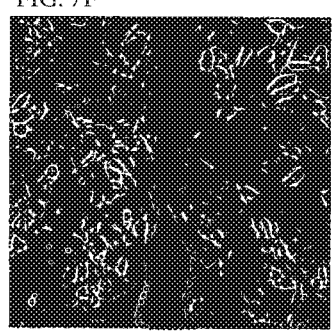
FIG. 7F

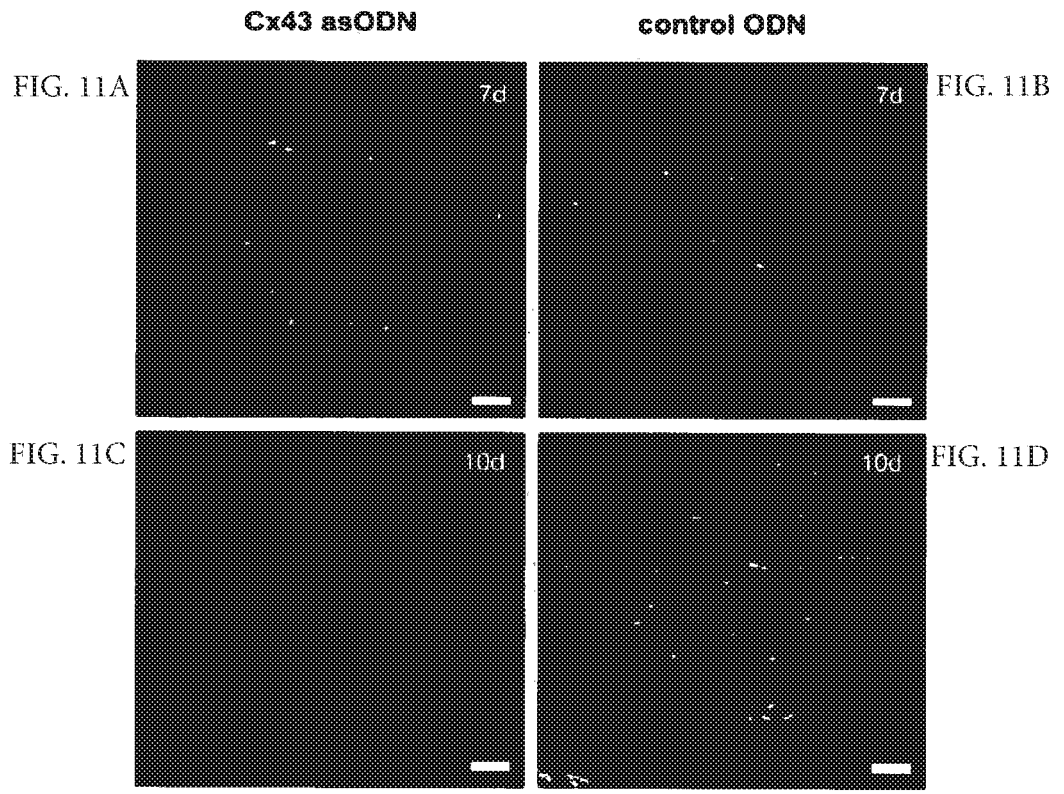
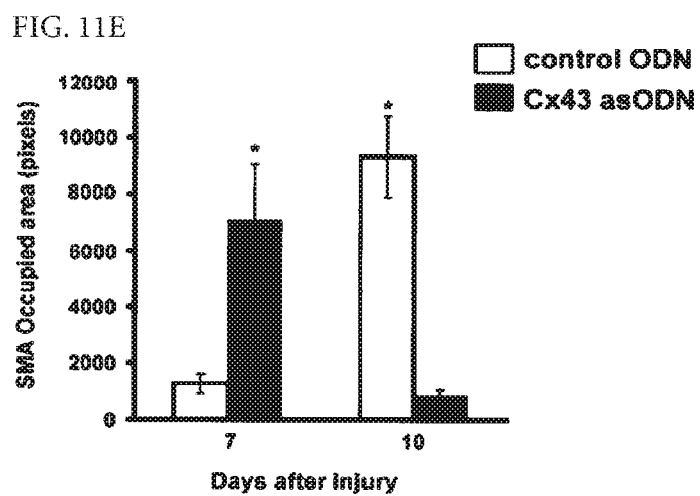
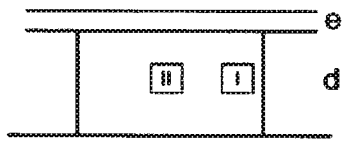
FIG. 11A  FIG. 11B  FIG. 11C  FIG. 11D  FIG. 11E  FIG. 11F

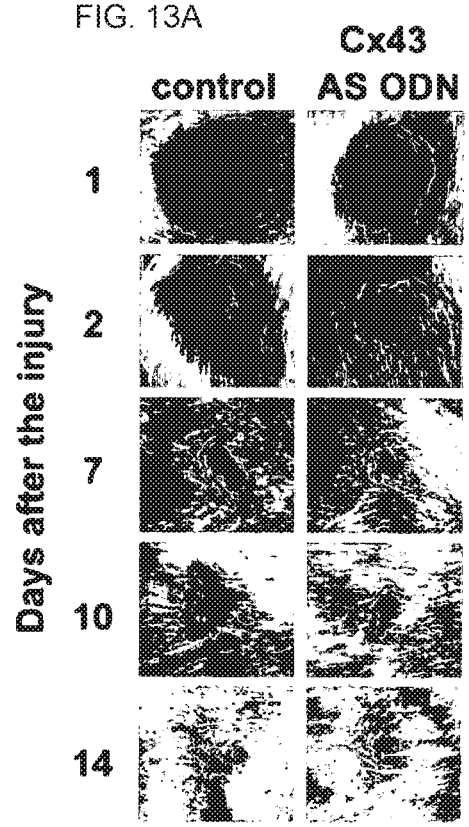
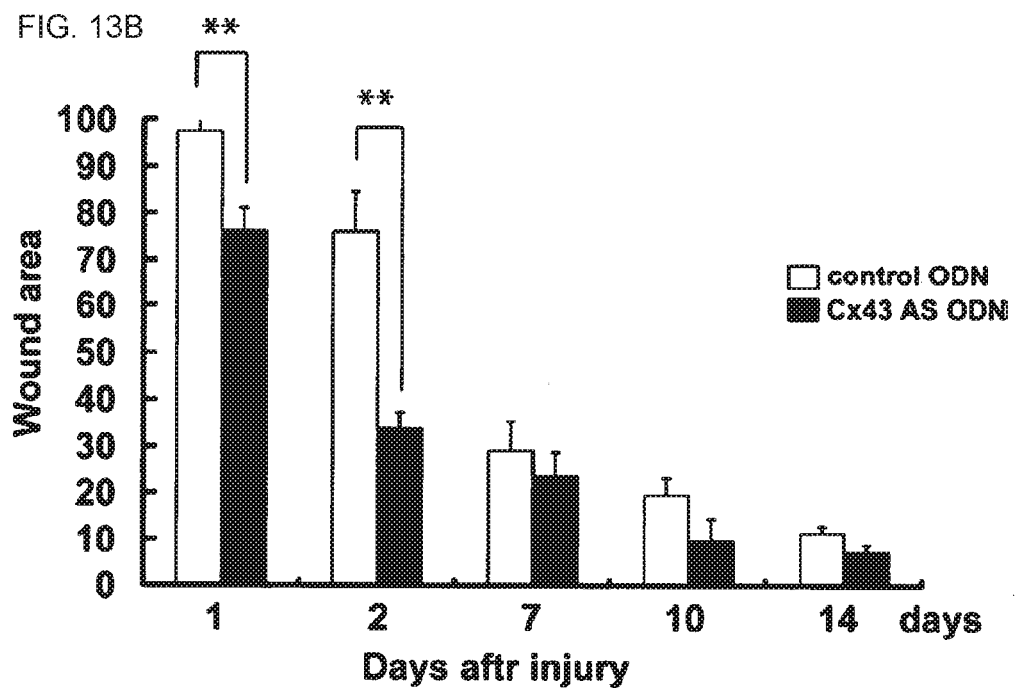

SEQUENCE LISTING

```
<160> NUMBER OF SEQ ID NOS: 135

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtaattgcgg caagaagaat tgtttctgtc                                          30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gtaattgcgg caggaggaat tgtttctgtc                                          30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggcaagagac accaaagaca ctaccagcat                                          30

<210> SEQ ID NO 4
```

```
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcctgagcaa tacctaacga acaaata                                              27

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
catctccttg gtgctcaacc                                                      20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
ctgaagtcga cttggcttgg                                                      20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctcagatagt ggccagaatg c                                                    21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ttgtccaggt gactccaagg                                                      20

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cgtccgagcc cagaaagatg aggtc                                                25

<210> SEQ ID NO 10
<211> LENGTH: 19
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
agaggcgcac gtgagacac                                                   19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tgaagacaat gaagatgtt                                                   19

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tttcttttct atgtgctgtt ggtga                                            25

<210> SEQ ID NO 13
<211> LENGTH: 396
<212> TYPE: PRT
<213> ORGANISM: Homo sapiens

<400> SEQUENCE: 13
```

Met Ser Trp Ser Phe Leu Thr Arg Leu Leu Glu Glu Ile His Asn His
1               5                   10                  15

Ser Thr Phe Val Gly Lys Ile Trp Leu Thr Val Leu Ile Val Phe Arg
            20                  25                  30

Ile Val Leu Thr Ala Val Gly Gly Glu Ser Ile Tyr Tyr Asp Glu Gln
        35                  40                  45

Ser Lys Phe Val Cys Asn Thr Glu Gln Pro Gly Cys Glu Asn Val Cys
    50                  55                  60

Tyr Asp Ala Phe Ala Pro Leu Ser His Val Arg Phe Trp Val Phe Gln
65                  70                  75                  80

Ile Ile Leu Val Ala Thr Pro Ser Val Met Tyr Leu Gly Tyr Ala Ile
                85                  90                  95

His Lys Ile Ala Lys Met Glu His Gly Glu Ala Asp Lys Lys Ala Ala
            100                 105                 110

Arg Ser Lys Pro Tyr Ala Met Arg Trp Lys Gln His Arg Ala Leu Glu
        115                 120                 125

Glu Thr Glu Glu Asp Asn Glu Glu Asp Pro Met Met Tyr Pro Glu Met
    130                 135                 140

Glu Leu Glu Ser Asp Lys Glu Asn Lys Glu Gln Ser Gln Pro Lys Pro
145                 150                 155                 160

Lys His Asp Gly Arg Arg Arg Ile Arg Glu Asp Gly Leu Met Lys Ile
                165                 170                 175

Tyr Val Leu Gln Leu Leu Ala Arg Thr Val Phe Glu Val Gly Phe Leu
            180                 185                 190

```
Ile Gly Gln Tyr Phe Leu Tyr Gly Phe Gln Val His Pro Phe Tyr Val
            195                 200                 205

Cys Ser Arg Leu Pro Cys Pro His Lys Ile Asp Cys Phe Ile Ser Arg
210                 215                 220

Pro Thr Glu Lys Thr Ile Phe Leu Leu Ile Met Tyr Gly Val Thr Gly
225                 230                 235                 240

Leu Cys Leu Leu Leu Asn Ile Trp Glu Met Leu His Leu Gly Phe Gly
            245                 250                 255

Thr Ile Arg Asp Ser Leu Asn Ser Lys Arg Arg Glu Leu Glu Asp Pro
            260                 265                 270

Gly Ala Tyr Asn Tyr Pro Phe Thr Trp Asn Thr Pro Ser Ala Pro Pro
            275                 280                 285

Gly Tyr Asn Ile Ala Val Lys Pro Asp Gln Ile Gln Tyr Thr Glu Leu
            290                 295                 300

Ser Asn Ala Lys Ile Ala Tyr Lys Gln Asn Lys Ala Asn Thr Ala Gln
305                 310                 315                 320

Glu Gln Gln Tyr Gly Ser His Glu Glu Asn Leu Pro Ala Asp Leu Glu
            325                 330                 335

Ala Leu Gln Arg Glu Ile Arg Met Ala Gln Glu Arg Leu Asp Leu Ala
            340                 345                 350

Val Gln Ala Tyr Ser His Gln Asn Asn Pro His Gly Pro Arg Glu Lys
            355                 360                 365

Lys Ala Lys Val Gly Ser Lys Ala Gly Ser Asn Lys Ser Thr Ala Ser
            370                 375                 380

Ser Lys Ser Gly Asp Gly Lys Asn Ser Val Trp Ile
385                 390                 395

<210> SEQ ID NO 14
<211> LENGTH: 382
<212> TYPE: PRT
<213> ORGANISM: Homo sapiens

<400> SEQUENCE: 14

Met Gly Asp Trp Ser Ala Leu Gly Lys Leu Leu Asp Lys Val Gln Ala
1               5                   10                  15

Tyr Ser Thr Ala Gly Gly Lys Val Trp Leu Ser Val Leu Phe Ile Phe
            20                  25                  30

Arg Ile Leu Leu Leu Gly Thr Ala Val Glu Ser Ala Trp Gly Asp Glu
            35                  40                  45

Gln Ser Ala Phe Arg Cys Asn Thr Gln Gln Pro Gly Cys Glu Asn Val
50                  55                  60

Cys Tyr Asp Lys Ser Phe Pro Ile Ser His Val Arg Phe Trp Val Leu
65                  70                  75                  80

Gln Ile Ile Phe Val Ser Val Pro Thr Leu Leu Tyr Leu Ala His Val
            85                  90                  95

Phe Tyr Val Met Arg Lys Glu Glu Lys Leu Asn Lys Lys Glu Glu Glu
            100                 105                 110

Leu Lys Val Ala Gln Thr Asp Gly Val Asn Val Asp Met His Leu Lys
            115                 120                 125

Gln Ile Glu Ile Lys Lys Phe Lys Tyr Gly Ile Glu Glu His Gly Lys
            130                 135                 140

Val Lys Met Arg Gly Gly Leu Leu Arg Thr Tyr Ile Ile Ser Ile Leu
145                 150                 155                 160

Phe Lys Ser Ile Phe Glu Val Ala Phe Leu Leu Ile Gln Trp Tyr Ile
```

```
                165                 170                 175
Tyr Gly Phe Ser Leu Ser Ala Val Tyr Thr Cys Lys Arg Asp Pro Cys
            180                 185                 190

Pro His Gln Val Asp Cys Phe Leu Ser Arg Pro Thr Glu Lys Thr Ile
        195                 200                 205

Phe Ile Ile Phe Met Leu Val Val Ser Leu Val Ser Leu Ala Leu Asn
    210                 215                 220

Ile Ile Glu Leu Phe Tyr Val Phe Phe Lys Gly Val Lys Asp Arg Val
225                 230                 235                 240

Lys Gly Lys Ser Asp Pro Tyr His Ala Thr Ser Gly Ala Leu Ser Pro
            245                 250                 255

Ala Lys Asp Cys Gly Ser Gln Lys Tyr Ala Tyr Phe Asn Gly Cys Ser
        260                 265                 270

Ser Pro Thr Ala Pro Leu Ser Pro Met Ser Pro Pro Gly Tyr Lys Leu
    275                 280                 285

Val Thr Gly Asp Arg Asn Asn Ser Ser Cys Arg Asn Tyr Asn Lys Gln
290                 295                 300

Ala Ser Glu Gln Asn Trp Ala Asn Tyr Ser Ala Glu Gln Asn Arg Met
305                 310                 315                 320

Gly Gln Ala Gly Ser Thr Ile Ser Asn Ser His Ala Gln Pro Phe Asp
            325                 330                 335

Phe Pro Asp Asn Gln Asn Ser Lys Lys Leu Ala Ala Gly His Glu
        340                 345                 350

Leu Gln Pro Leu Ala Ile Val Asp Gln Arg Pro Ser Ser Arg Ala Ser
            355                 360                 365

Ser Arg Ala Ser Ser Arg Pro Arg Pro Asp Asp Leu Glu Ile
370                 375                 380
```

<210> SEQ ID NO 15
<211> LENGTH: 11
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 15

```
Phe Glu Val Ala Phe Leu Leu Ile Gln Trp Ile
1               5                   10
```

<210> SEQ ID NO 16
<211> LENGTH: 11
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 16

```
Leu Leu Ile Gln Trp Tyr Ile Gly Phe Ser Leu
1               5                   10
```

<210> SEQ ID NO 17
<211> LENGTH: 16
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 17

Ser Leu Ser Ala Val Tyr Thr Cys Lys Arg Asp Pro Cys Pro His Gln
1               5                   10                  15

<210> SEQ ID NO 18
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 18

Val Asp Cys Phe Leu Ser Arg Pro Thr Glu Lys Thr
1               5                   10

<210> SEQ ID NO 19
<211> LENGTH: 11
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 19

Ser Arg Pro Thr Glu Lys Thr Ile Phe Ile Ile
1               5                   10

<210> SEQ ID NO 20
<211> LENGTH: 13
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 20

Leu Gly Thr Ala Val Glu Ser Ala Trp Gly Asp Glu Gln
1               5                   10

<210> SEQ ID NO 21
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 21

Gln Ser Ala Phe Arg Cys Asn Thr Gln Gln Pro Gly
1               5                   10

<210> SEQ ID NO 22
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 22

Gln Gln Pro Gly Cys Glu Asn Val Cys Tyr Asp Lys
1               5                   10

<210> SEQ ID NO 23
<211> LENGTH: 13
<212> TYPE: PRT
<213> ORGANISM: Unknown Organism

```
<220> FEATURE:
<223> OTHER INFORMATION: Description of Unknown Organism: Unknown
      exemplary connexin peptide

<400> SEQUENCE: 23

Val Cys Tyr Asp Lys Ser Phe Pro Ile Ser His Val Arg
1               5                   10

<210> SEQ ID NO 24
<211> LENGTH: 38
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 24

Ala Ala Glu Ser Val Trp Gly Asp Glu Ile Lys Ser Ser Phe Ile Cys
1               5                   10                  15

Asn Thr Leu Gln Pro Gly Cys Asn Ser Val Cys Tyr Asp His Phe Phe
            20                  25                  30

Pro Ile Ser His Val Arg
        35

<210> SEQ ID NO 25
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 25

Glu Ser Val Trp Gly Asp Glu Lys Ser Ser Phe Ile
1               5                   10

<210> SEQ ID NO 26
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 26

Ile Cys Asn Thr Leu Gln Pro Gly Cys Asn Ser Val
1               5                   10

<210> SEQ ID NO 27
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 27

Ser Val Cys Tyr Asp His Phe Phe Pro Ile Ser His
1               5                   10

<210> SEQ ID NO 28
<211> LENGTH: 25
<212> TYPE: PRT
<213> ORGANISM: Unknown Organism
<220> FEATURE:
<223> OTHER INFORMATION: Description of Unknown Organism: Unknown
      exemplary connexin peptide
```

```
<400> SEQUENCE: 28

Arg Leu Val Lys Cys Glu Ala Phe Pro Cys Pro Asn Thr Val Asp Cys
1               5                   10                  15

Phe Val Ser Arg Pro Thr Glu Lys Thr
            20                  25

<210> SEQ ID NO 29
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 29

Val Lys Cys Glu Ala Phe Pro Cys Pro Asn Thr Val
1               5                   10

<210> SEQ ID NO 30
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 30

Val Asp Cys Phe Val Ser Arg Pro Thr Glu Lys Thr
1               5                   10

<210> SEQ ID NO 31
<211> LENGTH: 13
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 31

Val Cys Tyr Asp His Phe Phe Pro Ile Ser His Val Arg
1               5                   10

<210> SEQ ID NO 32
<211> LENGTH: 18
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 32

Val Trp Gly Asp Glu Lys Ser Ser Phe Ile Cys Asn Thr Leu Gln Pro
1               5                   10                  15

Gly Tyr

<210> SEQ ID NO 33
<211> LENGTH: 15
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 33

Asp Glu Lys Ser Ser Phe Ile Cys Asn Thr Leu Gln Pro Gly Tyr
```

-continued

```
1               5                   10                  15
```

<210> SEQ ID NO 34
<211> LENGTH: 11
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 34

```
Ser Arg Pro Thr Glu Lys Thr Val Phe Thr Val
1               5                   10
```

<210> SEQ ID NO 35
<211> LENGTH: 7
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 35

```
Ser Arg Pro Thr Glu Lys Thr
1               5
```

<210> SEQ ID NO 36
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 36

```
Ile Cys Asn Thr Leu Gln Pro Gly Cys Asn Ser Val
1               5                   10
```

<210> SEQ ID NO 37
<211> LENGTH: 16
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 37

```
Phe Leu Asp Thr Leu His Val Cys Arg Arg Ser Pro Cys Pro His Pro
1               5                   10                  15
```

<210> SEQ ID NO 38
<211> LENGTH: 18
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 38

```
Lys Arg Asp Pro Cys His Gln Val Asp Cys Phe Leu Ser Arg Pro Thr
1               5                   10                  15

Glu Lys
```

<210> SEQ ID NO 39
<211> LENGTH: 35
<212> TYPE: PRT
<213> ORGANISM: Unknown Organism

```
<220> FEATURE:
<223> OTHER INFORMATION: Description of Unknown Organism: Unknown
      exemplary connexin peptide

<400> SEQUENCE: 39

Lys Glu Val Trp Gly Asp Glu Gln Ala Asp Phe Val Cys Asn Thr Leu
1               5                   10                  15

Gln Pro Gly Cys Lys Asn Val Cys Tyr Asp His Tyr Phe Pro Ile Ser
            20                  25                  30

His Ile Arg
        35

<210> SEQ ID NO 40
<211> LENGTH: 35
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 40

Gln Glu Val Trp Gly Asp Glu Gln Asp Phe Val Cys Asn Thr Leu
1               5                   10                  15

Gln Pro Gly Cys Lys Asn Val Cys Tyr Asp His Phe Phe Pro Val Ser
            20                  25                  30

His Ile Arg
        35

<210> SEQ ID NO 41
<211> LENGTH: 35
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 41

Glu Glu Val Trp Asp Asp Glu Gln Lys Asp Phe Val Cys Asn Thr Lys
1               5                   10                  15

Gln Pro Gly Cys Pro Asn Val Cys Tyr Asp Glu Phe Phe Pro Val Ser
            20                  25                  30

His Val Arg
        35

<210> SEQ ID NO 42
<211> LENGTH: 35
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 42

Glu Arg Val Trp Gly Asp Glu Gln Lys Asp Phe Asp Cys Asn Thr Lys
1               5                   10                  15

Gln Pro Gly Cys Thr Asn Val Cys Tyr Asp Asn Tyr Phe Pro Ile Ser
            20                  25                  30

Asn Ile Arg
        35

<210> SEQ ID NO 43
<211> LENGTH: 35
<212> TYPE: PRT
```

<213> ORGANISM: Unknown Organism
<220> FEATURE:
<223> OTHER INFORMATION: Description of Unknown Organism: Unknown
    exemplary connexin peptide

<400> SEQUENCE: 43

Glu Arg Val Trp Ser Asp Asp His Lys Asp Phe Asp Cys Asn Thr Arg
1               5                   10                  15

Gln Pro Gly Cys Ser Asn Val Cys Phe Asp Glu Phe Phe Pro Val Ser
            20                  25                  30

His Val Arg
        35

<210> SEQ ID NO 44
<211> LENGTH: 35
<212> TYPE: PRT
<213> ORGANISM: Unknown Organism
<220> FEATURE:
<223> OTHER INFORMATION: Description of Unknown Organism: Unknown
    exemplary connexin peptide

<400> SEQUENCE: 44

Glu Ser Val Trp Gly Asp Glu Lys Ser Ser Phe Ile Cys Asn Thr Leu
1               5                   10                  15

Gln Pro Gly Cys Asn Ser Val Cys Tyr Asp Gln Phe Phe Pro Ile Ser
            20                  25                  30

His Val Arg
        35

<210> SEQ ID NO 45
<211> LENGTH: 35
<212> TYPE: PRT
<213> ORGANISM: Unknown Organism
<220> FEATURE:
<223> OTHER INFORMATION: Description of Unknown Organism: Unknown
    exemplary connexin peptide

<400> SEQUENCE: 45

Glu Ser Val Trp Gly Asp Glu Gln Ser Asp Phe Glu Cys Asn Thr Ala
1               5                   10                  15

Gln Pro Gly Cys Thr Asn Val Cys Tyr Asp Gln Ala Phe Pro Ile Ser
            20                  25                  30

His Ile Arg
        35

<210> SEQ ID NO 46
<211> LENGTH: 35
<212> TYPE: PRT
<213> ORGANISM: Unknown Organism
<220> FEATURE:
<223> OTHER INFORMATION: Description of Unknown Organism: Unknown
    exemplary connexin peptide

<400> SEQUENCE: 46

Glu Ser Val Trp Gly Asp Glu Gln Ser Asp Phe Glu Cys Asn Thr Ala
1               5                   10                  15

Gln Pro Gly Cys Thr Asn Val Cys Tyr Asp Gln Ala Phe Pro Ile Ser
            20                  25                  30

His Ile Arg
        35

<210> SEQ ID NO 47
<211> LENGTH: 35

```
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 47

Arg Pro Val Tyr Gln Asp Glu Gln Glu Arg Phe Val Cys Asn Thr Leu
1               5                   10                  15

Gln Pro Gly Cys Ala Asn Val Cys Tyr Asp Val Phe Ser Pro Val Ser
            20                  25                  30

His Leu Arg
        35

<210> SEQ ID NO 48
<211> LENGTH: 35
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 48

Glu Ser Ala Trp Gly Asp Glu Gln Ser Ala Phe Arg Cys Asn Thr Gln
1               5                   10                  15

Gln Pro Gly Cys Glu Asn Val Cys Tyr Asp Lys Ser Phe Pro Ile Ser
            20                  25                  30

His Val Arg
        35

<210> SEQ ID NO 49
<211> LENGTH: 35
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 49

Glu Asp Val Trp Gly Asp Glu Gln Ser Asp Phe Thr Cys Asn Thr Gln
1               5                   10                  15

Gln Pro Gly Cys Asx Asn Val Cys Tyr Asx Arg Ala Phe Pro Ile Ser
            20                  25                  30

His Ile Arg
        35

<210> SEQ ID NO 50
<211> LENGTH: 35
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 50

Glu Ala Ile Tyr Ser Asp Glu Gln Ala Lys Phe Thr Cys Asn Thr Arg
1               5                   10                  15

Gln Pro Gly Cys Asp Asn Val Cys Tyr Asp Ala Phe Ala Pro Leu Ser
            20                  25                  30

His Val Arg
        35

<210> SEQ ID NO 51
```

-continued

```
<211> LENGTH: 35
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 51

Glu Ser Ser Trp Gly Asp Glu Gln Ala Asp Phe Arg Cys Asp Thr Ile
1               5                   10                  15

Gln Pro Gly Cys Gln Asn Val Cys Thr Asp Gln Ala Phe Pro Ile Ser
            20                  25                  30

His Ile Arg
        35

<210> SEQ ID NO 52
<211> LENGTH: 36
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 52

Gly Glu Ser Ile Tyr Tyr Asp Glu Gln Ser Lys Phe Val Cys Asn Thr
1               5                   10                  15

Glu Gln Pro Gly Cys Glu Asn Val Cys Tyr Asp Ala Phe Ala Pro Leu
            20                  25                  30

Ser His Val Arg
        35

<210> SEQ ID NO 53
<211> LENGTH: 39
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 53

Met Tyr Val Phe Tyr Val Met Tyr Asp Gly Phe Ser Met Gln Arg Leu
1               5                   10                  15

Val Lys Cys Asn Ala Trp Pro Cys Pro Asn Thr Val Asp Cys Phe Val
            20                  25                  30

Ser Arg Pro Thr Glu Lys Thr
        35

<210> SEQ ID NO 54
<211> LENGTH: 39
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 54

Met Tyr Val Phe Tyr Phe Leu Tyr Asn Gly Tyr His Leu Pro Trp Val
1               5                   10                  15

Leu Lys Cys Gly Ile Asp Pro Cys Pro Asn Leu Val Asp Cys Phe Ile
            20                  25                  30

Ser Arg Pro Thr Glu Lys Thr
        35
```

```
<210> SEQ ID NO 55
<211> LENGTH: 39
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 55

Leu Tyr Ile Phe His Arg Leu Tyr Lys Asp Tyr Asp Met Pro Arg Val
1               5                   10                  15

Val Ala Cys Ser Val Glu Pro Cys Pro His Thr Val Asp Cys Tyr Ile
            20                  25                  30

Ser Arg Pro Thr Glu Lys Lys
        35

<210> SEQ ID NO 56
<211> LENGTH: 40
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 56

Leu Tyr Leu Leu His Thr Leu Trp His Gly Phe Asn Met Pro Arg Leu
1               5                   10                  15

Val Gln Cys Ala Asn Val Ala Pro Cys Pro Asn Ile Val Asp Cys Tyr
            20                  25                  30

Ile Ala Arg Pro Thr Glu Lys Lys
        35                  40

<210> SEQ ID NO 57
<211> LENGTH: 39
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 57

Leu Tyr Val Phe His Ser Phe Tyr Pro Lys Tyr Ile Leu Pro Pro Val
1               5                   10                  15

Val Lys Cys His Ala Asp Pro Cys Pro Asn Ile Val Asp Cys Phe Ile
            20                  25                  30

Ser Lys Pro Ser Glu Lys Asn
        35

<210> SEQ ID NO 58
<211> LENGTH: 39
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 58

Met Tyr Val Phe Tyr Leu Leu Tyr Pro Gly Tyr Ala Met Val Arg Leu
1               5                   10                  15

Val Lys Cys Asp Val Tyr Pro Cys Pro Asn Thr Val Asp Cys Phe Val
            20                  25                  30

Ser Arg Pro Thr Glu Lys Thr
        35
```

<210> SEQ ID NO 59
<211> LENGTH: 32
<212> TYPE: PRT
<213> ORGANISM: Unknown Organism
<220> FEATURE:
<223> OTHER INFORMATION: Description of Unknown Organism: Unknown
    exemplary connexin peptide

<400> SEQUENCE: 59

Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
            20                  25                  30

<210> SEQ ID NO 60
<211> LENGTH: 32
<212> TYPE: PRT
<213> ORGANISM: Unknown Organism
<220> FEATURE:
<223> OTHER INFORMATION: Description of Unknown Organism: Unknown
    exemplary connexin peptide

<400> SEQUENCE: 60

Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
            20                  25                  30

<210> SEQ ID NO 61
<211> LENGTH: 38
<212> TYPE: PRT
<213> ORGANISM: Unknown Organism
<220> FEATURE:
<223> OTHER INFORMATION: Description of Unknown Organism: Unknown
    exemplary connexin peptide

<400> SEQUENCE: 61

Gly Ala Leu His Tyr Phe Leu Phe Gly Phe Leu Ala Pro Lys Lys Phe
1               5                   10                  15

Pro Cys Thr Arg Pro Pro Cys Thr Gly Val Val Asp Cys Tyr Val Ser
            20                  25                  30

Arg Pro Thr Ser Lys Ser
            35

<210> SEQ ID NO 62
<211> LENGTH: 38
<212> TYPE: PRT
<213> ORGANISM: Unknown Organism
<220> FEATURE:
<223> OTHER INFORMATION: Description of Unknown Organism: Unknown
    exemplary connexin peptide

<400> SEQUENCE: 62

Leu Leu Ile Gln Trp Tyr Ile Tyr Gly Phe Ser Leu Ser Ala Val Tyr
1               5                   10                  15

Thr Cys Lys Arg Asp Pro Cys Pro His Gln Val Asp Cys Phe Leu Ser
            20                  25                  30

Arg Pro Thr Glu Lys Thr
            35

<210> SEQ ID NO 63
<211> LENGTH: 38
<212> TYPE: PRT
<213> ORGANISM: Unknown Organism -continued

```
<220> FEATURE:
<223> OTHER INFORMATION: Description of Unknown Organism: Unknown
      exemplary connexin peptide

<400> SEQUENCE: 63

Ile Ala Gly Gln Tyr Phe Leu Tyr Gly Phe Glu Leu Lys Pro Leu Tyr
1               5                   10                  15

Arg Cys Asp Arg Trp Pro Cys Pro Asn Thr Val Asp Cys Phe Ile Ser
            20                  25                  30

Arg Pro Thr Glu Lys Thr
        35

<210> SEQ ID NO 64
<211> LENGTH: 38
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 64

Leu Val Gly Gln Tyr Leu Leu Tyr Gly Phe Glu Val Arg Pro Phe Phe
1               5                   10                  15

Pro Cys Ser Arg Gln Pro Cys Pro His Val Val Asp Cys Phe Val Ser
            20                  25                  30

Arg Pro Thr Glu Lys Thr
        35

<210> SEQ ID NO 65
<211> LENGTH: 38
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 65

Ile Val Gly Gln Tyr Phe Ile Tyr Gly Ile Phe Leu Thr Thr Leu His
1               5                   10                  15

Val Cys Arg Arg Ser Pro Cys Pro His Pro Val Asn Cys Tyr Val Ser
            20                  25                  30

Arg Pro Thr Glu Lys Asn
        35

<210> SEQ ID NO 66
<211> LENGTH: 38
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 66

Leu Ile Gly Gln Tyr Phe Leu Tyr Gly Phe Gln Val His Pro Phe Tyr
1               5                   10                  15

Val Cys Ser Arg Leu Pro Cys His Pro Lys Ile Asp Cys Phe Ile Ser
            20                  25                  30

Arg Pro Thr Glu Lys Thr
        35

<210> SEQ ID NO 67
<211> LENGTH: 42
<212> TYPE: PRT
```

```
<213> ORGANISM: Unknown Organism
<220> FEATURE:
<223> OTHER INFORMATION: Description of Unknown Organism: Unknown
      exemplary connexin peptide

<400> SEQUENCE: 67

Leu Leu Ile Gln Trp Tyr Ile Tyr Gly Phe Ser Leu Ser Ala Val Tyr
1               5                   10                  15

Thr Cys Lys Arg Asp Pro Cys Pro His Gln Val Asp Cys Phe Leu Ser
                20                  25                  30

Arg Pro Thr Glu Lys Thr Ile Phe Ile Ile
                35                  40

<210> SEQ ID NO 68
<211> LENGTH: 43
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 68

Met Tyr Val Phe Tyr Val Met Tyr Asp Gly Phe Ser Met Gln Arg Leu
1               5                   10                  15

Val Lys Cys Asn Ala Trp Pro Cys Pro Asn Thr Val Asp Cys Phe Val
                20                  25                  30

Ser Arg Pro Thr Glu Lys Thr Val Phe Thr Val
                35                  40

<210> SEQ ID NO 69
<211> LENGTH: 42
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 69

Tyr Val Phe Tyr Phe Leu Tyr Asn Gly Tyr His Leu Pro Trp Val Leu
1               5                   10                  15

Lys Cys Gly Ile Asp Pro Cys Pro Asn Leu Val Asp Cys Phe Ile Ser
                20                  25                  30

Arg Pro Thr Glu Lys Thr Val Phe Thr Ile
                35                  40

<210> SEQ ID NO 70
<211> LENGTH: 43
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 70

Leu Tyr Ile Phe His Arg Leu Tyr Lys Asp Tyr Asp Met Pro Arg Val
1               5                   10                  15

Val Ala Cys Ser Val Glu Pro Cys Pro His Thr Val Asp Cys Tyr Ile
                20                  25                  30

Ser Arg Pro Thr Glu Lys Lys Val Phe Thr Tyr
                35                  40

<210> SEQ ID NO 71
<211> LENGTH: 42
```

```
-continued

<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 71

Leu Tyr Leu Leu His Thr Leu Trp His Gly Phe Asn Met Pro Arg Leu
1               5                   10                  15

Val Gln Cys Ala Asn Val Ala Pro Cys Pro Asn Ile Val Asp Cys Tyr
            20                  25                  30

Ile Ala Arg Pro Thr Glu Lys Lys Thr Tyr
        35                  40

<210> SEQ ID NO 72
<211> LENGTH: 43
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 72

Leu Tyr Val Phe His Ser Phe Tyr Pro Lys Tyr Ile Leu Pro Pro Val
1               5                   10                  15

Val Lys Cys His Ala Asp Pro Cys Pro Asn Ile Val Asp Cys Phe Ile
            20                  25                  30

Ser Lys Pro Ser Glu Lys Asn Ile Phe Thr Leu
        35                  40

<210> SEQ ID NO 73
<211> LENGTH: 43
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 73

Met Tyr Val Phe Tyr Leu Leu Tyr Pro Gly Tyr Ala Met Val Arg Leu
1               5                   10                  15

Val Lys Cys Asp Val Tyr Pro Cys Pro Asn Thr Val Asp Cys Phe Val
            20                  25                  30

Ser Arg Pro Thr Glu Lys Thr Val Phe Thr Val
        35                  40

<210> SEQ ID NO 74
<211> LENGTH: 36
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 74

Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
            20                  25                  30

Ile Phe Ile Ile
        35

<210> SEQ ID NO 75
```

```
<211> LENGTH: 36
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 75

Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
            20                  25                  30

Ile Phe Ile Ile
        35

<210> SEQ ID NO 76
<211> LENGTH: 42
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 76

Gly Ala Leu His Tyr Phe Leu Phe Gly Phe Leu Ala Pro Lys Lys Phe
1               5                   10                  15

Pro Cys Thr Arg Pro Pro Cys Thr Gly Val Val Asp Cys Tyr Val Ser
            20                  25                  30

Arg Pro Thr Glu Lys Ser Leu Leu Met Leu
            35                  40

<210> SEQ ID NO 77
<211> LENGTH: 42
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 77

Ile Ala Gly Gln Tyr Phe Leu Tyr Gly Phe Glu Leu Lys Pro Leu Tyr
1               5                   10                  15

Arg Cys Asp Arg Trp Pro Cys Pro Asn Thr Val Asp Cys Phe Ile Ser
            20                  25                  30

Arg Pro Thr Glu Lys Thr Ile Phe Ile Ile
            35                  40

<210> SEQ ID NO 78
<211> LENGTH: 42
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 78

Leu Val Gly Gln Tyr Leu Leu Tyr Gly Phe Glu Val Arg Pro Phe Phe
1               5                   10                  15

Pro Cys Ser Arg Gln Pro Cys Pro His Val Val Asp Cys Phe Val Ser
            20                  25                  30

Arg Pro Thr Glu Lys Thr Val Phe Leu Leu
            35                  40
```

```
<210> SEQ ID NO 79
<211> LENGTH: 41
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 79

Ile Val Gly Gln Tyr Phe Ile Tyr Gly Ile Phe Leu Thr Thr Leu His
1               5                   10                  15

Val Cys Arg Arg Ser Pro Cys Pro His Pro Val Asn Cys Tyr Ser Arg
                20                  25                  30

Pro Thr Glu Lys Asn Val Phe Ile Val
                35                  40

<210> SEQ ID NO 80
<211> LENGTH: 42
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 80

Leu Ile Gly Gln Tyr Phe Leu Tyr Gly Phe Gln Val His Pro Phe Tyr
1               5                   10                  15

Val Cys Ser Arg Leu Pro Cys His Pro Lys Ile Asp Cys Phe Ile Ser
                20                  25                  30

Arg Pro Thr Glu Lys Thr Ile Phe Leu Leu
                35                  40

<210> SEQ ID NO 81
<211> LENGTH: 45
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 81

Leu Gly Thr Ala Ala Glu Ser Ser Trp Gly Asp Glu Gln Ala Asp Phe
1               5                   10                  15

Arg Cys Asp Thr Ile Gln Pro Gly Cys Gln Asn Val Cys Thr Asp Gln
                20                  25                  30

Ala Phe Pro Ile Ser His Ile Arg Phe Trp Val Leu Gln
                35                  40                  45

<210> SEQ ID NO 82
<211> LENGTH: 14
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 82

Leu Gly Thr Ala Ala Glu Ser Ser Trp Gly Asp Glu Gln Ala
1               5                   10

<210> SEQ ID NO 83
<211> LENGTH: 13
<212> TYPE: PRT
<213> ORGANISM: Unknown Organism
<220> FEATURE:
```

```
<223> OTHER INFORMATION: Description of Unknown Organism: Unknown
      exemplary connexin peptide

<400> SEQUENCE: 83

Asp Glu Gln Ala Asp Phe Arg Cys Asp Thr Ile Gln Pro
1               5                   10

<210> SEQ ID NO 84
<211> LENGTH: 13
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 84

Thr Ile Gln Pro Gly Cys Gln Asn Val Cys Thr Asp Gln
1               5                   10

<210> SEQ ID NO 85
<211> LENGTH: 13
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 85

Val Cys Thr Asp Gln Ala Phe Pro Ile Ser His Ile Arg
1               5                   10

<210> SEQ ID NO 86
<211> LENGTH: 13
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 86

Ala Phe Pro Ile Ser His Ile Arg Phe Trp Val Leu Gln
1               5                   10

<210> SEQ ID NO 87
<211> LENGTH: 47
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 87

Met Glu Val Gly Phe Ile Val Gly Gln Tyr Phe Ile Tyr Gly Ile Phe
1               5                   10                  15

Leu Thr Thr Leu His Val Cys Arg Arg Ser Pro Cys Pro His Pro Val
            20                  25                  30

Asn Cys Tyr Val Ser Arg Pro Thr Glu Lys Asn Val Phe Ile Val
            35                  40                  45

<210> SEQ ID NO 88
<211> LENGTH: 11
<212> TYPE: PRT
<213> ORGANISM: Unknown Organism
<220> FEATURE:
<223> OTHER INFORMATION: Description of Unknown Organism: Unknown
      exemplary connexin peptide
```

```
<400> SEQUENCE: 88

Met Glu Val Gly Phe Ile Val Gly Gln Tyr Phe
1               5                   10

<210> SEQ ID NO 89
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 89

Ile Val Gly Gln Tyr Phe Ile Tyr Gly Ile Phe Leu
1               5                   10

<210> SEQ ID NO 90
<211> LENGTH: 14
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 90

Gly Ile Phe Leu Thr Thr Leu His Val Cys Arg Arg Ser Pro
1               5                   10

<210> SEQ ID NO 91
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 91

Arg Arg Ser Pro Cys Pro His Pro Val Asn Cys Tyr
1               5                   10

<210> SEQ ID NO 92
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 92

Val Asn Cys Tyr Val Ser Arg Pro Thr Glu Lys Asn
1               5                   10

<210> SEQ ID NO 93
<211> LENGTH: 11
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 93

Ser Arg Pro Thr Glu Lys Asn Val Phe Ile Val
1               5                   10

<210> SEQ ID NO 94
<211> LENGTH: 46
<212> TYPE: PRT
```

```
<213> ORGANISM: Unknown Organism
<220> FEATURE:
<223> OTHER INFORMATION: Description of Unknown Organism: Unknown
      exemplary connexin peptide

<400> SEQUENCE: 94

Leu Thr Ala Val Gly Gly Glu Ser Ile Tyr Tyr Asp Glu Gln Ser Lys
1               5                   10                  15

Phe Val Cys Asn Thr Glu Gln Pro Gly Cys Glu Asn Val Cys Tyr Asp
                20                  25                  30

Ala Phe Ala Pro Leu Ser His Val Arg Phe Trp Val Phe Gln
            35                  40                  45

<210> SEQ ID NO 95
<211> LENGTH: 15
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 95

Leu Thr Ala Val Gly Gly Glu Ser Ile Tyr Tyr Asp Glu Gln Ser
1               5                   10                  15

<210> SEQ ID NO 96
<211> LENGTH: 13
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 96

Asp Glu Gln Ser Lys Phe Val Cys Asn Thr Glu Gln Pro
1               5                   10

<210> SEQ ID NO 97
<211> LENGTH: 13
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 97

Thr Glu Gln Pro Gly Cys Glu Asn Val Cys Tyr Asp Ala
1               5                   10

<210> SEQ ID NO 98
<211> LENGTH: 13
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 98

Val Cys Tyr Asp Ala Phe Ala Pro Leu Ser His Val Arg
1               5                   10

<210> SEQ ID NO 99
<211> LENGTH: 12
<212> TYPE: PRT
<213> ORGANISM: Unknown Organism
<220> FEATURE:
<223> OTHER INFORMATION: Description of Unknown Organism: Unknown
``` exemplary connexin peptide

<400> SEQUENCE: 99

Ala Pro Leu Ser His Val Arg Phe Trp Val Phe Gln
1               5                   10

<210> SEQ ID NO 100
<211> LENGTH: 47
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 100

Phe Glu Val Gly Phe Leu Ile Gly Gln Tyr Phe Leu Tyr Gly Phe Gln
1               5                   10                  15

Val His Pro Phe Tyr Val Cys Ser Arg Leu Pro Cys His Pro Lys Ile
            20                  25                  30

Asp Cys Phe Ile Ser Arg Pro Thr Glu Lys Thr Ile Phe Leu Leu
        35                  40                  45

<210> SEQ ID NO 101
<211> LENGTH: 11
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 101

Phe Glu Val Gly Phe Leu Ile Gly Gln Tyr Phe
1               5                   10

<210> SEQ ID NO 102
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 102

Leu Ile Gly Gln Tyr Phe Leu Tyr Gly Phe Gln Val
1               5                   10

<210> SEQ ID NO 103
<211> LENGTH: 14
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 103

Gly Phe Gln Val His Pro Phe Tyr Val Cys Ser Arg Leu Pro
1               5                   10

<210> SEQ ID NO 104
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 104

```
Ser Arg Leu Pro Cys His Pro Lys Ile Asp Cys Phe
1               5                   10
```

<210> SEQ ID NO 105
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 105

```
Ile Asp Cys Phe Ile Ser Arg Pro Thr Glu Lys Thr
1               5                   10
```

<210> SEQ ID NO 106
<211> LENGTH: 11
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 106

```
Ser Arg Pro Thr Glu Lys Thr Ile Phe Leu Leu
1               5                   10
```

<210> SEQ ID NO 107
<211> LENGTH: 11
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 107

```
Ser Arg Gly Gly Glu Lys Asn Val Phe Ile Val
1               5                   10
```

<210> SEQ ID NO 108
<211> LENGTH: 10
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 108

```
Tyr Val Cys Ser Arg Leu Pro Cys His Pro
1               5                   10
```

<210> SEQ ID NO 109
<211> LENGTH: 11
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 109

```
Gln Val His Pro Phe Tyr Val Cys Ser Arg Leu
1               5                   10
```

<210> SEQ ID NO 110
<211> LENGTH: 13
<212> TYPE: PRT
<213> ORGANISM: Unknown Organism

```
<220> FEATURE:
<223> OTHER INFORMATION: Description of Unknown Organism: Unknown
      exemplary connexin peptide

<400> SEQUENCE: 110

Phe Glu Val Gly Phe Leu Ile Gly Gln Tyr Phe Leu Tyr
1               5                   10

<210> SEQ ID NO 111
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 111

Gly Gln Tyr Phe Leu Tyr Gly Phe Gln Val His Pro
1               5                   10

<210> SEQ ID NO 112
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 112

Gly Phe Gln Val His Pro Phe Tyr Val Cys Ser Arg
1               5                   10

<210> SEQ ID NO 113
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 113

Ala Val Gly Gly Glu Ser Ile Tyr Tyr Asp Glu Gln
1               5                   10

<210> SEQ ID NO 114
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 114

Tyr Asp Glu Gln Ser Lys Phe Val Cys Asn Thr Glu
1               5                   10

<210> SEQ ID NO 115
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 115

Asn Thr Glu Gln Pro Gly Cys Glu Asn Val Cys Tyr
1               5                   10
```

```
<210> SEQ ID NO 116
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 116

Cys Tyr Asp Ala Phe Ala Pro Leu Ser His Val Arg
1               5                   10

<210> SEQ ID NO 117
<211> LENGTH: 12
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 117

Phe Ala Pro Leu Ser His Val Arg Phe Trp Val Phe
1               5                   10

<210> SEQ ID NO 118
<211> LENGTH: 5
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 118

Leu Ile Gly Gln Tyr
1               5

<210> SEQ ID NO 119
<211> LENGTH: 5
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 119

Gln Val His Pro Phe
1               5

<210> SEQ ID NO 120
<211> LENGTH: 5
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 120

Tyr Val Cys Ser Arg
1               5

<210> SEQ ID NO 121
<211> LENGTH: 5
<212> TYPE: PRT
<213> ORGANISM: Unknown Organism
<220> FEATURE:
<223> OTHER INFORMATION: Description of Unknown Organism: Unknown
      exemplary connexin peptide
```

```
<400> SEQUENCE: 121

Ser Arg Leu Pro Cys
1               5

<210> SEQ ID NO 122
<211> LENGTH: 5
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 122

Leu Pro Cys His Pro
1               5

<210> SEQ ID NO 123
<211> LENGTH: 5
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 123

Gly Glu Ser Ile Tyr
1               5

<210> SEQ ID NO 124
<211> LENGTH: 6
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 124

Tyr Asp Glu Gln Ser Lys
1               5

<210> SEQ ID NO 125
<211> LENGTH: 6
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 125

Ser Lys Phe Val Cys Asn
1               5

<210> SEQ ID NO 126
<211> LENGTH: 8
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 126

Thr Glu Gln Pro Gly Cys Glu Asn
1               5

<210> SEQ ID NO 127
<211> LENGTH: 8
<212> TYPE: PRT
```

```
<213> ORGANISM: Unknown Organism
<220> FEATURE:
<223> OTHER INFORMATION: Description of Unknown Organism: Unknown
      exemplary connexin peptide

<400> SEQUENCE: 127

Val Cys Tyr Asp Ala Phe Ala Pro
1               5

<210> SEQ ID NO 128
<211> LENGTH: 10
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 128

Leu Ser His Val Arg Phe Trp Val Phe Gln
1               5                   10

<210> SEQ ID NO 129
<211> LENGTH: 14
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 129

Leu Ile Gln Tyr Phe Leu Tyr Gly Phe Gln Val His Pro Phe
1               5                   10

<210> SEQ ID NO 130
<211> LENGTH: 13
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 130

Val His Pro Phe Tyr Cys Ser Arg Leu Pro Cys His Pro
1               5                   10

<210> SEQ ID NO 131
<211> LENGTH: 22
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 131

Val Gly Gly Glu Ser Ile Tyr Tyr Asp Glu Gln Ser Lys Phe Val Cys
1               5                   10                  15

Asn Thr Glu Gln Pro Gly
            20

<210> SEQ ID NO 132
<211> LENGTH: 22
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 132
```

Thr Glu Gln Pro Gly Cys Glu Asn Val Cys Tyr Asp Ala Phe Ala Pro
1               5                   10                  15

Leu Ser His Val Arg Phe
            20

<210> SEQ ID NO 133
<211> LENGTH: 14
<212> TYPE: PRT
<213> ORGANISM: Unknown Organism
<220> FEATURE:
<223> OTHER INFORMATION: Description of Unknown Organism: Unknown
      exemplary connexin peptide

<400> SEQUENCE: 133

Ala Phe Ala Pro Leu Ser His Val Arg Phe Trp Val Phe Gln
1               5                   10

<210> SEQ ID NO 134
<211> LENGTH: 1314
<212> TYPE: DNA
<213> ORGANISM: Homo sapiens

<400> SEQUENCE: 134

```
ggcttttagc gtgaggaaag taccaaacag cagcggagtt ttaaacttta aatagacagg      60
tctgagtgcc tgaacttgcc ttttcatttt acttcatcct ccaaggagtt caatcacttg     120
gcgtgacttc actacttttta agcaaaagag tggtgcccag caacatggg tgactggagc    180
gccttaggca aactccttga caaggttcaa gcctactcaa ctgctggagg aaggtgtgg     240
ctgtcagtac ttttcatttt ccgaatcctg ctgctgggga cagcggttga gtcagcctgg   300
ggagatgagc agtctgcctt tcgttgtaac actcagcaac ctggttgtga aaatgtctgc    360
tatgacaagt ctttcccaat ctctcatgtg cgcttctggg tcctgcagat catatttgtg    420
tctgtaccca cactcttgta cctggctcat gtgttctatg tgatgcgaaa ggaagagaaa    480
ctgaacaaga aagaggaaga actcaaggtt gcccaaactg atggtgtcaa tgtggacatg    540
cacttgaagc agattgagat aaagaagttc aagtacggta ttgaagagca tggtaaggtg   600
aaaatgcgag gggggttgct gcgaacctac atcatcagta tcctcttcaa gtctatcttt    660
gaggtggcct tcttgctgat ccagtggtac atctatggat tcagcttgag tgctgtttac    720
acttgcaaaa gagatccctg cccacatcag gtggactgtt tcctctctcg ccccacggag   780
aaaaccatct tcatcatctt catgctggtg gtgtccttgg tgtccctggc cttgaatatc   840
attgaactct ctctatgttttt cttcaagggc gttaaggatc gggttaaggg aaagagcgac  900
ccttaccatg cgaccagtgg tgcgctgagc cctgccaaag actgtgggtc tcaaaaatat  960
gcttatttca atggctgctc ctcaccaacc gctcccctct cgcctatgtc tcctcctggg  1020
tacaagctgg ttactggcga cagaaacaat tcttcttgcc gcaattacaa caagcaagca  1080
agtgagcaaa actgggctaa ttacagtgca gaacaaaatc gaatgggca ggcgggaagc  1140
accatctcta actcccatgc acagcctttt gatttccccg atgataacca gaattctaaa  1200
aaactagctg ctggacatga attacagcca ctagccattg tggaccagcg accttcaagc  1260
agagccagca gtcgtgccag cagcagacct cggcctgatg acctggagat ctag         1314
```

<210> SEQ ID NO 135
<211> LENGTH: 1149
<212> TYPE: DNA
<213> ORGANISM: Homo sapiens

```
<400> SEQUENCE: 135
atgggtgact ggagcgcctt aggcaaactc cttgacaagg ttcaagccta ctcaactgct        60
ggagggaagg tgtggctgtc agtacttttc attttccgaa tcctgctgct ggggacagcg       120
gttgagtcag cctggggaga tgagcagtct gcctttcgtt gtaacactca gcaacctggt       180
tgtgaaaatg tctgctatga caagtctttc ccaatctctc atgtgcgctt ctgggtcctg       240
cagatcatat ttgtgtctgt acccacactc ttgtacctgg ctcatgtgtt ctatgtgatg       300
cgaaaggaag agaaactgaa caagaaagag gaagaactca aggttgccca aactgatggt       360
gtcaatgtgg acatgcactt gaagcagatt gagataaaga agttcaagta cggtattgaa       420
gagcatggta aggtgaaaat gcgagggggg ttgctgcgaa cctacatcat cagtatcctc       480
ttcaagtcta tctttgaggt ggccttcttg ctgatccagt ggtacatcta tggattcagc       540
ttgagtgctg tttacacttg caaaagagat ccctgcccac atcaggtgga ctgtttcctc       600
tctcgcccca cggagaaaac catcttcatc atcttcatgc tggtggtgtc cttggtgtcc       660
ctggccttga atatcattga actcttctat gttttcttca agggcgttaa ggatcgggtt       720
aagggaaaga gcgaccctta ccatgcgacc agtggtgcgc tgagccctgc caaagactgt       780
gggtctcaaa aatatgctta tttcaatggc tgctcctcac caaccgctcc cctctcgcct       840
atgtctcctc ctgggtacaa gctggttact ggcgacagaa acaattcttc ttgccgcaat       900
tacaacaagc aagcaagtga gcaaaactgg gctaattaca gtgcagaaca aaatcgaatg       960
gggcaggcgg gaagcaccat ctctaactcc catgcacagc cttttgattt ccccgatgat      1020
aaccagaatt ctaaaaaact agctgctgga catgaattac agccactagc cattgtggac      1080
cagcgacctt caagcagagc cagcagtcgt gccagcagca gacctcggcc tgatgacctg      1140
gagatctag                                                              1149
```

METHODS AND COMPOSITIONS FOR WOUND HEALING

RELATED APPLICATIONS

This application is a continuation of U.S. patent application Ser. No. 13/590,113 filed on Aug. 20, 2012 and will issue as U.S. Pat. No. 9,457,044 on Oct. 4, 2016, which is a continuation of and claims priority to U.S. patent application Ser. No. 11/985,717 filed on Nov. 15, 2007 and issued as U.S. Pat. No. 8,247,384 on Aug. 21, 2012, the entire contents of which is hereby incorporated by reference in its entirety, which claims the benefit of U.S. Provisional Application Ser. No. 60/859,437, filed on Nov. 15, 2006, the entire contents of which is hereby incorporated by reference in its entirety.

FIELD OF THE INVENTION

The field relates to wound-healing and tissue repair, and to connexins, connexin hemichannels and gap junctions, including compositions with one or more anti-connexin agents and one or more therapeutic agents, agents useful for wound healing, and/or gap junction modifying agents, articles and kits and delivery devices containing such compositions, and formulations comprising such compositions, as well as methods of treating wounds and diseases, disorders or conditions characterized in whole or in part by acute, delayed or incomplete wound healing or which would benefit from improved tissue repair or healing.

BACKGROUND AND INTRODUCTION TO THE INVENTION

The following includes information that may be useful in understanding the present inventions. It is not an admission that any of the information provided herein is prior art, or relevant, to the presently described or claimed inventions, or that any publication or document that is specifically or implicitly referenced is prior art.

In humans and other mammals wound injury triggers an organized complex cascade of cellular and biochemical events that will in most cases result in a healed wound. An ideally healed wound is one that restores normal anatomical structure, function, and appearance on cellular, tissue, organ, and organism levels. Wound healing, whether initiated by trauma, microbes or foreign materials, proceeds via a complex process encompassing a number of overlapping phases, including inflammation, epithelialization, angiogenesis and matrix deposition. Normally, these processes lead to a mature wound and a certain degree of scar formation. Although inflammation and repair mostly occur along a prescribed course, the sensitivity of the process is dependent on the balance of a variety of wound healing molecules, including for example, a network of regulatory cytokines and growth factors.

Gap junctions are cell membrane structures that facilitate direct cell-cell communication. A gap junction channel is formed of two connexons (hemichannels), each composed of six connexin subunits. Each hexameric connexon docks with a connexin in the opposing membrane to form a single gap junction. Gap junction channels are reported to be found throughout the body. Tissue such as the corneal epithelium, for example, has six to eight cell layers, yet expresses different gap junction channels in different layers with connexin 43 in the basal layer and connexin 26 from the basal to middle wing cell layers. In general, connexins are a family of proteins, commonly named according to their molecular weight or classified on a phylogenetic basis into alpha, beta, and gamma subclasses. At least 20 human and 19 murine isoforms have been identified. Different tissues and cell types are reported to have characteristic patterns of connexin protein expression and tissues have been shown to alter connexin protein expression pattern following injury or transplantation (Qui, C. et al., (2003) *Current Biology*, 13:1967-1703; Brander et al., (2004), *J. Invest Dermatol.* 122:1310-20).

Antisense technology has been proposed for the modulation of the expression for genes implicated in viral, fungal and metabolic diseases. See, for example, U.S. Pat. No. 5,166,195, (oligonucleotide inhibitors of HIV) and U.S. Pat. No. 5,004,810 (oligomers for hybridizing to herpes simplex virus Vmw65 mRNA and inhibiting replication). See also U.S. Pat. No. 7,098,190 issued to Becker and Green ("Formulations comprising antisense nucleotides to connexins"). Peptide inhibitors of gap junctions and hemichannels have also been reported. See for example Berthoud, V. M. et al., *Am J. Physiol. Lung Cell Mol. Physiol.* 279: L619-L622 (2000); Evans, W. H. and Boitano, S. *Biochem. Soc. Trans.* 29: 606-612, and De Vriese A. S., et al. *Kidney Int.* 61: 177-185 (2001). See also Becker and Green PCT/US06/04131 ("Anti-connexin compounds and uses thereof").

Various cytokines and growth factors have been investigated to determine their potential as therapeutic interventions in wound healing. Save platelet-derived growth factor, however, the active ingredient in Regranex®, none have been approved for sale in the United States. And, despite advances in the understanding of the principles underlying the wound healing process, there remains a significant unmet need for suitable therapeutic options for wound care and improving and/or promoting wound healing, including delayed or compromised wound healing such as chronic wounds, as well treatment of swelling, inflammation, and scarring associated with wounds, including acute and subacute wounds.

BRIEF SUMMARY

The inventions described and claimed herein have many attributes and embodiments including, but not limited to, those set forth or described or referenced in this Brief Summary. It is not intended to be all-inclusive and the inventions described and claimed herein are not limited to or by the features or embodiments identified in this Brief Summary, which is included for purposes of illustration only and not restriction.

The invention generally relates to the use of one or more anti-connexin agents (for example, connexin inhibitors such as alpha-1 connexin oligodeoxynucleotides and alpha-1 anti-connexin peptides or peptidomimetics) in combination with one or more therapeutic agents, agents useful for wound healing, and/or gap junction modifying agents for the treatment of wounds, including acute, subacute, delayed healing and chronic wounds.

The present invention provides for an increase in the rate, extent and/or quality of wound healing through the use of one or more anti-connexin agents and one or more therapeutic agents, agents useful for wound healing, and/or gap junction modifying agents. In a preferred embodiment, the combined use of one or more anti-connexin agents and one or more therapeutic agents, agents useful for wound healing, and/or gap junction modifying agents has an additive, synergistic or super-additive effect in the promotion of wound healing. In another preferred embodiment, the combined use of one or more anti-connexin agents and one or more therapeutic agents, agents useful for wound healing, and/or gap junction modifying agents allows the use of reduced doses of such agents compared to the dose or doses that may be effective when the agent is administered alone. In another preferred embodiment, the combined use of one or more anti-connexin agents and one or more therapeutic agents, agents useful for wound healing, and/or gap junction modifying agents allows a reduced frequency of administration compared to the frequency of administration when the agent is used alone.

Compositions and methods of the invention that employ anti-connexin agents in combination with other therapeutic agents, agents useful for wound healing, and/or gap junction modifying agents are disclosed and claimed.

The invention includes pharmaceutical compositions comprising (a) a therapeutically effective amount of an anti-connexin agent, and (b) a therapeutically effective amount of another therapeutic agent useful in the treatment of wounds or the promotion of wound-healing. The invention includes pharmaceutical compositions comprising (a) a therapeutically effective amount of an anti-connexin agent, and (b) a therapeutically effective amount of a gap junction modifying agent. Preferably, the pharmaceutical compositions further comprise a pharmaceutically acceptable carrier, diluent or excipient.

Pharmaceutical compositions are provided for combined, simultaneous, separate sequential or sustained administration. In one embodiment, a composition comprising one or more anti-connexin agents is administered at or about the same time as one ore more therapeutic agents, agents useful for wound healing, and/or gap junction modifying agents Pharmaceutical compositions are also provided in the form of a combined preparation, for example, as an admixture of one or more anti-connexin agents and one or more other agents useful for wound healing, e.g., growth factors that are effective in promoting or improving wound healing, such as platelet derived growth factor, epidermal growth factor, fibroblast growth factor (e.g., FGF2), vascular endothelial growth factor, and transforming growth factor β3, and/or cytokines that are effective in promoting or improving wound healing, such as IL-7 and IL-10, and/or other agents that are effective in promoting or improving wound healing, such as IGF (e.g., IGF-1) and IGFBP (e.g., IGFBP-2).

The term "a combined preparation" includes a "kit of parts" in the sense that the combination partners as defined above can be dosed independently or by use of different fixed combinations with distinguished amounts of the combination partners (a) and (b), i.e. simultaneously, separately or sequentially. The parts of the kit can then, for example, be administered simultaneously or chronologically staggered, that is at different time points and with equal or different time intervals for any part of the kit of parts.

In a preferred embodiment, the administration of a combined preparation will have fewer administration time points and/or increased time intervals between administrations as a result of such combined use.

In one aspect, the invention includes pharmaceutical compositions, including topical delivery forms and formulations, comprising a pharmaceutically acceptable carrier and therapeutically effective amounts of an anti-connexin agent and one or more agents described herein. Examples of anti-connexin agents include anti-connexin oligodeoxynucleotides ("ODN"), including antisense (including modified and unmodified backbone antisense), RNAi, and siRNA, as well as anti-connexin peptides and peptidomimetics. Suitable anti-connexin agents include for example, antisense ODNs, peptides and peptidomimetics against connexins 43, 26, 37, 30, and 31.1 and 32. In certain embodiments, suitable compositions include multiple anti-connexin agents in combination, including for example, connexin 43, 26, 30, and 31.1, together with one or more other agents useful in wound healing and/or tissue repair. Preferred anti-connexin agents are directed against connexin 43. Preferred agents for use in wound healing in combination with one or more anti-connexin agents include certain growth factors including, for example, platelet derived growth factor, epidermal growth factor, fibroblast growth factor alpha, fibroblast growth factor beta, vascular endothelial growth factor, and transforming growth factor β3, as well as insulin-like growth factor. Other preferred agents for use in wound healing in combination with one or more anti-connexin agents include certain cytokines including, for example IL-7 and IL-10. Other preferred agents for use in wound healing in combination with one or more anti-connexin agents include thymosin beta-4, secretory leukocyte protease inhibitor, beta adrenergic antagonists (e.g., timoptic), interleukin-1 receptor antagonists (e.g., anakinra), free radical scavengers (e.g., N-acetylcysteine), and gene therapy vectors comprising a coding sequence for a protein useful in the promotion or improvement of wound healing (e.g., an adenovirus vector including a sequence coding for platelet derived growth factor-B). Preferred therapeutic agents administered in combination with one or more anti-connexin agents include, for example anti-inflammatory agents, anti-microbial agents (e.g., trimethoprim), local and topical anesthetics, and topical opioids (e.g., morphine, hydromorphone and fentanyl).

In another aspect, the invention includes methods for administering a therapeutically effective amount of one or more pharmaceutically acceptable anti-connexin agent and one or more therapeutic agents, agents useful for wound healing and/or gap junction modifying agents formulated in a delayed release preparation, a slow release preparation, an extended release preparation, a controlled release preparation, and/or in a repeat action preparation to a subject with a wound, including wounds characterized in whole or in part by delayed or incomplete wound healing.

In certain other aspects, the invention also relates to methods of using such compositions to treat subjects suffering from or at risk for various diseases, disorders, and conditions associated with a wound, including acute and subacute wounds, and delayed healing or chronic wounds.

In yet another aspect, the invention includes methods for treating a subject having or suspected of having or predisposed to, or at risk for, any diseases, disorders and/or conditions characterized in whole or in part by a wound or a tissue in need of repair. Such compositions include, for example, topical delivery forms and formulations.

Preferred methods include the sequential or simultaneous administration of one or more anti-connexin agents and one or more agents useful for wound healing, either or both of which are provided in amounts or doses that are less that those used when the agent or agents are administered alone, i.e., when they are not administered in combination, either physically or in the course of treatment of a wound. Such lesser amounts of agents administered are typically from about one-twentieth to about one-tenth the amount or amounts of the agent when administered alone, and may be about one-eighth the amount, about one-sixth the amount, about one-fifth the amount, about one-fourth the amount, about one-third the amount, and about one-half the amount when administered alone. Preferably, the administration is sequential. Preferably, the agents are administered sequentially within at least about one-half hour of each other. The agents may also be administered with about one hour of each other, with about one day to about one week of each other, or as otherwise deemed appropriate. Preferably, the anti-connexin agent is administered first. Preferably, where one or more anti-connexin agents are used, an anti-connexin peptide or anti-connexin peptidomimetic, e.g., an anti-connexin agent that can block or reduce hemichannel opening, is administered prior to the administration of an anti-connexin agent that blocks or reduce connexin expression or the formation of hemichannels or gap junctions, e.g., by down-regulation of connexin protein expression. Preferably, the anti-connexin agent or agents is/are anti-connexin 43 agent(s).

In a further aspect, the invention includes transdermal patches, dressings, pads, wraps, matrices and bandages capable of being adhered or otherwise associated with the skin of a subject, said articles being capable of delivering a therapeutically effective amount of one or more pharmaceutically acceptable anti-connexin agents and one or more additional pharmaceutically acceptable therapeutics agents, agents useful for wound healing, and/or gap junction modifying agents to a subject.

In another aspect, the invention includes an article of manufacture comprising a vessel containing a therapeutically effective amount of one or more pharmaceutically acceptable anti-connexin agents and one or more pharmaceutically acceptable therapeutic agents for promotion of wound healing and instructions for use, including use for the treatment of a subject.

In another aspect, the invention includes an article of manufacture comprising a vessel containing a therapeutically effective amount of one or more pharmaceutically acceptable anti-connexin agents and one or more pharmaceutically acceptable agents useful for wound healing for promotion of wound healing and instructions for use, including use for the treatment of a subject.

In another aspect, the invention includes an article of manufacture comprising a vessel containing a therapeutically effective amount of one or more pharmaceutically acceptable anti-connexin agents and one or more pharmaceutically acceptable gap junction modifying agents and instructions for use, including use for the treatment of a subject.

The invention includes an article of manufacture comprising packaging material containing one or more dosage forms containing one or more pharmaceutically acceptable anti-connexin agents and one or more pharmaceutically acceptable therapeutic agents, agents useful for wound healing, and/or gap junction modifying agents, wherein the packaging material has a label that indicates that the dosage form can be used for a subject having or suspected of having or predisposed to any of the diseases, disorders and/or conditions described or referenced herein, including diseases, disorders and/or conditions characterized in whole or in part by acute, impaired, delayed or chronic wound healing. Such dosage forms include, for example, topical delivery forms and formulations.

The invention includes a formulation comprising a pharmaceutically acceptable anti-connexin agent and a pharmaceutically acceptable agent useful for wound healing in amounts effective to promote healing or tissue repair in a subject. The invention includes a formulation comprising a pharmaceutically acceptable anti-connexin agent and a pharmaceutically acceptable therapeutic agent in amounts effective to promote wound healing in a subject. The invention includes a formulation comprising a pharmaceutically acceptable anti-connexin agent and a pharmaceutically acceptable gap junction modifying agent in amounts effective to promote wound healing in a subject. Such formulations include, for example, topical delivery forms and formulations. Preferred formulations include one or more anti-connexin agents and one or more agents useful for wound healing, either or both of which are provided in amounts or doses that are less that those used when the agent or agents are administered alone, i.e., when they are not administered in combination, either physically or in the course of treatment of a wound. Such lesser amounts of agents administered or provided in combination are typically from about one-twentieth to about one-tenth the amount or amounts when administered alone, and may be about one-eighth the amount, about one-sixth the amount, about one-fifth the amount, about one-fourth the amount, about one-third the amount, and about one-half the amount when administered alone.

The invention includes methods for the use of therapeutically effective amounts of compositions comprising one or more pharmaceutically acceptable anti-connexin agents and one or more pharmaceutically acceptable therapeutic agents, agents useful for wound healing and/or gap junction modifying agents in the manufacture of a medicament. Such medicaments include, for example, topical delivery forms and formulations. Such medicaments include those for the treatment of a subject as disclosed herein. Such medicaments preferably include the reduced amounts of the one or more anti-connexin agents and the one or more pharmaceutically acceptable therapeutic agents, agents useful for wound healing and/or gap junction modifying agents, as noted herein.

The invention includes methods for the use of a therapeutically effective amount of one or more anti-connexin agents and one or more pharmaceutically acceptable therapeutic agents, agents useful for wound healing and/or gap junction modifying agents in the manufacture of a dosage form. Such dosage forms include, for example, topical delivery forms and formulations. Such dosage forms include those for the treatment of a subject as disclosed herein. Such dosage forms preferably include the reduced amounts of the one or more anti-connexin agents and the one or more pharmaceutically acceptable therapeutic agents, agents useful for wound healing and/or gap junction modifying agents, as noted herein.

In another aspect, the invention provides method of treatment comprising administering to a subject a pharmaceutical composition of the invention for use in the treatment of a wound, including for example, acute, subacute, delayed and chronic wounds.

In another aspect, the invention provides for the use of an anti-connexin agent (for example, anti-alpha-1 ODN, peptide or peptidomimetic) and a therapeutic agent, agent useful for wound healing, and/or gap junction modifying agent in the manufacture of a pharmaceutical product for the promotion of wound healing in a patient in need thereof.

In yet another aspect, the invention provides a method of promoting or enhancing wound healing or treatment, or the prevention or amelioration of fibrosis or other fibrotic conditions, the method comprising administering one or more anti-connexin agent and one or more therapeutic agents, agents useful for wound healing and/or gap junction modifying agents to a patient in need thereof.

In certain other aspect, the invention provides: (i) a package comprising an anti-connexin agent together with instructions for use in combination with a therapeutic agents, agents useful for wound healing and/or gap junction modifying agents for the promotion (e.g. decrease in healing time, better wound outcome) of wound healing, (ii) a package comprising one or more therapeutic agents, agents useful for wound healing and/or gap junction modifying agents together with instructions for use in combination with one or more anti-connexin agents for the promotion of wound healing; and (iii) a package comprising one or more anti-connexin agents and one or more therapeutic agents, agents useful for wound healing and/or gap junction modifying agents, together with instructions for use in the promotion of wound healing or reduction of wound-associated fibrosis.

In a one embodiment the pharmaceutical product of the invention is provided in combination with a wound dressing or wound healing promoting matrix. Suitably the wound dressing or matrix is provided including the form of a solid substrate with an anti-connexin agent and one or more therapeutic agents, agents useful for wound healing and/or gap junction modifying agents dispersed on or in the solid substrate.

The anti-connexin agent and therapeutic agents, agents useful for wound healing and/or gap junction modifying agents may be administered in the same composition or by separate compositions. Preferably, the agents are administered in the reduced amounts of the one or more anti-connexin agents and the one or more pharmaceutically acceptable therapeutic agents, agents useful for wound healing and/or gap junction modifying agents, as noted herein.

The anti-connexin agent and therapeutic agents, agents useful for wound healing and/or gap junction modifying agents may be administered to the patient simultaneously, sequentially or separately. If administered separately, preferably the anti-connexin agent and the therapeutic agent, agent useful for wound healing and/or gap junction modifying agent are administered sequentially. Preferably, the agents are administered sequentially within at least about one-half hour of each other. The agents may also be administered with about one hour of each other, with about one day to about one week of each other, or as otherwise deemed appropriate. Preferably, the anti-connexin agent is administered first. Preferably, where one or more anti-connexin agents are used, an anti-connexin peptide or anti-connexin peptidomimetic, e.g., an anti-connexin agent that can block or reduce hemichannel opening, is administered prior to the administration of an anti-connexin agent that blocks or reduce connexin expression or the formation of hemichannels or gap junctions, e.g., by downregulation of connexin protein expression. Preferably, the anti-connexin agent or agents is/are anti-connexin 43 agent(s).

These and other aspects of the present inventions, which are not limited to or by the information in this Brief Summary, are provided below.

BRIEF DESCRIPTION OF THE FIGURES

FIG. 1A to FIG. 1I depict expression of Cx43 at wound sites. FIG. 1A depicts Real-Time PCR analysis of the gene expression of Cx43 at wound sites. FIG. 1A depicts relative expression levels of Cx43 to GAPDH on days 1 and 7 in wounds treated with control sODN (n=4; open bars) and Cx43 asODN (n=4; filled bars); data are expressed as the mean±s.e.m. *P<0.05. FIGS. 1B to 1F depict Cx43 staining (green) with bis-benzimide nuclear staining (blue) of wounds treated with Cx43 asODN (FIG. 1B: 1 day, FIG. 1D: 2 days and FIG. 1F: 7 days) or controls (FIG. 1C: 1 day, FIG. 1E: 2 days and FIG. 1G: 7 days). FIGS. 1H and 1I depict illustration of sites imaged in the wound edge. (FIG. 1H) images B-E. (FIG. 1I) images F and G.

FIGS. 2A to 2D depict analysis of cell proliferation at wound sites by immunohistochemical staining with the anti-BrdU monoclonal antibody in control ODN (FIG. 2A: day 2 and FIG. 2C: day 7) and Cx43 asODN (FIG. 2B: day 2 and FIG. 2D: day 7). Arrowhead and arrow indicate the wound margin and leading edge, respectively. FIGS. 2E to 2H depict BrdU-stained cells; (i) and the number of BrdU-positive cells per field in the wound margin in the epidermis (FIG. 2E: n=5), and the nascent epidermis (FIG. 2F: n=5); (ii) the number of BrdU-positive cells in the dermal wound edge (FIG. 2G: n=5) and in the forming granulation tissue (FIG. 2H: n=5). Counts are expressed as the mean±s.e.m. *P<0.05. Scale bars represent 200 μm.

FIG. 3A and FIG. 3B depict neutrophil recruitment into skin wounds treated with control sODN (FIG. 3A) and Cx43 as ODN-treated (FIG. 3B), analyzed using an anti-MPO antibody on day 1. FIG. 3C depicts numbers of MPO positive cells at the wound site after treatment with control sODN (open bars: n=4 on day 1; n=5 on day 2) and Cx43 asODN (filled bars; n=3 on day 1; n=4 on day 2). Data are expressed as the mean±s.e.m. *P<0.05. Scale bars represent 50 μm.

FIG. 4A and FIG. 4B depict macrophage recruitment into skin wounds treated with control sODN (FIG. 4A) and Cx43 asODN (FIG. 4B), analyzed using an anti-F4/80 antibody on day 7. FIG. 4C depicts macrophage recruitment into skin wounds on days 2 and 7 after treatment with control sODN (open bars: n=4 on day 2; n=7 on day 7) and Cx43 asODN (filled bars: n=4 on day 2; n=6 on day 7). Data are expressed as the mean±s.e.m. *P<0.01. Scale bars represent 50

FIG. 5A and FIG. 5B depict Real-Time PCR analysis of the gene expression of Ccl2 and TNF-α at wound sites. Relative expression levels of Ccl2 (FIG. 5A) and TNF-α (FIG. 5B) to GAPDH on days 1, 2 and 7 (n=5 for each) after treatment with control sODN (open bars) or Cx43 asODN (filled bars) are quantified. Data are expressed as the mean±s.e.m. *P<0.05.

FIG. 6A to FIG. 6K depict expression of TGF-β1. FIGS. 6A to 6J depict immunohistochemistry for TGF-β1 at wound sites treated with control sODN (FIGS. 6A-6E) and with Cx43 asODN (FIGS. 6F-6J). Scale bars represent 200 μm (FIGS. 6A and 6F) and 50 μm (FIGS. 6B-6E, and 6G-6J). Black arrows show the nascent edge of the epidermis. TGF-β1 staining is considerably stronger in the epidermis of Cx43 asODN treated wounds (FIGS. 6I and 6J) compared to control sODN (FIGS. 6D and 6E) wounds. Arrowheads, red and black show representative TGF-β1 elongated fibroblast-like cells and rounded presumptive leukocytes, respectively. FIG. 6K depicts Real-Time PCR analysis of the expression on days 1, 2 and 7 (n=5 for each) of mRNA for TGF-β1 at wound sites treated with control sODN (open bars) or Cx43 asODN (filled bars). Data are expressed as the mean±s.e.m. *P<0.05.

FIG. 7A to FIG. 7F depict granulation tissue formation and fibroblast migration. FIGS. 7A and 7B depict fibroblast-like cell recruitment into skin wounds treated with control sODN (FIG. 7A) and Cx43 asODN (FIG. 7B), analyzed using TRITC-Phalloidin and DAPI nuclear staining on day 2. FIG. 7C depicts numbers of fibroblast-like cells at each wound site per field of view for wounds treated with control sODN (open bars: n=5) or Cx43 asODN (filled bars: n=5). FIG. 7D depicts results of a wound-healing assay of fibroblast migration that shows that migration is significantly faster after treatment with Cx43 as ODNs. FIGS. 7E and 7F depict images of wounds in fibroblast cultures; at the time of wounding (FIG. 7E) and 4 hours after wounding (FIG. 7F). Data are expressed as the mean±s.e.m. *P<0.02 **P<0.01. Scale bars represent 50 μm.

FIG. 8A depicts collagen content assessed by quantitatively measuring the hydroxyproline (HP) content on days 7, 10 and 14 after wounding at wound sites treated with control sODN (open bars) and Cx43 asODN (filled bars) and in uninjured skin (n=5). Data are expressed as the mean±s.e.m. P<0.05. FIG. 8B depicts Real-Time PCR analysis of the expression of mRNA on days 1, 2 and 7 (n=5 for each) for Col1α1 at wound sites treated with control sODN (open bars) and Cx43 asODN (filled bars). Data are expressed as the mean±s.e.m. *P<0.05.

FIGS. 9A and 9B depict H&E staining of 14 days wound granulation tissue in control sODN treated (FIG. 9A) and asODN treated (FIG. 9B) wounds. FIG. 9C depicts an area of granulation tissue after treatment with control sODN (open bars) or Cx43 asODN (filled bars) analyzed on day 5 (control; n=7, asODN; n=6), day 7 (control; n=5, asODN; n=5), day 10 (control; n=5, asODN; n=6), and day 14 (control; n=5, asODN; n=6). Granulation tissue area measurements at day 5 already showed a slightly smaller area after treatment with asODN but the reduction became significant on days 7, 10 and 14 (*P<0.05. **P<0.01). Data are expressed as the mean±s.e.m. Scale bars represents 1 mm.

FIGS. 10A and 10B depict TUNEL staining of granulation tissue in control sODN (FIG. 10A) and Cx43 asODN (FIG. 10B) treated wounds on day 7. Apoptotic cells appear as bright green spots, some of which have been highlighted with arrowheads. Scale bars represents 50 μm. FIG. 10C depicts numbers of apoptotic cells per field of view on days 5, 7 and 10 (n=6 for each) in wound sites treated with control sODN (open bars) and Cx43 asODN (filed bars). Data are expressed as the mean±s.e.m. Scale bars represent 50 μm.

FIG. 11A to FIG. 11F depict myofibroblast maturation at wound sites. FIGS. 11A and 11D depict anti-α smooth muscle actin (SMA) staining (green) with bis-benzimide nuclear staining (blue) of the edge of the granulation tissue in a 7 day wound (FIGS. 11A and 11B) and the center of the granulation tissue in a 10 day wound (FIGS. 11C and 11D). FIG. 11E depicts quantification of staining levels showed there to be significantly more SMA staining in Cx43 asODN treated wounds than controls at 7 days (P=0.004) indicating earlier maturation and differentiation of myofibroblasts. This more advanced maturation was still present at 10 days when most of the SMA staining and myofibroblasts were lost in Cx43 asODN-treated wounds, but staining was still very strong in control wounds (P=0.000002). FIG. 11F depicts illustration of sites imaged in the granulation tissue: zone I (FIGS. 11A and 11B) and zone II (FIGS. 11C and 11D). Data are expressed as the mean±s.e.m. Scale bars represent 25 μm.

FIGS. 12A to 12F depict von Willebrand factor staining of granulation tissue nacent blood vessels (green) with bis-benzimide nuclear stain (blue) at 7 days, (FIGS. 12A and 12B) 10 days, (FIGS. 12C and 12D) and 14 days (FIGS. 12E and 12F) after wounding. In antisense-treated wounds (FIGS. 12A, 12C and 12E) blood vessels were more pervasive at early time points (7 days FIGS. 12A and 12B and 10 days FIGS. 12C and 12D) but considerably finer than those treated with control ODN (FIGS. 12B, 12D, and 12F) resulting in significantly reduced staining compared to controls (7 days *P=0.0019; 10 days **P=0.015). By 14 days, blood vessels had increased in size in the asODN group and were a similar size to those of controls (FIG. 12G). FIG. 12H depicts illustration of sites imaged in the granulation tissue: zone I (FIGS. 12A and 12B) and zone II (FIGS. 12C to 12E). Data are expressed as the mean±s. e. m. Scale bars represent 25 μm.

FIG. 13A to FIG. 13B depict macroscopic images of wound healing (FIG. 13A) and relative changes in the wound area (FIG. 13B) following As ODN treatment as compared with control treatment.

DETAILED DESCRIPTION

Definitions

Figure 2A:
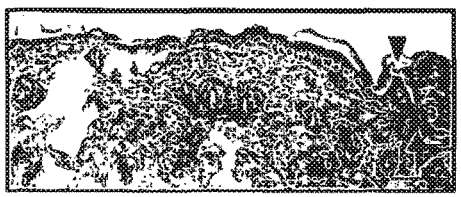
FIG. 2A to FIG. 2H depict cell proliferation after wounding.
Figure 2B:
Figure 2C:
Figure 2D:
Figure 2E:
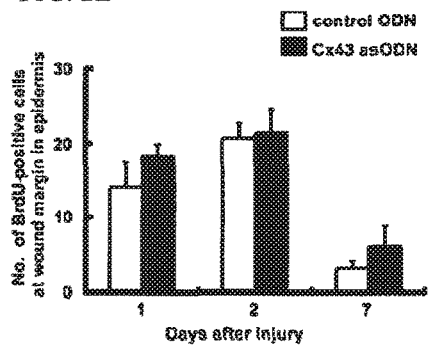

As used herein, a "disorder" is any disorder, disease, or condition that would benefit from an agent that promotes wound healing and/or reduces swelling, inflammation, and/or scar formation. For example, included are wounds resulting from surgery or trauma, and wound associated abnormalities in connection with neuropathic, ischemic, microvascular pathology, pressure over bony area (tailbone (sacral), hip (trochanteric), buttocks (ischial), or heel of the foot), reperfusion injury, and valve reflux etiology and conditions.

As used herein, "subject" refers to any mammal, including humans, domestic and farm animals, and zoo, sports, or pet animals, such as dogs, horses, cats, sheep, pigs, cows, etc. The preferred mammal herein is a human, including adults, children, and the elderly.

As used herein, "preventing" means preventing in whole or in part, or ameliorating or controlling.

As used herein, a "therapeutically effective amount" in reference to the compounds or compositions of the instant invention refers to the amount sufficient to induce a desired biological, pharmaceutical, or therapeutic result. That result can be alleviation of the signs, symptoms, or causes of a disease or disorder or condition, or any other desired alteration of a biological system. In the present invention, the result will involve the promotion of wound healing and decreases in swelling, inflammation and/or scar formation in whole or in part.

As used herein, the term "treating" refers to both therapeutic treatment and prophylactic or preventative measures. Those in need of treatment include those already with a wound or other related disorder as well as those prone to having a wound or related disorder or diagnosed with the disorder or those in which the disorder is to be prevented.

As used herein, "anti-connexin agents" are compounds that affect or modulate the activity, expression or formation of a connexin, a connexin hemichannel (connexon), or a gap junction. Anti-connexin agents include, without limitation, antisense compounds (e.g. antisense polynucleotides), RNAi and siRNA compounds, antibodies and binding fragments thereof, and peptides and polypeptides, which include "peptidomimetics," and peptide analogs. Preferred anti-connexin agents are anti-connexin 43 agents. Exemplary anit-connexin agents are discussed in further detail herein.

As used herein, the term "treating" refers to both therapeutic treatment and prophylactic or preventative measures. Those in need of treatment include those already with the disorder as well as those prone to having the disorder or diagnosed with the disorder or those in which the disorder is to be prevented.

The terms "peptidomimetic" and "mimetic" include naturally occurring and synthetic chemical compounds that may have substantially the same structural and functional characteristics of protein regions which they mimic. In the case of connexins, these may mimic, for example, the extracellular loops of opposing connexins involved in connexon-connexon docking and cell-cell channel formation.

"Peptide analogs" refer to the compounds with properties analogous to those of the template peptide and may be non-peptide drugs. "Peptidomimetics" (also known as "mimetic peptides"), which include peptide-based compounds, also include such non-peptide based compounds such as peptide analogs. Peptidomimetics that are structurally similar to therapeutically useful peptides may be used to produce an equivalent or enhanced therapeutic or prophylactic effect. Generally, peptidomimetics are structurally identical or similar to a paradigm polypeptide (i.e., a polypeptide that has a biological or pharmacological function or activity), but can also have one or more peptide linkages optionally replaced by a linkage selected from the group consisting of, for example, —CH2NH—, —CH2S—, —CH2-CH2-, —CH═CH— (cis and trans), —COCH2-, —CH(OH)CH2-, and —CH2SO—. The mimetic can be either entirely composed of natural amino acids, or non-natural analogues of amino acids, or, is a chimeric molecule of partly natural peptide amino acids and partly non-natural analogs of amino acids. The mimetic can also comprise any amount of natural amino acid conservative substitutions as long as such substitutions also do not substantially alter mimetic activity. For example, a mimetic composition may be useful as an anti-connexin agent if it is capable of down-regulating biological actions or activities of connexins proteins or connexons, such as, for example, preventing the docking of connexons to form gap-junction-mediated cell-cell communications, or preventing the opening connexons to expose the cell cytoplasm to the extracellular millieu. Peptidomimetics, mimetic peptides, and connexin modulating peptides encompass those described such peptidomimetics, mimetic peptides, and connexin modulating peptides set forth herein, as well as those as may be known in the art, whether now known or later developed.

The terms "modulator" and "modulation" of connexin activity, as used herein in its various forms, refers to inhibition in whole or in part of the expression or action or activity of a connexin or connexin hemichannel and may function as anti-connexin agents.

In general, the term "protein" refers to any polymer of two or more individual amino acids (whether or not naturally occurring) linked via peptide bonds, as occur when the carboxyl carbon atom of the carboxylic acid group bonded to the alpha-carbon of one amino acid (or amino acid residue) becomes covalently bound to the amino nitrogen atom of the amino group bonded to the alpha-carbon of an adjacent amino acid. These peptide bond linkages, and the atoms comprising them (i.e., alpha-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide" (which, at times, may be used interchangeably herein). Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. A "domain" of a protein is also a fragment, and comprises the amino acid residues of the protein often required to confer activity or function.

As used herein, "simultaneously" is used to mean that the one or more agents of the invention are administered concurrently, whereas the term "in combination" is used to mean they are administered, if not simultaneously or in physical combination, then "sequentially" within a timeframe that they both are available to act therapeutically. Thus, administration "sequentially" may permit one agent to be administered within minutes (for example, 1, 2, 3, 4, 5, 10, 15, 20, 25, 30) minutes or a matter of hours, days, weeks or months after the other provided that both the one or more anti-connexin agents and one or more therapeutic agents, agents useful for wound healing, and/or gap junction modifying agents are concurrently present in effective amounts. The time delay between administration or administrations of the components will vary depending on the exact nature of the components, the interaction there between, and their respective half-lives.

By "wound" is meant an injury to any tissue, including for example, acute, subacute, delayed or difficult to heal wounds, and chronic wounds. Examples of wounds may include both open and closed wounds. Wounds include, for example, burns, incisions, excisions, lacerations, abrasions, puncture or penetrating wounds, surgical wounds, contusions, hematomas, crushing injuries, and ulcers.

As described herein, a delayed or difficult to heal wound may include, for example, a wound that is characterized at least in part by one or more of 1) a prolonged inflammatory phase, 2) a slow forming extracellular matrix (ECM), and 3) a stalled or decreased rate of epithelialization.

As used herein, chronic wound may refer to, for example, a wound that is characterized at least in part by one or more of 1) a chronic self-perpetuating state of wound inflammation, 2) a deficient and defective wound ECM, 3) poorly responding (senescent) wound cells especially fibroblasts, limiting ECM production, and 4) failure of re-epithelialization due in part to lack of the necessary ECM orchestration and lack of scaffold for migration. Chronic wounds include venous ulcers, arterial ulcers, pressure ulcers, vasculitic ulcers, and diabetic ulcers.

The term "dressing" refers to a dressing for topical application to a wound and excludes compositions suitable for systemic administration. For example, the one or more anti-connexin agents and or the one or more agents useful for wound healing, therapeutic agents, and/or gap junction modifying agents may be dispersed in or on a solid sheet of wound contacting material such as a woven or nonwoven textile material, or may be dispersed in a layer of foam such as polyurethane foam, or in a hydrogel such as a polyurethane hydrogel, a polyacrylate hydrogel, gelatin, carboxymethyl cellulose, pectin, alginate, and/or hyaluronic acid hydrogel, for example in a gel or ointment. In certain embodiments the anti-connexin agent and/or said one or more agents useful for wound healing, therapeutic agents, and/or gap junction modifying agents are dispersed in or on a biodegradable sheet material that provides sustained release of the active ingredients into the wound, for example a sheet of freeze-dried collagen, freeze-dried collagen/alginate mixtures (available under the Registered Trade Mark FIBRACOL from Johnson & Johnson Medical Limited) or freeze-dried collagen/oxidized regenerated cellulose (available under the Registered Trade Mark PROMOGRAN from Johnson & Johnson Medical Limited).

As used herein, "matrix" includes for example, matrices such as collagen, acellular matrix, crosslinked biological scaffold molecules, tissue based bioengineered structural framework, biomanufactured bioprostheses, and other implanted structures such as for example, vascular grafts suitable for cell infiltration and proliferation useful in the promotion of wound healing. Additional suitable biomatrix material may include chemically modified collagenous tissue to reduce antigenicity and immunogenicity. Other suitable examples include collagen sheets for wound dressings, antigen-free or antigen reduced acellular matrix (Wilson et al., *Trans Am Soc Artif Intern* 1990; 36:340-343) or other biomatrix which have been engineered to reduce the antigenic response to the xenograft material. Other matrix useful in promotion of wound healing may include for example, processed bovine pericardium proteins comprising insoluble collagen and elastin (Courtman et al., *J Biomed Mater Res* 1994; 28:655-666) and other acellular tissue which may be useful for providing a natural microenvironment for host cell migration to accelerate tissue regeneration (Malone et al., *J Vasc Surg* 1984; 1:181-91). In certain embodiments, the matrix material may be supplemented with agents useful for wound healing such as growth factors or other wound healing promoting agents for site specific release, therapeutic agents, and/or gap junction modifying agents.

Wounds and Wound Classification

In addition to the definition previously provided, the term "wound" may also include for example, injuries to the skin and subcutaneous tissue initiated in different ways (e.g., pressure sores from extended bed rest and wounds induced by trauma) and with varying characteristics. Wounds may be classified into one of four grades depending on the depth of the wound: i) Grade I: wounds limited to the epithelium; ii) Grade II: wounds extending into the dermis; iii) Grade III: wounds extending into the subcutaneous tissue; and iv) Grade IV (or full-thickness wounds): wounds wherein bones are exposed (e.g., a bony pressure point such as the greater trochanter or the sacrum). The term "partial thickness wound" refers to wounds that encompass Grades I-III; examples of partial thickness wounds include burn wounds, pressure sores, venous stasis ulcers, and diabetic ulcers. The term "deep wound" is meant to include both Grade III and Grade IV wounds. The compositions and methods of the present invention contemplate treating all wound types, including deep wounds and chronic wounds. The term "chronic wound" refers to a wound that has not healed. Preferably, it is selected from the group consisting of venous ulcers, pressure sores, vasculitic ulcers, diabetic ulcers and decubitus ulcers. Chronic skin wounds include, for example, pressure ulcers, diabetic ulcers, venous ulcers, vasculitic ulcers, arterial ulcers, and mixed ulcers. The chronic wound may be an arterial ulcer which comprises ulcerations resulting from complete or partial arterial blockage. The chronic wound may be a venous stasis ulcer which comprises ulcerations resulting from a malfunction of the venous valve and the associated vascular disease. The chronic wound may be a trauma-induced ulcer, a diabetic ulcer, or a vasculitic ulcer.

Pressure Ulcer:

Pressure ulcers may be classified into 4 stages based on AHCPR (Agency for Health Care Policy and Research, U.S. Department of Health and Human Services) guidelines: Stage 1: A stage I pressure ulcer is an observable pressure related alteration of intact skin whose indicators as compared to the adjacent or opposite area on the body may include changes in one or more of the following: skin temperature (warmth or coolness), tissue consistency (firm or boggy feel) and/or sensation (pain, itching). The ulcer appears as a defined area of persistent redness in lightly pigmented skin, whereas in darker skin tones, the ulcer may appear with persistent red, blue, or purple hues. Stage 1 ulceration may include nonblanchable erythema of intact skin and the heralding lesion of skin ulceration. In individuals with darker skin, discoloration of the skin, warmth, edema, induration, or hardness may also be indicators of stage 1 ulceration. Stage 2: stage 2 ulceration may be characterized by partial thickness skin loss involving epidermis, dermis, or both. The ulcer is superficial and presents clinically as an abrasion, blister, or shallow crater. Stage 3: stage 3 ulceration may be characterized by full thickness skin loss involving damage to or necrosis of subcutaneous tissue that may extend down to, but not through, underlying fascia. The ulcer presents clinically as a deep crater with or without undermining of adjacent tissue. Stage 4: stage 4 ulceration may be characterized by full thickness skin loss with extensive destruction, tissue necrosis, or damage to muscle, bone, or supporting structures (e.g., tendon, joint capsule). In certain embodiments compositions and methods of treating a chronic wound are provided where the chronic wound is characterized by one or more of the following AHCPR stages of pressure ulceration: stage 1, stage 2, stage 3, and/or stage 4.

Decubitus Ulcers:

Decubitus ulcer may arise as a result of prolonged and unrelieved pressure over a bony prominence that leads to ischemia. The wound tends to occur in patients who are unable to reposition themselves to off-load weight, such as paralyzed, unconscious, or severely debilitated persons. As defined by the U.S. Department of Health and Human Services, the major preventive measures include identification of high-risk patients; frequent assessment; and prophylactic measures such as scheduled repositioning, appropriate pressure-relief bedding, moisture barriers, and adequate nutritional status. Treatment options may include for example, pressure relief, surgical and enzymatic debridement, moist wound care, and control of the bacterial load. In certain embodiments compositions and methods of treating a chronic wound are provided wherein the chronic wound is characterized by decubitus ulcer or ulceration which results from prolonged, unrelieved pressure over a bony prominence that leads to ischemia.

Arterial Ulcers:

Arterial ulcers may be characterized by complete or partial arterial blockage which may lead to tissue necrosis and/or ulceration. Signs of arterial ulcer may include, for example, pulselessness of the extremity; painful ulceration; small, punctate ulcers that are usually well circumscribed; cool or cold skin; delayed capillary return time (briefly push on the end of the toe and release, normal color should return to the toe in about 3 seconds or less); atrophic appearing skin (for example, shiny, thin, dry); and loss of digital and pedal hair. In certain embodiments compositions and methods of treating a chronic wound are provided wherein the chronic wound is characterized by arterial ulcers or ulcerations due to complete or partial arterial blockage.

Venous Ulcers:

Venous ulcers are the most common type of ulcer affecting the lower extremities and may be characterized by malfunction of the venous valve. The normal vein has valves that prevent the backflow of blood. When these valves become incompetent, the backflow of venous blood causes venous congestion. Hemoglobin from the red blood cells escapes and leaks into the extravascular space, causing the brownish discoloration commonly noted. It has been shown that the transcutaneous oxygen pressure of the skin surrounding a venous ulcer is decreased, suggesting that there are forces obstructing the normal vascularity of the area. Lymphatic drainage and flow also plays a role in these ulcers. The venous ulcer may appear near the medial malleolus and usually occurs in combination with an edematous and indurated lower extremity; it may be shallow, not too painful and may present with a weeping discharge from the affected site. In certain embodiments compositions and methods of treating a chronic wound are provided wherein the chronic wound is characterized by venous ulcers or ulcerations due to malfunction of the venous valve and the associated vascular disease.

Venous Stasis Ulcers:

Venous stasis ulcer may be characterized by chronic passive venous congestion of the lower extremities results in local hypoxia. One possible mechanism of pathogenesis of these wounds includes the impediment of oxygen diffusion into the tissue across thick perivascular fibrin cuffs. Another mechanism is that macromolecules leaking into the perivascular tissue trap growth factors needed for the maintenance of skin integrity. Additionally, the flow of large white blood cells slows due to venous congestion, occluding capillaries, becoming activated, and damaging the vascular endothelium to predispose to ulcer formation. Thus, in certain embodiments compositions and method of treating a chronic wound are provided wherein the chronic wound is characterized by venous stasis ulcers or ulcerations due to chronic passive venous congestion of the lower extremities and/or the resulting local hypoxia.

Diabetic Ulcers:

Diabetic patients are prone to foot and other ulcerations due to both neurologic and vascular complications. Peripheral neuropathy can cause altered or complete loss of sensation in the foot and/or leg. Diabetic patients with advanced neuropathy looses all ability for sharp-dull discrimination. Any cuts or trauma to the foot may go completely unnoticed for days or weeks in a patient with neuropathy. A patient with advanced neuropathy looses the ability to sense a sustained pressure insult, as a result, tissue ischemia and necrosis may occur leading to for example, plantar ulcerations. Microvascular disease is one of the significant complication for diabetics which may also lead to ulcerations. In certain embodiments compositions and methods of treating a chronic wound are provided wherein the chronic wound is characterized by diabetic foot ulcers and/or ulcerations due to neurologic and/or vascular complications of diabetes.

Traumatic Ulcers:

Formation of traumatic ulcers may occur as a result of traumatic injuries to the body. These injuries include, for example, compromises to the arterial, venous or lymphatic systems; changes to the bony architecture of the skeleton; loss of tissue layers—epidermis, dermis, subcutaneous soft tissue, muscle or bone; damage to body parts or organs and loss of body parts or organs. In certain embodiments, compositions and methods of treating a chronic wound are provided wherein the chronic wound is characterized by ulcerations associated with traumatic injuries to the body.

Burn Ulcers:

Ulceration may also occur as a result of a burn injury, including 1st degree burn (i.e., superficial, reddened area of skin); 2nd degree burn (a blistered injury site which may heal spontaneously after the blister fluid has been removed); 3rd degree burn (burn through the entire skin and usually require surgical intervention for wound healing); scalding (may occur from scalding hot water, grease or radiator fluid); thermal (may occur from flames, usually deep burns); chemical (may come from acid and alkali, usually deep burns); electrical (either low voltage around a house or high voltage at work); explosion flash (usually superficial injuries); and contact burns (usually deep and may occur from muffler tail pipes, hot irons and stoves). In certain embodiments, compositions and methods of treating a chronic wound are provided wherein the chronic wound is characterized by ulcerations associated with burn injuries to the body.

Anti-Connexin Agents

Anti-connexin agents of the invention described herein are capable of modulating or affecting the transport of molecules into and out of cells (e.g., blocking or inhibiting or downregulating). Thus certain anti-connexin agents described herein modulate cellular communication (e.g., cell to cell). Certain anti-connexin agents modulate or effect transmission of molecules between the cell cytoplasm and the periplasmic or extracellular space. Such anti-connexin agents are generally targeted to connexins and/or connexin hemichannels (connexons). Hemichannels and resulting gap junctions that comprise connexins are independently involved in the release or exchange of small molecules between the cell cytoplasm and an extracellular space or tissue in the case of open hemichannels, and between the cytoplasm of adjoining cell in the case of open gap junctions. Thus, an anti-connexin agents provided herein may directly or indirectly reduce coupling and communication between cells or reduce or block communication (or the transmission of molecules) between a cell and extracellular space or tissue, and the modulation of transport of molecules from a cell into an extracellular space or tissue (or from an extracellular space or tissue into a cell) or between adjoining cells is within the scope of anti-connexin agents and embodiments of the invention.

Any anti-connexin agent that is capable of eliciting a desired inhibition of the passage (e.g. transport) of molecules through a gap junction or connexin hemichannel may be used in embodiments of the invention. Any anti-connexin agents that modulates the passage of molecules through a gap junction or connexin hemichannel are also provided in particular embodiments (e.g., those that modulate, block or lessen the passage of molecules from the cytoplasm of a cell into an extracellular space or adjoining cell cytoplasm). Such anti-connexin agents may modulate the passage of molecules through a gap junction or connexin hemichannel with or without gap junction uncoupling (blocking the transport of molecules through gap junctions). Such compounds include, for example, proteins and polypeptides, polynucleotides, and other organic compounds, and they may, for example block the function or expression of a gap junction or a hemichannel in whole or in part, or downregulate the production of a connexin in whole or in part. Certain gap junction inhibitors are listed in Evans, W. H. and Boitano, S. *Biochem. Soc. Trans*. 29: 606-612 (2001).

Certain anti-connexin agents provide downregulation of connexin expression (for example, by downregulation of mRNA transcription or translation) or otherwise decrease or inhibit the activity of a connexin protein, a connexin hemichannel or a gap junction. In the case of downregulation, this will have the effect of reducing direct cell-cell communication by gap junctions, or exposure of cell cytoplasm to the extracellular space by hemichannels, at the site at which connexin expression is downregulated.

Examples of anti-connexin agents include agents that decrease or inhibit expression or function of connexin mRNA and/or protein or that decrease activity, expression or formation of a connexin, a connexin hemichannel or a gap junction. Anti-connexin agents include anti-connexin polynucleotides, such as antisense polynucleotides and other polynucleotides (such as polynucleotides having siRNA or ribozyme functionalities), as well as antibodies and binding fragments thereof, and peptides and polypeptides, including peptidomimetics and peptide analogs that modulate hemichannel or gap junction activity or function.

Anti-Connexin Polynucleotides

Anti-connexin polynucleotides include connexin antisense polynucleotides as well as polynucleotides which have functionalities which enable them to downregulate connexin expression. Other suitable anti-connexin polynucleotides include RNAi polynucleotides and siRNA polynucleotides.

Synthesis of antisense polynucleotides and other anti-connexin polynucleotides such as RNAi, siRNA, and ribozyme polynucleotides as well as polynucleotides having modified and mixed backbones is known to those of skill in the art. See e.g. Stein C. A. and Krieg A. M. (eds), Applied Antisense Oligonucleotide Technology, 1998 (Wiley-Liss). Methods of synthesizing antibodies and binding fragments as well as peptides and polypeptides, including peptidomimetics and peptide analogs are known to those of skill in the art. See e.g. Lihu Yang et al., *Proc. Natl. Acad. Sci. U.S.A.*, 1; 95(18): 10836-10841 (Sep. 1, 1998); Harlow and Lane (1988) "Antibodies: A Laboratory Manuel" Cold Spring Harbor Publications, New York; Harlow and Lane (1999) "Using Antibodies" A Laboratory Manuel, Cold Spring Harbor Publications, New York.

According to one aspect, the downregulation of connexin expression may be based generally upon the antisense approach using antisense polynucleotides (such as DNA or RNA polynucleotides), and more particularly upon the use of antisense oligodeoxynucleotides (ODN). These polynucleotides (e.g., ODN) target the connexin protein (s) to be downregulated. Typically the polynucleotides are single stranded, but may be double stranded.

The antisense polynucleotide may inhibit transcription and/or translation of a connexin. Preferably the polynucleotide is a specific inhibitor of transcription and/or translation from the connexin gene or mRNA, and does not inhibit transcription and/or translation from other genes or mRNAs. The product may bind to the connexin gene or mRNA either (i) 5' to the coding sequence, and/or (ii) to the coding sequence, and/or (iii) 3' to the coding sequence.

The antisense polynucleotide is generally antisense to a connexin mRNA. Such a polynucleotide may be capable of hybridizing to the connexin mRNA and may thus inhibit the expression of connexin by interfering with one or more aspects of connexin mRNA metabolism including transcription, mRNA processing, mRNA transport from the nucleus, translation or mRNA degradation. The antisense polynucleotide typically hybridizes to the connexin mRNA to form a duplex which can cause direct inhibition of translation and/or destabilization of the mRNA. Such a duplex may be susceptible to degradation by nucleases.

The antisense polynucleotide may hybridize to all or part of the connexin mRNA. Typically the antisense polynucleotide hybridizes to the ribosome binding region or the coding region of the connexin mRNA. The polynucleotide may be complementary to all of or a region of the connexin mRNA. For example, the polynucleotide may be the exact complement of all or a part of connexin mRNA. However, absolute complementarity is not required and polynucleotides which have sufficient complementarity to form a duplex having a melting temperature of greater than about 20° C., 30° C. or 40° C. under physiological conditions are particularly suitable for use in the present invention.

Thus the polynucleotide is typically a homologue of a sequence complementary to the mRNA. The polynucleotide may be a polynucleotide which hybridizes to the connexin mRNA under conditions of medium to high stringency such as 0.03M sodium chloride and 0.03M sodium citrate at from about 50° C. to about 60° C.

For certain aspects, suitable polynucleotides are typically from about 6 to 40 nucleotides in length. Preferably a polynucleotide may be from about 12 to about 35 nucleotides in length, or alternatively from about 12 to about 20 nucleotides in length or more preferably from about 18 to about 32 nucleotides in length. According to an alternative aspect, the polynucleotide may be at least about 40, for example at least about 60 or at least about 80, nucleotides in length and up to about 100, about 200, about 300, about 400, about 500, about 1000, about 2000 or about 3000 or more nucleotides in length.

The connexin protein or proteins targeted by the polynucleotide will be dependent upon the site at which downregulation is to be effected. This reflects the non-uniform make-up of gap junction(s) at different sites throughout the body in terms of connexin sub-unit composition. The connexin is a connexin that naturally occurs in a human or animal in one aspect or naturally occurs in the tissue in which connexin expression or activity is to be decreased. The connexin gene (including coding sequence) generally has homology with the coding sequence of one or more of the specific connexins mentioned herein, such as homology with the connexin 43 coding sequence shown in Table 8. The connexin is typically an α or β connexin. Preferably the connexin is an α connexin and is expressed in the tissue to be treated.

Some connexin proteins are however more ubiquitous than others in terms of distribution in tissue. One of the most widespread is connexin 43. Polynucleotides targeted to connexin 43 are particularly suitable for use in the present invention. In other aspects other connexins are targeted.

Anti-connexin polynucleotides include connexin antisense polynucleotides as well as polynucleotides which have functionalities which enable them to downregulate connexin expression. Other suitable anti-connexin polynucleotides include RNAi polynucleotides and SiRNA polynucleotides.

In one preferred aspect, the antisense polynucleotides are targeted to the mRNA of one connexin protein only. Most preferably, this connexin protein is connexin 43. In another aspect, connexin protein is connexin 26, 30, 31.1, 32, 36, 37, 40, or 45. In other aspects, the connexin protein is connexin 30.3, 31, 40.1, or 46.6.

It is also contemplated that polynucleotides targeted to separate connexin proteins be used in combination (for example 1, 2, 3, 4 or more different connexins may be targeted). For example, polynucleotides targeted to connexin 43, and one or more other members of the connexin family (such as connexin 26, 30, 30.3, 31.1, 32, 36, 37, 40, 40.1, 45, and 46.6) can be used in combination.

Alternatively, the antisense polynucleotides may be part of compositions which may comprise polynucleotides to more than one connexin protein. Preferably, one of the connexin proteins to which polynucleotides are directed is connexin 43. Other connexin proteins to which oligodeoxynucleotides are directed may include, for example, connexins 26, 30, 30.3, 31.1, 32, 36, 37, 40, 40.1, 45, and 46.6. Suitable exemplary polynucleotides (and ODNs) directed to various connexins are set forth in Table 1.

Individual antisense polynucleotides may be specific to a particular connexin, or may target 1, 2, 3 or more different connexins. Specific polynucleotides will generally target sequences in the connexin gene or mRNA which are not conserved between connexins, whereas non-specific polynucleotides will target conserved sequences for various connexins.

The polynucleotides for use in the invention may suitably be unmodified phosphodiester oligomers. Such oligodeoxynucleotides may vary in length. A 30 mer polynucleotide has been found to be particularly suitable.

Many aspects of the invention are described with reference to oligodeoxynucleotides. However it is understood that other suitable polynucleotides (such as RNA polynucleotides) may be used in these aspects.

The antisense polynucleotides may be chemically modified. This may enhance their resistance to nucleases and may enhance their ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates. Alternatively mixed backbone oligonucleotides ("MBOs") may be used. MBOs contain segments of phosphothioate oligodeoxynucleotides and appropriately placed segments of modified oligodeoxy- or oligoribonucleotides. MBOs have segments of phosphorothioate linkages and other segments of other modified oligonucleotides, such as methylphosphonate, which is non-ionic, and very resistant to nucleases or 2'-O-alkyloligoribonucleotides. Methods of preparing modified backbone and mixed backbone oligonucleotides are known in the art.

The precise sequence of the antisense polynucleotide used in the invention will depend upon the target connexin protein. In one embodiment, suitable connexin antisense polynucleotides can include polynucleotides such as oligodeoxynucleotides selected from the following sequences set forth in Table 1:

TABLE 1

| | | |
|---|---|---|
| 5' GTA ATT GCG GCA AGA AGA ATT GTT TCT GTC 3' | (connexin 43) | (SEQ.ID.NO: 1) |
| 5' GTA ATT GCG GCA GGA GGA ATT GTT TCT GTC 3' | (connexin 43) | (SEQ.ID.NO: 2) |
| 5' GGC AAG AGA CAC CAA AGA CAC TAC CAG CAT 3' | (connexin 43) | (SEQ.ID.NO: 3) |
| 5' TCC TGA GCA ATA CCT AAC GAA CAA ATA 3' | (connexin 26) | (SEQ.ID.NO: 4) |
| 5' CAT CTC CTT GGT GCT CAA CC 3' | (connexin 37) | (SEQ.ID.NO: 5) |
| 5' CTG AAG TCG ACT TGG CTT GG 3' | (connexin 37) | (SEQ.ID.NO: 6) |
| 5' CTC AGA TAG TGG CCA GAA TGC 3' | (connexin 30) | (SEQ.ID.NO: 7) |
| 5' TTG TCC AGG TGA CTC CAA GG 3' | (connexin 30) | (SEQ.ID.NO: 8) |
| 5' CGT CCG AGC CCA GAA AGA TGA GGT C 3' | (connexin 31.1) | (SEQ.ID.NO: 9) |
| 5' AGA GGC GCA CGT GAG ACA C 3' | (connexin 31.1) | (SEQ.ID.NO: 10) |
| 5' TGA AGA CAA TGA AGA TGT T 3' | (connexin 31.1) | (SEQ.ID.NO: 11) |
| 5' TTT CTT TTC TAT GTG CTG TTG GTG A 3' | (connexin 32) | (SEQ.ID.NO: 12) |

Suitable polynucleotides for the preparation of the combined polynucleotide compositions described herein include for example, polynucleotides to Connexin Cx43 and polynucleotides for connexins 26, 30, 31.1, 32 and 37 as described in Table 1 above.

Although the precise sequence of the antisense polynucleotide used in the invention will depend upon the target connexin protein, for connexin 43, antisense polynucleotides having the following sequences have been found to be particularly suitable:

```
                                            (SEQ.ID.NO: 1)
GTA ATT GCG GCA AGA AGA ATT GTT TCT GTC;

(SEQ.ID.NO: 2)
GTA ATT GCG GCA GGA GGA ATT GTT TCT GTC;
and (SEQ.ID.NO: 3)
GGC AAG AGA CAC CAA AGA CAC TAC CAG CAT.
```

For example, suitable antisense polynucleotides for connexins 26, 31.1 and 32 have the following sequences:

```
(connexin 26)
                                            (SEQ.ID.NO: 4)
5' TCC TGA GCA ATA CCT AAC GAA CAA ATA;

(connexin 31.1)
                                            (SEQ.ID.NO: 9)
5' CGT CCG AGC CCA GAA AGA TGA GGT C;
and (connexin 32)
                                            (SEQ.ID.NO: 12)
5' TTT CTT TTC TAT GTG CTG TTG GTG A.
```

Other connexin antisense polynucleotide sequences useful according to the methods of the present invention include:

```
(connexin 37)
                                            (SEQ.ID.NO: 5)
5' CAT CTC CTT GGT GCT CAA CC 3';

(connexin 37)
                                            (SEQ.ID.NO: 6)
5' CTG AAG TCG ACT TGG CTT GG 3';

(connexin 30)
                                            (SEQ.ID.NO: 7)
5' CTC AGA TAG TGG CCA GAA TGC 3';

(connexin 30)
                                            (SEQ.ID.NO: 8)
5' TTG TCC AGG TGA CTC CAA GG 3';

(connexin 31.1)
                                            (SEQ.ID.NO: 10)
5' AGA GGC GCA CGT GAG ACA C 3';
and (connexin 31.1)
                                            (SEQ.ID.NO: 11)
5' TGA AGA CAA TGA AGA TGT T 3'.
```

Polynucleotides, including ODN's, directed to connexin proteins can be selected in terms of their nucleotide sequence by any convenient, and conventional, approach. For example, the computer programs MacVector and OligoTech (from Oligos etc. Eugene, Oreg., USA) can be used. Once selected, the ODN's can be synthesized using a DNA synthesizer.

Polynucleotide Homologues

Homology and homologues are discussed herein (for example, the polynucleotide may be a homologue of a complement to a sequence in connexin mRNA). Such a polynucleotide typically has at least about 70% homology, preferably at least about 80%, at least about 90%, at least about 95%, at least about 97% or at least about 99% homology with the relevant sequence, for example over a region of at least about 15, at least about 20, at least about 40, at least about 100 more contiguous nucleotides (of the homologous sequence).

Homology may be calculated based on any method in the art. For example the UWGCG Package provides the BESTFIT program which can be used to calculate homology (for example used on its default settings) (Devereux et al (1984) Nucleic Acids Research 12, p 387-395). The PILEUP and BLAST algorithms can be used to calculate homology or line up sequences (typically on their default settings), for example as described in Altschul S. F. (1993) J Mol Evol 36: 290-300; Altschul, S, F et al (1990) J Mol Biol 215: 403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighborhood word score threshold (Altschul et al, supra). These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached.

The BLAST algorithm parameters W, T and X determine the sensitivity and speed of the alignment. The BLAST program uses as defaults a word length (W), the BLOSUM62 scoring matrix (see Henikoff and Henikoff (1992) Proc. Natl. Acad. Sci. USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to a second sequence is less than about 1, preferably less than about 0.1, more preferably less than about 0.01, and most preferably less than about 0.001.

The homologous sequence typically differs from the relevant sequence by at least about (or by no more than about) 2, 5, 10, 15, 20 more mutations (which may be substitutions, deletions or insertions). These mutations may be measured across any of the regions mentioned above in relation to calculating homology.

The homologous sequence typically hybridizes selectively to the original sequence at a level significantly above background. Selective hybridization is typically achieved using conditions of medium to high stringency (for example 0.03M sodium chloride and 0.03M sodium citrate at from about 50° C. to about 60° C.). However, such hybridization may be carried out under any suitable conditions known in the art (see Sambrook et al. (1989), Molecular Cloning: A Laboratory Manual). For example, if high stringency is required, suitable conditions include 0.2×SSC at 60° C. If lower stringency is required, suitable conditions include 2×SSC at 60° C.

Peptide and Polypeptide Anti-Connexin Agents

Binding proteins, including peptides, peptidomimetics, antibodies, antibody fragments, and the like, are also suitable modulators of gap junctions and hemichannels.

Binding proteins include, for example, monoclonal antibodies, polyclonal antibodies, antibody fragments (including, for example, Fab, F(ab')$_2$ and Fv fragments; single chain antibodies; single chain Fvs; and single chain binding molecules such as those comprising, for example, a binding domain, hinge, CH2 and CH3 domains, recombinant antibodies and antibody fragments which are capable of binding an antigenic determinant (i.e., that portion of a molecule, generally referred to as an epitope) that makes contact with a particular antibody or other binding molecule. These binding proteins, including antibodies, antibody fragments, and so on, may be chimeric or humanized or otherwise made to be less immunogenic in the subject to whom they are to be administered, and may be synthesized, produced recombinantly, or produced in expression libraries. Any binding molecule known in the art or later discovered is envisioned, such as those referenced herein and/or described in greater detail in the art. For example, binding proteins include not only antibodies, and the like, but also ligands, receptors, peptidomimetics, or other binding fragments or molecules (for example, produced by phage display) that bind to a target (e.g. connexin, hemichannel, or associated molecules).

Binding molecules will generally have a desired specificity, including but not limited to binding specificity, and desired affinity. Affinity, for example, may be a $K_a$ of greater than or equal to about $10^4$ M$^{-1}$, greater than or equal to about $10^6$ M$^{-1}$, greater than or equal to about $10^7$ M$^{-1}$, greater than or equal to about $10^8$ M$^{-1}$. Affinities of even greater than about $10^8$ M$^{-1}$ are suitable, such as affinities equal to or greater than about $10^9$ M$^{-1}$, about $10^{10}$ M$^{-1}$, about $10^{11}$ M$^{-1}$, and about $10^{12}$ M$^{-1}$. Affinities of binding proteins according to the present invention can be readily determined using conventional techniques, for example those described by Scatchard et al., 1949 *Ann. N.Y. Acad. Sci.* 51: 660.

By using data obtained from hydropathy plots, it has been proposed that a connexin contains four-transmembrane-spanning regions and two short extra-cellular loops. The positioning of the first and second extracellular regions of connexin was further characterized by the reported production of anti-peptide antibodies used for immunolocalization of the corresponding epitopes on split gap junctions. Goodenough D. A. *J Cell Biol* 107: 1817-1824 (1988); Meyer R. A., *J Cell Biol* 119: 179-189 (1992).

The extracellular domains of a hemichannel contributed by two adjacent cells "dock" with each other to form complete gap junction channels. Reagents that interfere with the interactions of these extracellular domains can impair cell-to-cell communication. Peptide inhibitors of gap junctions and hemichannels have been reported. See for example Berthoud, V. M. et al., *Am J. Physiol. Lung Cell Mol. Physiol.* 279: L619-L622 (2000); Evans, W. H. and Boitano, S. *Biochem. Soc. Trans.* 29: 606-612, and De Vriese A. S., et al. *Kidney Int.* 61: 177-185 (2001). Short peptides corresponding to sequences within the extracellular loops of connexins were said to inhibit intercellular communication. Boitano S. and Evans W. *Am J Physiol Lung CellMol Physiol* 279: L623-L630 (2000). The use of peptides as inhibitors of cell-cell channel formation produced by connexin (Cx) 32 expressed in paired *Xenopus* oocytes has also been reported. Dahl G, et al., *Biophys J* 67: 1816-1822 (1994). Berthoud, V. M. and Seul, K. H., summarized some of these results. *Am J., Physiol. Lung Cell Mol. Physiol.* 279: L619-L622 (2000).

Anti-connexin agents include peptides comprising an amino acid sequence corresponding to a transmembrane region (e.g. 1$^{st}$ to 4$^{th}$) of a connexin (e.g. connexin 45, 43, 26, 30, 31.1, and 37). Anti-connexin agents may comprise a peptide comprising an amino acid sequence corresponding to a portion of a transmembrane region of a connexin 45. Anti-connexin agents include a peptide having an amino acid sequence that comprises about 5 to 20 contiguous amino acids of SEQ.ID.NO:13, a peptide having an amino acid sequence that comprises about 8 to 15 contiguous amino acids of SEQ.ID.NO: 13, or a peptide having an amino acid sequence that comprises about 11 to 13 contiguous amino acids of SEQ.ID.NO:13. Other embodiments are directed to an anti-connexin agent that is a peptide having an amino acid sequence that comprises at least about 5, at least about 6, at least about 7, at least about 8, at least about 9, at least about 10, at least about 11, at least about 12, at least about 13, at least about 14, at least about 15, at least about 20, at least about 25, or at least about 30 contiguous amino acids of SEQ.ID.NO:13. In certain anti-connexin agents provided herein, the extracellular domains of connexin 45 corresponding to the amino acids at positions 46-75 and 199-228 of SEQ ID NO: 13 may be used to develop the particular peptide sequences. Certain peptides described herein have an amino acid sequence corresponding to the regions at positions 46-75 and 199-228 of SEQ.ID.NO: 13. The peptides need not have an amino acid sequence identical to those portions of SEQ.ID.NO: 13, and conservative amino acid changes may be made such that the peptides retain binding activity or functional activity. Alternatively, the peptide may target regions of the connexin protein other than the extracellular domains (e.g. the portions of SEQ.ID.NO:13 not corresponding to positions 46-75 and 199-228).

Also, suitable anti-connexin agents comprise a peptide comprising an amino acid sequence corresponding to a portion of a transmembrane region of a connexin 43. Anti-connexin agents include peptides having an amino acid sequence that comprises about 5 to 20 contiguous amino acids of SEQ.ID.NO: 14, peptides having an amino acid sequence that comprises about 8 to 15 contiguous amino acids of SEQ.ID.NO:14, or peptides having an amino acid sequence that comprises about 11 to 13 contiguous amino acids of SEQ.ID.NO: 14. Other anti-connexin agents include a peptide having an amino acid sequence that comprises at least about 5, at least about 6, at least about 7, at least about 8, at least about 9, at least about 10, at least about 11, at least about 12, at least about 13, at least about 14, at least about 15, at least about 20, at least about 25, or at least about 30 contiguous amino acids of SEQ.ID.NO:14. Other anti-connexin agents comprise the extracellular domains of connexin 43 corresponding to the amino acids at positions 37-76 and 178-208 of SEQ.ID.NO: 14. Anti-connexin agents include peptides described herein which have an amino acid sequence corresponding to the regions at positions 37-76 and 178-208 of SEQ.ID.NO: 14. The peptides need not have an amino acid sequence identical to those portions of SEQ.ID.NO: 14, and conservative amino acid changes may be made such that the peptides retain binding activity or functional activity. Alternatively, peptides may target regions of the connexin protein other than the extracellular domains (e.g. the portions of SEQ.ID.NO:14 not corresponding to positions 37-76 and 178-208).

Connexin 45
(SEQ ID NO. 13)

Met Ser Trp Ser Phe Leu Thr Arg Leu Leu Glu Glu Ile His Asn His
1               5                   10                  15

Ser Thr Phe Val Gly Lys Ile Trp Leu Thr Val Leu Ile Val Phe Arg
                20                  25                  30

Ile Val Leu Thr Ala Val Gly Gly Glu Ser Ile Tyr Tyr Asp Glu Gln
                35                  40                  45

Ser Lys Phe Val Cys Asn Thr Glu Gln Pro Gly Cys Glu Asn Val Cys
50                      55                  60

Tyr Asp Ala Phe Ala Pro Leu Ser His Val Arg Phe Trp Val Phe Gln
65                      70                  75                  80

Ile Ile Leu Val Ala Thr Pro Ser Val Met Tyr Leu Gly Tyr Ala Ile
                85                  90                  95

His Lys Ile Ala Lys Met Glu His Gly Glu Ala Asp Lys Lys Ala Ala
                100                 105                 110

Arg Ser Lys Pro Tyr Ala Met Arg Trp Lys Gln His Arg Ala Leu Glu
                115                 120                 125

Glu Thr Glu Glu Asp Asn Glu Glu Asp Pro Met Met Tyr Pro Glu Met
                130                 135                 140

Glu Leu Glu Ser Asp Lys Glu Asn Lys Glu Gln Ser Gln Pro Lys Pro
145                 150                 155                 160

Lys His Asp Gly Arg Arg Arg Ile Arg Glu Asp Gly Leu Met Lys Ile
                165                 170                 175

Tyr Val Leu Gln Leu Leu Ala Arg Thr Val Phe Glu Val Gly Phe Leu
                180                 185                 190

Ile Gly Gln Tyr Phe Leu Tyr Gly Phe Gln Val His Pro Phe Tyr Val
                195                 200                 205

Cys Ser Arg Leu Pro Cys Pro His Lys Ile Asp Cys Phe Ile Ser Arg
210                 215                 220

Pro Thr Glu Lys Thr Ile Phe Leu Leu Ile Met Tyr Gly Val Thr Gly
225                 230                 235                 240

Leu Cys Leu Leu Leu Asn Ile Trp Glu Met Leu His Leu Gly Phe Gly
                245                 250                 255

Thr Ile Arg Asp Ser Leu Asn Ser Lys Arg Arg Glu Leu Glu Asp Pro
                260                 265                 270

Gly Ala Tyr Asn Tyr Pro Phe Thr Trp Asn Thr Pro Ser Ala Pro Pro
                275                 280                 285

Gly Tyr Asn Ile Ala Val Lys Pro Asp Gln Ile Gln Tyr Thr Glu Leu
                290                 295                 300

Ser Asn Ala Lys Ile Ala Tyr Lys Gln Asn Lys Ala Asn Thr Ala Gln
305                 310                 315                 320

Glu Gln Gln Tyr Gly Ser His Glu Glu Asn Leu Pro Ala Asp Leu Glu
                325                 330                 335

Ala Leu Gln Arg Glu Ile Arg Met Ala Gln Glu Arg Leu Asp Leu Ala
                340                 345                 350

Val Gln Ala Tyr Ser His Gln Asn Asn Pro His Gly Pro Arg Glu Lys
                355                 360                 365

Lys Ala Lys Val Gly Ser Lys Ala Gly Ser Asn Lys Ser Thr Ala Ser
                370                 375                 380

Ser Lys Ser Gly Asp Gly Lys Asn Ser Val Trp Ile
385                 390                 395

Connexin 43
(SEQ ID NO. 14)

Met Gly Asp Trp Ser Ala Leu Gly Lys Leu Leu Asp Lys Val Gln Ala
1               5                   10                  15

-continued

```
Tyr Ser Thr Ala Gly Gly Lys Val Trp Leu Ser Val Leu Phe Ile Phe
             20              25              30

Arg Ile Leu Leu Gly Thr Ala Val Glu Ser Ala Trp Gly Asp Glu
         35              40              45

Gln Ser Ala Phe Arg Cys Asn Thr Gln Gln Pro Gly Cys Glu Asn Val
 50              55              60

Cys Tyr Asp Lys Ser Phe Pro Ile Ser His Val Arg Phe Trp Val Leu
 65              70              75              80

Gln Ile Ile Phe Val Ser Val Pro Thr Leu Leu Tyr Leu Ala His Val
             85              90              95

Phe Tyr Val Met Arg Lys Glu Glu Lys Leu Asn Lys Lys Glu Glu Glu
            100             105             110

Leu Lys Val Ala Gln Thr Asp Gly Val Asn Val Asp Met His Leu Lys
            115             120             125

Gln Ile Glu Ile Lys Lys Phe Lys Tyr Gly Ile Glu Glu His Gly Lys
        130             135             140

Val Lys Met Arg Gly Gly Leu Leu Arg Thr Tyr Ile Ile Ser Ile Leu
145             150             155             160

Phe Lys Ser Ile Phe Glu Val Ala Phe Leu Leu Ile Gln Trp Tyr Ile
                165             170             175

Tyr Gly Phe Ser Leu Ser Ala Val Tyr Thr Cys Lys Arg Asp Pro Cys
                180             185             190

Pro His Gln Val Asp Cys Phe Leu Ser Arg Pro Thr Glu Lys Thr Ile
            195             200             205

Phe Ile Ile Phe Met Leu Val Val Ser Leu Val Ser Leu Ala Leu Asn
        210             215             220

Ile Ile Glu Leu Phe Tyr Val Phe Phe Lys Gly Val Lys Asp Arg Val
225             230             235             240

Lys Gly Lys Ser Asp Pro Tyr His Ala Thr Ser Gly Ala Leu Ser Pro
                245             250             255

Ala Lys Asp Cys Gly Ser Gln Lys Tyr Ala Tyr Phe Asn Gly Cys Ser
            260             265             270

Ser Pro Thr Ala Pro Leu Ser Pro Met Ser Pro Pro Gly Tyr Lys Leu
        275             280             285

Val Thr Gly Asp Arg Asn Asn Ser Ser Cys Arg Asn Tyr Asn Lys Gln
    290             295             300

Ala Ser Glu Gln Asn Trp Ala Asn Tyr Ser Ala Glu Gln Asn Arg Met
305             310             315             320

Gly Gln Ala Gly Ser Thr Ile Ser Asn Ser His Ala Gln Pro Phe Asp
                325             330             335

Phe Pro Asp Asp Asn Gln Asn Ser Lys Lys Leu Ala Ala Gly His Glu
            340             345             350

Leu Gln Pro Leu Ala Ile Val Asp Gln Arg Pro Ser Ser Arg Ala Ser
        355             360             365

Ser Arg Ala Ser Ser Arg Pro Arg Pro Asp Asp Leu Glu Ile
370             375             380
```

The anti-connexin peptides may comprise sequences corresponding to a portion of the connexin extracellular domains with conservative amino acid substitutions such that peptides are functionally active anti-connexin agents. Exemplary conservative amino acid substitutions include for example the substitution of a nonpolar amino acid with another nonpolar amino acid, the substitution of an aromatic amino acid with another aromatic amino acid, the substitution of an aliphatic amino acid with another aliphatic amino acid, the substitution of a polar amino acid with another polar amino acid, the substitution of an acidic amino acid with another acidic amino acid, the substitution of a basic amino acid with another basic amino acid, and the substitution of an ionizable amino acid with another ionizable amino acid.

Exemplary peptides targeted to connexin 43 are shown below in Table 2. M1, 2, 3 and 4 refer to the $1^{st}$ to $4^{th}$ transmembrane regions of the connexin 43 protein respectively. E1 and E2 refer to the first and second extracellular loops respectively.

TABLE 2

Peptidic Inhibitors of Intercellular Communication (cx43)

| Sequence | Location | SEQ ID NO |
|---|---|---|
| FEVAFLLIQWI | M3 & E2 | (SEQ.ID.NO: 15) |
| LLIQWYIGFSL | E2 | (SEQ.ID.NO: 16) |
| SLSAVYTCKRDPCPHQ | E2 | (SEQ.ID.NO: 17) |
| VDCFLSRPTEKT | E2 | (SEQ.ID.NO: 18) |
| SRPTEKTIFII | E2 & M4 | (SEQ.ID.NO: 19) |
| LGTAVESAWGDEQ | M1 & E1 | (SEQ.ID.NO: 20) |
| QSAFRCNTQQPG | E1 | (SEQ.ID.NO: 21) |
| QQPGCENVCYDK | E1 | (SEQ.ID.NO: 22) |
| VCYDKSFPISHVR | E1 | (SEQ.ID.NO: 23) |

Table 3 provides additional exemplary connexin peptides used in inhibiting hemichannel or gap junction function. In other embodiments, conservative amino acid changes are made to the peptides or fragments thereof.

TABLE 3

Additional Peptidic Inhibitors of Intercellular Communication (cx32, cx43)

| Connexin | Location | AA's and Sequence | SEQ ID NO |
|---|---|---|---|
| Cx32 | E1 39-77 | AAESVWGDEIKSSFICNTLQPGCNSVCYDHFFPISHVR | (SEQ.ID.NO: 24) |
| Cx32 | E1 41-52 | ESVWGDEKSSFI | (SEQ.ID.NO: 25) |
| Cx32 | E1 52-63 | ICNTLQPGCNSV | (SEQ.ID.NO: 26) |
| Cx32 | E1 62-73 | SVCYDHFFPISH | (SEQ.ID.NO: 27) |
| Cx32 | E2 64-188 | RLVKCEAFPCPNTVDCFVSRPTEKT | (SEQ.ID.NO: 28) |
| Cx32 | E2 166-177 | VKCEAFPCPNTV | (SEQ.ID.NO: 29) |
| Cx32 | E1 177-188 | VDCFVSRPTEKT | (SEQ.ID.NO: 30) |
| Cx32 | E1 63-75 | VCYDHFFPISHVR | (SEQ.ID.NO: 31) |
| Cx32 | E1 45-59 | VWGDEKSSFICNTLQPGY | (SEQ.ID.NO: 32) |
| Cx32 | E1 46-59 | DEKSSFICNTLQPGY | (SEQ.ID.NO: 33) |
| Cx32 | E2 182-192 | SRPTEKTVFTV | (SEQ.ID.NO: 34) |
| Cx32/Cx43 | E2 182-188/ 201-207 | SRPTEKT | (SEQ.ID.NO: 35) |
| Cx32 | E1 52-63 | ICNTLQPGCNSV | (SEQ.ID.NO: 36) |
| Cx40 | E2 177-192 | FLDTLHVCRRSPCPHP | (SEQ.ID.NO: 37) |
| Cx43 | E2 188-205 | KRDPCHQVDCFLSRPTEK | (SEQ.ID.NO: 38) |

Table 4 provides the extracellular loops for connexin family members which are used to develop peptide inhibitors for use as described herein. The peptides and provided in Table 4, and fragments thereof, are used as peptide inhibitors in certain non-limiting embodiments. In other non-limiting embodiments, peptides comprising from about 8 to about 15, or from about 11 to about 13 amino contiguous amino acids of the peptides in this Table 4 are peptide inhibitors. Conservative amino acid changes may be made to the peptides or fragments thereof.

TABLE 4

Extracellular loops for various connexin family members

E1

| | | |
|---|---|---|
| huCx26 | KEVWGDEQADFVCNTLQPGCKNVCYDHYFPISHIR | (SEQ.ID.NO: 39) |
| huCx30 | QEVWGDEQEDFVCNTLQPGCKNVCYDHFFPVSHIR | (SEQ.ID.NO: 40) |
| huCx30.3 | EEVWDDEQKDFVCNTKQPGCPNVCYDEFFPVSHVR | (SEQ.ID.NO: 41) |
| huCx31 | ERVWGDEQKDFDCNTKQPGCTNVCYDNYFPISNIR | (SEQ.ID.NO: 42) |
| huCx31.1 | ERVWSDDHKDFDCNTRQPGCSNVCFDEFFPVSHVR | (SEQ.ID.NO: 43) |
| huCx32 | ESVWGDEKSSFICNTLQPGCNSVCYDQFFPISHVR | (SEQ.ID.NO: 44) |
| huCx36 | ESVWGDEQSDFECNTAQPGCTNVCYDQAFPISHIR | (SEQ.ID.NO: 45) |
| huCx37 | ESVWGDEQSDFECNTAQPGCTNVCYDQAFPISHIR | (SEQ.ID.NO: 46) |
| huCx40.1 | RPVYQDEQERFVCNTLQPGCANVCYDVFSPVSHLR | (SEQ.ID.NO: 47) |
| huCx43 | ESAWGDEQSAFRCNTQQPGCENVCYDKSFPISHVR | (SEQ.ID.NO: 48) |
| huCx46 | EDVWGDEQSDFTCNTQQPGCBNVCYBRAFPISHIR | (SEQ.ID.NO: 49) |
| huCx46.6 | EAIYSDEQAKFTCNTRQPGCDNVCYDAFAPLSHVR | (SEQ.ID.NO: 50) |
| huCx40 | ESSWGDEQADFRCDTIQPGCQNVCTDQAFPISHIR | (SEQ.ID.NO: 51) |
| huCx45 | GESIYYDEQSKFVCNTEQPGCENVCYDAFAPLSHVR | (SEQ.ID NO: 52) |

E2

| | | |
|---|---|---|
| huCx26 | MYVFYVMYDGFSMQRLVKCNAWPCPNTVDCFVSRPTEKT | (SEQ.ID.NO: 53) |
| huCx30 | MYVFYFLYNGYHLPWVLKCGIDPCPNLVDCFISRPTEKT | (SEQ.ID.NO: 54) |
| huCx30.3 | LYIFHRLYKDYDMPRVVACSVEPCPHTVDCYISRPTEKK | (SEQ.ID.NO: 55) |
| huCx31 | LYLLHTLWHGFNMPRLVQCANVAPCPNIVDCYIARPTEKK | (SEQ.ID.NO: 56) |
| huCx31.1 | LYVFHSFYPKYILPPVVKCHADPCPNIVDCFISKPSEKN | (SEQ.ID.NO: 57) |
| huCx32 | MYVFYLLYPGYAMVRLVKCDVYPCPNTVDCFVSRPTEKT | (SEQ.ID.NO: 58) |
| huCx36 | LYGWTMEPVFVCQRAPCPYLVDCFVSRPTEKT | (SEQ.ID.NO: 59) |
| huCx37 | LYGWTMEPVFVCQRAPCPYLVDCFVSRPTEKT | (SEQ.ID.NO: 60) |
| huCx40.1 | GALHYFLFGFLAPKKFPCTRPPCTGVVDCYVSRPTSKS | (SEQ.ID.NO: 61) |
| huCx43 | LLIQWYIYGFSLSAVYTCKRDPCPHQVDCFLSRPTEKT | (SEQ.ID NO: 62) |
| huCx46 | IAGQYFLYGFELKPLYRCDRWPCPNTVDCFISRPTEKT | (SEQ.ID.NO: 63) |
| huCx46.6 | LVGQYLLYGFEVRPFFPCSRQPCPHVVDCFVSRPTEKT | (SEQ.ID NO: 64) |
| huCx40 | IVGQYFIYGIFLTTLHVCRRSPCPHPVNCYVSRPTEKN | (SEQ.ID NO: 65) |
| huCx45 | LIGQYFLYGFQVHPFYVCSRLPCHPKIDCFISRPTEKT | (SEQ.ID.NO: 66) |

Table 5 provides the extracellular domain for connexin family members which may be used to develop peptide anti-connexin agents. The peptides and provided in Table 5, and fragments thereof, may also be used as peptide anti-connexin agents. Such peptides may comprise from about 8 to about 15, or from about 11 to about 13 amino contiguous amino acids of the peptide sequence in this Table 5. Conservative amino acid changes may be made to the peptides or fragments thereof.

TABLE 5

Extracellular domains

| | | |
|---|---|---|
| Peptide | VDCFLSRPTEKT | (SEQ.ID.NO: 18) |
| Peptide | SRPTEKTIFII | (SEQ.ID.NO: 19) |

TABLE 5-continued

Extracellular domains

| | | |
|---|---|---|
| huCx43 | LLIQWYIYGFSLSAVYTCKRDPCPHQVDCFLSRPTEKTIFII | (SEQ.ID.NO: 67) |
| huCx26 | MYVFYVMYDGFSMQRLVKCNAWPCPNTVDCFVSRPTEKTVFTV | (SEQ.ID.NO: 68) |
| huCx30 | YVFYFLYNGYHLPWVLKCGIDPCPNLVDCFISRPTEKTVFTI | (SEQ.ID.NO: 69) |
| huCx30.3 | LYIFHRLYKDYDMPRVVACSVEPCPHTVDCYISRPTEKKVFTY | (SEQ.ID.NO: 70) |
| huCx31 | LYLLHTLWHGFNMPRLVQCANVAPCPNIVDCYIARPTEKKTY | (SEQ.ID.NO: 71) |
| huCx31.1 | LYVFHSFYPKYILPPVVKCHADPCPNIVDCFISKPSEKNIFTL | (SEQ.ID.NO: 72) |
| huCx32 | MYVFYLLYPGYAMVRLVKCDVYPCPNTVDCFVSRPTEKTVFTV | (SEQ.ID.NO: 73) |
| huCx36 | LYGWTMEPVFVCQRAPCPYLVDCFVSRPTEKTIFII | (SEQ.ID.NO: 74) |
| huCx37 | LYGWTMEPVFVCQRAPCPYLVDCFVSRPTEKTIFII | (SEQ.ID.NO: 75) |
| huCx40.1 | GALHYFLFGFLAPKKFPCTRPPCTGVVDCYVSRPTEKSLLML | (SEQ.ID.NO: 76) |
| huCx46 | IAGQYFLYGFELKPLYRCDRWPCPNTVDCFISRPTEKTIFII | (SEQ.ID.NO: 77) |
| huCx46.6 | LVGQYLLYGFEVRPFFPCSRQPCPHVVDCFVSRPTEKTVFLL | (SEQ.ID.NO: 78) |
| huCx40 | IVGQYFIYGIFLTTLHVCRRSPCPHPVNCYSRPTEKNVFIV | (SEQ.ID.NO: 79) |
| huCx45 | LIGQYFLYGFQVHPFYVCSRLPCHPKIDCFISRPTEKTIFLL | (SEQ.ID.NO: 80) |

Table 6 provides peptides inhibitors of connexin 40 shown with reference to the extracellular loops (E1 and E2) of connexin 40. The bold amino acids are directed to the transmembrane regions of connexin 40.

TABLE 6

Cx40 peptide inhibitors

E2

| | |
|---|---|
| LGTAAESSWGDEQADFRCDTIQPGCQNVCIDQAFPISHIRFWVLQ | (SEQ.ID.NO: 94) |
| LGTAAESSWGDEQA | (SEQ.ID.NO: 94) |
| DEQADFRCDTIQP | (SEQ.ID.NO: 94) |
| TIQPGCQNVCTDQ | (SEQ.ID.NO: 94) |
| VCTDQAFPISHIR | (SEQ.ID.NO: 94) |
| AFPISHIRFWVLQ | (SEQ.ID.NO: 94) |

E2

| | |
|---|---|
| MEVGFIVGQYFIYGIFLTTLHVCRRSPCPHPVNCYVSRPTEKNVFIV | (SEQ.ID.NO: 94) |
| MEVGFIVGQYF | (SEQ.ID.NO: 94) |
| IVGQYFIYGIFL | (SEQ.ID.NO: 94) |
| GIFLTTLHVCRRSP | (SEQ.ID.NO: 94) |
| RRSPCPHPVNCY | (SEQ.ID.NO: 94) |
| VNCYVSRPTEKN | (SEQ.ID.NO: 94) |
| SRPTEKNVFIV | (SEQ.ID.NO: 94) |

Table 7 provides peptides inhibitors of connexin 45 shown with reference to the extracellular loops (E1 and E2) of connexin 45. The bold amino acids are directed to the transmembrane regions of connexin 45

TABLE 7

Cx45 peptide inhibitors

E1

| | |
|---|---|
| LTAVGGESIYYDEQSKFVCNTEQPGCENVCYDAFAPLSHVRFWVFQ | (SEQ.ID.NO: 94) |
| LTAVGGESIYYDEQS | (SEQ.ID.NO: 95) |
| DEQSKFVCNTEQP | (SEQ.ID.NO: 96) |
| TEQPGCENVCYDA | (SEQ.ID.NO: 97) |
| VCYDAFAPLSHVR | (SEQ.ID.NO: 98) |
| APLSHVRFWVFQ | (SEQ.ID.NO: 99) |

E2

| | |
|---|---|
| FEVGFLIGQYFLYGFQVHPFYVCSRLPCHPKIDCFISRPTEKTIFLL | (SEQ.ID.NO: 100) |
| FEVGFLIGQYF | (SEQ.ID.NO: 101) |
| LIGQYFLYGFQV | (SEQ.ID.NO: 102) |
| GFQVHPFYVCSRLP | (SEQ.ID.NO: 103) |
| SRLPCHPKIDCF | (SEQ.ID.NO: 104) |
| IDCFISRPTEKT | (SEQ.ID.NO: 105) |
| SRPTEKTIFLL | (SEQ.ID.NO: 106) |

In certain embodiments, it is preferred that certain peptide inhibitors block hemichannels without disrupting existing gap junctions. While not wishing to be bound to any particular theory or mechanism, it is also believed that certain peptidomimetics (e.g. VCYDKSFPISHVR, (SEQ. ID.NO: 23) block hemichannels without causing uncoupling of gap junctions (See Leybeart et al., *Cell Commun. Adhes.* 10: 251-257 (2003)), or do so in lower dose amounts. The peptide SRPTEKTIFII (SEQ.ID.NO: 19) may also be used, for example to block hemichannels without uncoupling of gap junctions. The peptide SRGGEKNVFIV (SEQ. ID.NO: 107) may be used that as a control sequence (DeVriese et al., *Kidney Internat.* 61: 177-185 (2002)). Examples of peptide inhibitors for connexin 45 YVCSRLPCHP (SEQ.ID.NO: 108), QVHPFYVCSRL (SEQ.ID.NO: 109), FEVG-FLIGQYFLY (SEQ.ID.NO: 110), GQYFLYGFQVHP (SEQ.ID.NO: 111), GFQVHPFYVCSR (SEQ. ID.NO: 112), AVGGESIYYDEQ (SEQ.ID.NO), YDEQSK-FVCNTE (SEQ.ID.NO:114), NTEQPGCENVCY (SEQ. ID.NO:115), CYDAFAPLSHVR (SEQ.ID.NO: 116), FAPLSHVRFWVF (SEQ.ID.NO:117) and LIGQY (SEQ. ID.NO:118), QVHPF (SEQ.ID.NO:119), YVCSR (SEQ. ID.NO:120), SRLPC (SEQ.ID.NO:121), LPCHP (SEQ. ID.NO:122) and GESIY (SEQ.ID.NO:123), YDEQSK (SEQ.ID.NO:124), SKFVCN (SEQ.ID.NO:125), TEQPGCEN (SEQ.ID.NO:126), VCYDAFAP (SEQ.ID.NO:127), LSHVRFWVFQ (SEQ.ID.NO:128) The peptides may only be 3 amino acids in length, including SRL, PCH, LCP, CHP, IYY, SKF, QPC, VCY, APL, HVR, or longer, for example: LIQYFLYGFQVHPF (SEQ.ID.NO:129), VHPFYCSRLP-CHP (SEQ.ID.NO:130), VGGESIYYDEQSKFVCNTE-QPG (SEQ.ID.NO:131), TEQPGCENVCYDAFA-PLSHVRF (SEQ.ID.NO:132), AFAPLSHVRFWVFQ (SEQ.ID.NO: 133).

TABLE 8

Table 8A
Human Connexin 43 from GenBank Accession No. M65188 (SEQ.ID.NO: 134)

| | |
|---:|---|
| 1 | ggcttttagc gtgaggaaag taccaaacag cagcggagtt ttaaacttta aatagacagg |
| 61 | tctgagtgcc tgaacttgcc ttttcattft acttcatcct ccaaggagtt caatcacttg |
| 121 | gcgtgacttc actacttta agcaaaagag tggtgcccag gcaacatggg tgactggagc |
| 181 | gccttaggca aactccttga caaggttcaa gcctactcaa ctgctggagg gaaggtgtgg |
| 241 | ctgtcagtac ttttcattft ccgaatcctg ctgctgggga cagcggttga gtcagcctgg |
| 301 | ggagatgagc agtctgcctt tcgttgtaac actcagcaac ctggttgtga aaatgtctgc |
| 361 | tatgacaagt ctttcccaat ctctcatgtg cgcttctggg tcctgcagat catatttgtg |

TABLE 8-continued

| | |
|---|---|
| 421 | tctgtaccca cactcttgta cctggctcat gtgttctatg tgatgcgaaa ggaagagaaa |
| 481 | ctgaacaaga aagaggaaga actcaaggtt gcccaaactg atggtgtcaa tgtggacatg |
| 541 | cacttgaagc agattgagat aaagaagttc aagtacggta ttgaagagca tggtaaggtg |
| 601 | aaaatgcgag gggggttgct gcgaacctac atcatcagta tcctcttcaa gtctatcttt |
| 661 | gaggtggcct tcttgctgat ccagtggtac atctatggat tcagcttgag tgctgtttac |
| 721 | acttgcaaaa gagatccctg cccacatcag gtggactgtt tcctctctcg ccccacggag |
| 781 | aaaaccatct tcatcatctt catgctggtg gtgtccttgg tgtccctggc cttgaatatc |
| 841 | attgaactct tctatgtttt cttcaagggc gttaaggatc gggttaaggg aaagagcgac |
| 901 | ccttaccatg cgaccagtgg tgcgctgagc cctgccaaag actgtgggtc tcaaaaatat |
| 961 | gcttatttca tggctgctc ctcaccaacc gctccctct cgcctatgtc tcctcctggg |
| 1021 | tacaagctgg ttactggcga cagaaacaat tcttcttgcc gcaattacaa caagcaagca |
| 1081 | agtgagcaaa actgggctaa ttacagtgca gaacaaaatc gaatggggca ggcgggaagc |
| 1141 | accatctcta actcccatgc acagcctttt gatttccccg atgataacca gaattctaaa |
| 1201 | aaactagctg ctggacatga attacagcca ctagccattg tggaccagcg accttcaagc |
| 1261 | agagccagca gtcgtgccag cagcagacct cggcctgatg acctggagat ctag |

| Table 8B | |
|---|---|
| Human Connexin43 (SEQ.ID.NO: 135) | |
| 1 | atgggtgact ggagcgcctt aggcaaactc cttgacaagg ttcaagccta ctcaactgct |
| 61 | ggagggaagg tgtggctgtc agtactttc attttccgaa tcctgctgct ggggacagcg |
| 121 | gttgagtcag cctggggaga tgagcagtct gcctttcgtt gtaacactca gcaacctggt |
| 181 | tgtgaaaatg tctgctatga caagtctttc ccaatctctc atgtgcgctt ctgggtcctg |
| 241 | cagatcatat ttgtgtctgt acccacactc ttgtacctgg ctcatgtgtt ctatgtgatg |
| 301 | cgaaaggaag agaaactgaa caagaaagag gaagaactca aggttgccca aactgatggt |
| 361 | gtcaatgtgg acatgcactt gaagcagatt gagataaaga gttcaagta cggtattgaa |
| 421 | gagcatggta aggtgaaaat gcgagggggg ttgctgcgaa cctacatcat cagtatcctc |
| 481 | ttcaagtcta tctttgaggt ggccttcttg ctgatccagt ggtacatcta tggattcagc |
| 541 | ttgagtgctg tttacacttg caaaagagat ccctgcccac atcaggtgga ctgtttcctc |
| 601 | tctcgcccca ggagaaaac atcttcatc atcttcatgc tggtggtgtc cttggtgtcc |
| 661 | ctggccttga atatcattga actcttctat gttttcttca agggcgttaa ggatcgggtt |
| 721 | aagggaaaga gcgaccctta ccatgcgacc agtggtgcgc tgagccctgc aaagactgt |
| 781 | gggtctcaaa atatgctta tttcatggc tgctcctcac caaccgctcc cctctcgcct |
| 841 | atgtctcctc ctgggtacaa gctggttact ggcgacagaa acaattcttc ttgccgcaat |
| 901 | tacaacaagc aagcaagtga gcaaaactgg gctaattaca gtgcagaaca aaatcgaatg |
| 961 | gggcaggcgg gaagcaccat ctctaactcc catgcacagc cttttgattt ccccgatgat |
| 1021 | aaccagaatt ctaaaaaact agctgctgga catgaattac agccactagc cattgtggac |
| 1081 | cagcgacctt caagcagagc cagcagtcgt gccagcagca gacctcggcc tgatgacctg |
| 1141 | gagatctag |

Therapeutic Agents

Therapeutic agents include pharmaceutically acceptable agents useful in the treatment of wounds or the promotion of wound-healing, whether currently existing and known or later developed. Therapeutic agents include, for example, anti-infectives, anesthetics, analgesics, antibiotics, narcotics, and steroidal and non-steroidal anti-inflammatory agents. Preferred therapeutic agents include topical steroid anti-inflammatory agents, antimicrobial agents, local and topical anesthetics, and topical opioids. In certain embodiments, one, two three, four, five or six therapeutic agents may be used in combination.

Agents Useful for Wound Healing

As used herein, agents useful for wound healing include stimulators, enhancers or positive mediators of the wound healing cascade which 1) promote or accelerate the natural wound healing process or 2) reduce effects associated with improper or delayed wound healing, which effects include, for example, adverse inflammation, epithelialization, angiogenesis and matrix deposition, and scarring and fibrosis.

Positive mediators, enhancers and stimulators include for example, an agent which may stimulate, enhance, facilitate, or accelerate (i.e., agonize) the quantity, quality or efficacy of wound healing or the active wound healing process, or a wound healing-associated growth factor or cytokine at a wound site, or the activation of a wound healing-associated growth factor or cytokine receptor. Such agents may include a wound healing-associated growth factor or cytokine or a partially modified form of a wound healing-associated growth factor or cytokine, for example. A partially modified form of wound healing-associated growth factor or cytokine may, for example, have a longer half-life than the natural wound healing-associated growth factor or cytokine. Alternatively, it may be an inhibitor of wound healing-associated growth factor or cytokine metabolism.

Partial modification of such an agent may be by way of addition, deletion or substitution of amino acid residues. A substitution may for example be a conserved substitution. Hence a partially modified molecule may be a homologue of the molecule from which it was derived. It may have at least about 40%, for example about 50, 60, 70, 80, 90 or 95%, homology with the molecule from which it is derived.

As used herein, agents useful for wound healing may include for example, wound-healing-promoting or scar-reducing agents for wound treatment modalities now known in the art or later-developed; exemplary factors, agents or modalities including natural or synthetic growth factors, cytokines, or modulators thereof to promote wound healing, wound healing promoting bioengineered matrix, dressings bandages, and the like. Suitable examples may include, but not limited to 1) topical or dressing and related therapies and debriding agents (such as, for example, Santyl® collagenase) and Iodosorb® (cadexomer iodine); 2) antimicrobial agents, including systemic or topical creams or gels, including, for example, silver-containing agents such as SAGs (silver antimicrobial gels), (CollaGUARD™, Innocoll, Inc) (purified type-I collagen protein based dressing), CollaGUARD Ag (a collagen-based bioactive dressing impregnated with silver for infected wounds or wounds at risk of infection), DermaSIL™ (a collagen-synthetic foam composite dressing for deep and heavily exuding wounds); 3) cell therapy or bioengineered skin, skin substitutes, and skin equivalents, including, for example, Dermograft (3-dimensional matrix cultivation of human fibroblasts that secrete cytokines and growth factors), Apligraf® (human keratinocytes and fibroblasts), Graftskin® (bilayer of epidermal cells and fibroblasts that is histologically similar to normal skin and produces growth factors similar to those produced by normal skin), TransCyte (a Human Fibroblast Derived Temporary Skin Substitute) and Oasis® (an active biomaterial that comprises both growth factors and extracellular matrix components such as collagen, proteoglycans, and glycosaminoglycans); 4) cytokines, growth factors or hormones (both natural and synthetic) introduced to the wound to promote wound healing, including, for example, NGF, NT3, BDGF, integrins, plasmin, semaphoring, blood-derived growth factor, keratinocyte growth factor, tissue growth factor, TGF-alpha, TGF-beta, PDGF (one or more of the three subtypes may be used: AA, AB, and B), PDGF-BB, TGF-beta 3, factors that modulate the relative levels of TGFβ3, TGFβ1, and TGFβ2 (e.g., Mannose-6-phosphate), sex steroids, including for example, estrogen, estradiol, or an oestrogen receptor agonist selected from the group consisting of ethinyloestradiol, dienoestrol, mestranol, oestradiol, oestriol, a conjugated oestrogen, piperazine oestrone sulphate, stilboestrol, fosfesterol tetrasodium, polyestradiol phosphate, tibolone, a phytoestrogen, 17-beta-estradiol; thymic hormones such as Thymosin-beta-4, EGF, HB-EGF, fibroblast growth factors (e.g., FGF1, FGF2, FGF7), keratinocyte growth factor, TNF, interleukins family of inflammatory response modulators such as, for example, IL-10, IL-1, IL-2, IL-6, IL-8, and IL-10 and modulators thereof; INFs (INF-alpha, -beta, and -delta); stimulators of activin or inhibin, and inhibitors of interferon gamma prostaglandin E2 (PGE2) and of mediators of the adenosine 3',5'-cyclic monophosphate (cAMP) pathway; adenosine A1 agonist, adenosine A2 agonist or 5) other agents useful for wound healing, including, for example, both natural or synthetic homologues, agonist and antagonist of VEGF, VEGFA, IGF; IGF-1, proinflammatory cytokines, GM-CSF, and leptins and 6) IGF-1 and KGF cDNA, autologous platelet gel, hypochlorous acid (Sterilox® lipoic acid, nitric oxide synthase3, matrix metalloproteinase 9 (MMP-9), CCT-ETA, alphavbeta6 integrin, growth factor-primed fibroblasts and Decorin, silver containing wound dressings, Xenaderm™, papain wound debriding agents, lactoferrin, substance P, collagen, and silver-ORC, placental alkaline phosphatase or placental growth factor, modulators of hedgehog signaling, modulators of cholesterol synthesis pathway, and APC (Activated Protein C), keratinocyte growth factor, TNF, Thromboxane A2, NGF, BMP bone morphogenetic protein, CTGF (connective tissue growth factor), wound healing chemokines, decorin, modulators of lactate induced neovascularization, cod liver oil, placental alkaline phosphatase or placental growth factor, and thymosin beta 4. In certain embodiments, one, two three, four, five or six agents useful for wound healing may be used in combination.

It is to be understood that the agents useful for wound healing (including for example, growth factors and cytokines) above encompass all naturally occurring polymorphs (for example, polymorphs of the growth factors or cytokines). Also, functional fragments, chimeric proteins comprising one of said agents useful for wound healing or a functional fragment thereof, homologues obtained by analogous substitution of one or more amino acids of the wound healing agent, and species homologues are encompassed. It is contemplated that one or more agents useful for wound healing may be a product of recombinant DNA technology, and one or more agents useful for wound healing may be a product of transgenic technology. For example, platelet derived growth factor may be provided in the form of a recombinant PDGF or a gene therapy vector comprising a coding sequence for PDGF.

A fragment or partially modified form thereof refers to a fragment or partially modified form of the wound healing agent which retains the biological or wound healing functionality of the factor, although it may of course have additional functionality. Partial modification may, for example, be by way of addition, deletion or substitution of amino acid residues. For example, a substitution may be a conserved substitution. Hence the partially modified molecules may be homologues of the wound healing agent. They may, for example, have at least about 40% homology with said factor. They may for example have at least about 50, 60, 70, 80, 90 or 95% homology with said factor. For example, in certain embodiments, IL-10 or a fragment or a partially modified form thereof may be administered at a concentration of between about 1 µM and about 10 µM. It may be administered at a concentration of between about 2.5 µM and about 5 µM. In certain other embodiments, IL-10 or a fragment or a partially modified form thereof may be administered immediately prior to wound healing, but may be effective if administered within about 7 days of wounding. It could be administered on at least two occasions.

Gap Junction Modifying Agents

As used herein, "gap junction modifying agent" may broadly include those agents or compounds that prevent, decrease or modulate, in whole or in part, the activity, function, or formation of a hemichannel or a gap junction.

In other embodiments, a gap junction modifying agent prevents or decreases, in whole or in part, the formation or activity of a hemichannel or a gap junction.

In certain embodiments, a gap junction modifying agent induces closure, in whole or in part, of a hemichannel or a gap junction. In other embodiments, a gap junction modifying agent blocks, in whole or in part, a hemichannel or a gap junction. In certain embodiments, a gap junction modifying agent decreases or prevents, in whole or in part, the opening of a hemichannel or gap junction.

In certain embodiments, said blocking or closure of a gap junction or hemichannel by a gap junction modifying agent can reduce or inhibit extracellular hemichannel communication by preventing or decreasing the flow of small molecules through an open channel to and from an extracellular or periplamic space.

In certain embodiments, a gap junction modifying agent prevents, decreases or alters the activity or function of a connexin, a hemichannel or a gap junction. As used herein, modification of the gap junction activity or function may include the opening or closing of gap junctions, opening or closing of connexon hemichannel, and/or passage of molecules or ions through the gap junctions.

In certain another aspect, gap junction modifying agent may include, for example, aliphatic alcohols; octanol; heptanol; anesthetics (e.g. halothane), ethrane, fluothane, propofol and thiopental; anandamide; arylaminobenzoate (FFA: flufenamic acid and similar derivatives that are lipophilic); carbenoxolone; Chalcone: (2',5'-dihydroxychalcone); CHFs (Chlorohydroxyfuranones); CMCF (3-chloro-4-(chloromethyl)-5-hydroxy-2(5H)-furanone); dexamethasone; doxorubicin (and other anthraquinone derivatives); eicosanoid thromboxane A(2) (TXA(2)) mimetics; NO (nitric oxide); Fatty acids (e.g. arachidonic acid, oleic acid and lipoxygenase metabolites; Fenamates (flufenamic (FFA), niflumic (NFA) and meclofenamic acids (MFA)); Genistein; glycyrrhetinic acid (GA):18a-glycyrrhetinic acid and 18-beta-glycyrrhetinic acid, and derivatives thereof; lindane; lysophosphatidic acid; mefloquine; menadione; 2-Methyl-1,4-naphthoquinone, vitamin K(3); nafenopin; okadaic acid; oleamide; oleic acid; PH, gating by intracellular acidification; e.g. acidifying agents; polyunsaturated fatty acids; fatty acid GJIC inhibitors (e.g. oleic and arachidonic acids); quinidine; quinine; all trans-retinoic acid; and tamoxifen.

Exemplary compounds used for altering gap junction functions (e.g., gap junction blocking agents, gap junction protein phosphorylating and dephosphorylating agents) have been previously reported by Jensen et al., see U.S. Pat. No. 7,153,822, Larsen et al., see U.S. Pat. No. 7,250,397, Gourdie et al., see WO2006069181, and Tudor et al., see WO2003032964, and other assorted published patent applications.

As used herein, "gap junction phosphorylating agent" or "gap junction dephosphorylating agent" may include those agents or compounds capable of inducing phosphorylation or de-phosphorylation on connexin residues. Exemplary sites of phosphorylation or dephosphorylation include one or more of a tyrosine, serine or threonine residue on the connexin protein. In certain embodiments, modulation of phosphorylation may occur on one or more residues on one or more connexin proteins. Exemplary gap junction phosphorylating or dephosphorylating agent are well know in the art and may include, for example, c-Src tyrosine kinase or other G protein-coupled receptor agonists. See Giepmans B, *J. Biol. Chem.*, Vol. 276, Issue 11, 8544-8549, Mar. 16, 2001. In one embodiment, modulation of phosphorylation on one or more of these residues impacts hemichannel function, particularly by closing the hemichannel. In another embodiment, modulation of phosphorylation on one or more of these residues impacts gap junction function, particularly by closing the gap junction.

Dosage Forms and Formulations and Administration

A therapeutically effective amount of each of the combination partners (e.g. an anti-connexin agent and a wound healing agent) may be administered simultaneously, separately or sequentially and in any order. The agents may be administered separately or as a fixed combination. When not administered as a fixed combination, preferred methods include the sequential administration of one or more anti-connexin agents and one or more agents useful for wound healing, either or both of which are provided in amounts or doses that are less that those used when the agent or agents are administered alone, i.e., when they are not administered in combination, either physically or in the course of treatment of a wound. Such lesser amounts of agents administered are typically from about one-twentieth to about one-tenth the amount or amounts of the agent when administered alone, and may be about one-eighth the amount, about one-sixth the amount, about one-fifth the amount, about one-fourth the amount, about one-third the amount, and about one-half the amount when administered alone. Preferably, the agents are administered sequentially within at least about one-half hour of each other. The agents may also be administered with about one hour of each other, with about one day to about one week of each other, or as otherwise deemed appropriate. Preferably, the anti-connexin agent is administered first. Preferably, where one or more anti-connexin agents are used, an anti-connexin peptide or anti-connexin peptidomimetic, e.g., an anti-connexin agent that can block or reduce hemichannel opening, is administered prior to the administration of an anti-connexin agent that blocks or reduce connexin expression or the formation of hemichannels or gap junctions, e.g., by downregulation of connexin protein expression. Preferably, the anti-connexin agent or agents is/are anti-connexin 43 agent(s).

The agents of the invention of the may be administered to a subject in need of treatment, such as a subject with any of the diseases or conditions mentioned herein. The condition of the subject can thus be improved. The anti-connexin agent and combinational partner may thus be used in the treatment of the subject's body by therapy. They may be used in the manufacture of a medicament to treat any of the conditions mentioned herein. Thus, in accordance with the invention, there are provided formulations by which cell-cell communication can be downregulated in a transient and site-specific manner.

The anti-connexin agent may be present in a substantially isolated form. It will be understood that the product may be mixed with carriers or diluents which will not interfere with the intended purpose of the product and still be regarded as substantially isolated. A product of the invention may also be in a substantially purified form, in which case it will generally comprise about 90%, e.g. at least about 95%, at least about 98% or at least about 99% of the polynucleotide (or other anti-connexin agent) or dry mass of the preparation.

Depending on the intended route of administration, the pharmaceutical products, pharmaceutical compositions, combined preparations and medicaments of the invention may, for example, take the form of solutions, suspensions, instillations, salves, creams, gels, foams, ointments, emulsions, lotions, paints, sustained release formulations, or powders, and typically contain about 0.1%-95% of active ingredient(s), preferably about 0.2%-70%. Other suitable formulations include pluronic gel-based formulations, carboxymethylcellulose(CMC)-based formulations, and hyroxypropylmethylcellulose(HPMC)-based formulations. Other useful formulations include slow or delayed release preparations.

Gels or jellies may be produced using a suitable gelling agent including, but not limited to, gelatin, tragacanth, or a cellulose derivative and may include glycerol as a humectant, emollient, and preservative. Ointments are semi-solid preparations that consist of the active ingredient incorporated into a fatty, waxy, or synthetic base. Examples of suitable creams include, but are not limited to, water-in-oil and oil-in-water emulsions. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH.

Foam preparations may be formulated to be delivered from a pressurized aerosol canister, via a suitable applicator, using inert propellants. Suitable excipients for the formulation of the foam base include, but are not limited to, propylene glycol, emulsifying wax, cetyl alcohol, and glyceryl stearate. Potential preservatives include methylparaben and propylparaben.

Preferably the agents of the invention are combined with a pharmaceutically acceptable carrier or diluent to produce a pharmaceutical composition. Suitable carriers and diluents include isotonic saline solutions, for example phosphate-buffered saline. Suitable diluents and excipients also include, for example, water, saline, dextrose, glycerol, or the like, and combinations thereof. In addition, if desired substances such as wetting or emulsifying agents, stabilizing or ph buffering agents may also be present.

The term "pharmaceutically acceptable carrier" refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, and amino acid copolymers.

Pharmaceutically acceptable salts can also be present, e.g., mineral acid salts such as hydrochlorides, hydrobromides, phosphates, sulfates, and the like; and the salts of organic acids such as acetates, propionates, malonates, benzoates, and the like.

Suitable carrier materials include any carrier or vehicle commonly used as a base for creams, lotions, gels, emulsions, lotions or paints for topical administration. Examples include emulsifying agents, inert carriers including hydrocarbon bases, emulsifying bases, non-toxic solvents or water-soluble bases. Particularly suitable examples include pluronics, HPMC, CMC and other cellulose-based ingredients, lanolin, hard paraffin, liquid paraffin, soft yellow paraffin or soft white paraffin, white beeswax, yellow beeswax, cetostearyl alcohol, cetyl alcohol, dimethicones, emulsifying waxes, isopropyl myristate, microcrystalline wax, oleyl alcohol and stearyl alcohol.

Preferably, the pharmaceutically acceptable carrier or vehicle is a gel, suitably a nonionic polyoxyethylene-polyoxypropylene copolymer gel, for example, a Pluronic gel, preferably Pluronic F-127 (BASF Corp.). This gel is particularly preferred as it is a liquid at low temperatures but rapidly sets at physiological temperatures, which confines the release of the agent to the site of application or immediately adjacent that site.

An auxiliary agent such as casein, gelatin, albumin, glue, sodium alginate, carboxymethylcellulose, methylcellulose, hydroxyethylcellulose or polyvinyl alcohol may also be included in the formulation of the invention.

Other suitable formulations include pluronic gel-based formulations, carboxymethylcellulose(CMC)-based formulations, and hyroxypropylmethylcellulose(HPMC)-based formulations. The composition may be formulated for any desired form of delivery, including topical, instillation, parenteral, intramuscular, subcutaneous, or transdermal administration. Other useful formulations include slow or delayed release preparations.

Where the anti-connexin agent is a nucleic acid, such as a polynucleotide, uptake of nucleic acids by mammalian cells is enhanced by several known transfection techniques for example those including the use of transfection agents. Such techniques may be used with certain anti-connexin agents, including polynucleotides. The formulation which is administered may contain such transfection agents. Examples of these agents include cationic agents (for example calcium phosphate and DEAE-dextran) and lipofectants (for example Lipofectam™ and Transfectam™), and surfactants.

Where the anti-connexin agent comprises a polynucleotide, conveniently, the formulation further includes a surfactant to assist with polynucleotide cell penetration or the formulation may contain any suitable loading agent. Any suitable non-toxic surfactant may be included, such as DMSO. Alternatively a transdermal penetration agent such as urea may be included.

The effective dose for a given subject or condition can be determined by routine experimentation or other methods known in the art or later developed. For example, in order to formulate a range of dosage values, cell culture assays and animal studies can be used. The dosage of such compounds preferably lies within the dose that is therapeutically effective for at least 50% of the population, and that exhibits little or no toxicity at this level.

The effective dosage of each of the anti-connexin agents employed in the methods and compositions of the invention may vary depending on a number of factors including the particular anti-connexin agent or agents employed, the combinational partner, the mode of administration, the frequency of administration, the condition being treated, the severity of the condition being treated, the route of administration, the needs of a patient sub-population to be treated or the needs of the individual patient which different needs can be due to age, sex, body weight, relevant medical condition specific to the patient.

The dose at which an anti-connexin agent is administered to a patient will depend upon a variety of factors such as the age, weight and general condition of the patient, the condition that is being treated, and the particular anti-connexin agent that is being administered.

A suitable dose may be from about 0.001 to about 100 mg/kg body weight such as about 0.01 to about 40 mg/kg body weight. A suitable dose may however be from about 0.001 to about 0.1 mg/kg body weight such as about 0.01 to about 0.050 mg/kg body weight. Doses from about 1 to 100, 200, 300, 400, and 500 micrograms are appropriate.

For example, in certain embodiments, the anti-connexin agent composition may be applied at about 0.01 micromolar (μM) or 0.05 μM to about 200 μM final concentration at the treatment site and/or adjacent to the treatment site. Preferably, the antisense polynucleotide composition is applied at about 0.05 μM to about 100 μM final concentration, more preferably, the anti-connexin agent composition is applied at about 1.0 μM to about 50 μM final concentration, and more preferably, the anti-connexin agent composition is applied at about 5-10 μM to about 30-50 μM final concentration. Additionally, the combined anti-connexin agent composition is applied at about 8 μM to about 20 μM final concentration, and alternatively the anti-connexin agent composition is applied at about 10 μM to about 20 μM final concentration, or at about 10 to about 15 μM final concentration. In certain other embodiments, the anti-connexin agent is applied at about 10 μM final concentration. In yet another embodiment, the anti-connexin agent composition is applied at about 1-15 μM final concentration. Anti-connexin agent dose amounts include, for example, about 0.1-1, 1-2, 2-3, 3-4, or 4-5 micrograms (μg), from about 5 to about 10 μg, from about 10 to about 15 μg, from about 15 to about 20 μg, from about 20 to about 30 μg, from about 30 to about 40 μg, from about 40 to about 50 μg, from about 50 to about 75 μg, from about 75 to about 100 μg, from about 100 μg to about 250 μg, and from 250 μg to about 500 μg. Dose amounts from 0.5 to about 1.0 milligrams or more or also provided, as noted above. Dose volumes will depend on the size of the site to be treated, and may range, for example, from about 25-100 μL to about 100-200 μL, from about 200-500 μL to about 500-1000 μL. Milliliter doses are also appropriate for larger treatment sites.

Still other dosage levels between about 1 nanogram (ng)/kg and about 100 mg/kg body weight per day of each of the agents described herein. In certain embodiments, the dosage of each of the subject compounds will generally be in the range of about 1 ng to about 1 microgram per kg body weight, about 1 ng to about 0.1 microgram per kg body weight, about 1 ng to about 10 ng per kg body weight, about 10 ng to about 0.1 microgram per kg body weight, about 0.1 microgram to about 1 microgram per kg body weight, about 20 ng to about 100 ng per kg body weight, about 0.001 mg to about 100 mg per kg body weight, about 0.01 mg to about 10 mg per kg body weight, or about 0.1 mg to about 1 mg per kg body weight. In certain embodiments, the dosage of each of the subject compounds will generally be in the range of about 0.001 mg to about 0.01 mg per kg body weight, about 0.01 mg to about 0.1 mg per kg body weight, about 0.1 mg to about 1 mg per kg body weight, about 1 mg to about 10 mg per kg body weight or about 10 mg to about 100 mg per kg body weight. If more than one anti-connexin agent is used, the dosage of each anti-connexin agent need not be in the same range as the other. For example, the dosage of one anti-connexin agent may be between about 0.01 mg to about 10 mg per kg body weight, and the dosage of another anti-connexin agent may be between about 0.1 mg to about 1 mg per kg body weight. Other amounts will be known to those of skill in the art and readily determined.

Conveniently, the anti-connexin agent is administered in a sufficient amount to downregulate expression of a connexin protein, or modulate gap junction formation or connexon opening for at least about 0.5 to 1 hour, at least about 1-2 hours, at least about 2-4 hours, at least about 4-6 hours, at least about 6-8 hours, at least about 8-10 hours, at least about 12 hours, or at least about 24 hours post-administration.

The dosage of each of the anti-connexin agents in the compositions and methods of the subject invention may also be determined by reference to the concentration of the composition relative to the size, length, depth, area or volume of the area to which it will be applied. For example, in certain topical and other applications, e.g., instillation, dosing of the pharmaceutical compositions may be calculated based on mass (e.g. micrograms) of or the concentration in a pharmaceutical composition (e.g. μg/μl) per length, depth, area, or volume of the area of application.

Agents useful for wound healing suitable for the preparation of the pharmaceutical compositions described herein may be prepared and administered using methods as known in the art (see, for example, U.S. Pat. Nos. 7,098,190, 6,319,907, 6,331,298, 6,387,364, 6,455,569, 6,566,339, 6,696,433, 6,855,505, 6,900,181, 7,052,684 and EP1100529 B1. The concentration of each anti-connexin agent and agents useful for wound healing need not be in the same range as the other. Other amounts will be known to those of skill in the art and readily determined. For example, suitable combination dosages and formulations in accordance with various aspects and embodiments as described herein may be administered according to the dosing regimen as described in U.S. Pat. No. 6,903,078 to Lewis entitled "Combination PDGF, KGF, IGF, and IGFBP for wound healing."

The initial and any subsequent dosages administered will depend upon the patient's age, weight, condition, and the disease, wound, disorder or biological condition being treated. Depending on the wound healing agent, the dosage and protocol for administration will vary, and the dosage will also depend on the method of administration selected, for example, local or systemic administration.

The wound healing agent may be applied internally or externally, and may be directed towards any tissue exhibiting a wound. For topical administration of IGF, for example, a zinc oxide formulation can be applied, which induces the local production of IGF, as described in Tarnow et al, *Scand J. Plast Reconstr Hand Surg.* 28: 255-259 (1994). An effective dose of PDGF has been reported to be 5 ng/mm$^2$ or higher when applied topically as described in U.S. Pat. No. 4,861,757, and at least 1 ng/ml local concentration of an isoform of PDGF (for example, PDGF-AA, PDGF-BB, or PDGF-AB), up to about 30 ng/ml local concentration applied to a population of fibroblasts as described in Lepisto et al., *Biochem Biophys Res. Comm* 209: 393-399 (1995). PDGF can be administered in a carboxymethylcellulose gel formulation at concentrations of about 10 µg/gm to about 500 µg/gm of gel, about 20 µg/gm to about 200 µg/gm, and about 30 µg/gm to about 100 µg/gm of gel, optimally about 100 µg/gm of gel. Efficacy of PDGF has been achieved within the range of about 3 µg/ml solution to about 300 µg/ml of solution administered.

About 50 µl of KGF of a concentration of about 5 µg/ml may be effective for wound healing by topical application to epithelial tissue as described in Sotozono et al, *Invest. Opthal. Vis. Science* 36: 1524-29 (1995). As described in U.S. Pat. No. 4,861,757, an effective amount of IGF when co-administered with PDGF is in the range of at least 2.5 ng/mm$^2$ to about 5 ng/mm$^2$, with a ratio of PDGF to IGF in the range of about 1:10 to about 25:1 weight to weight, with the most effective ratios being PDGF to IGF of about 1:1 to about 2:1 weight to weight. IGFBP administered in combination with IGF has been shown to increase wound healing at dose levels of about 5 µg of IGF with about 1.5 µg of phosphorylated IGFBP in a molar ration of about 11:1 IGF:IGFBP, as described in Jyung et al, *Surgery* 115:233-239 (1994).

For administration of polypeptide therapeutics, for example, PDGF, KGF, IGF and IGFBP polypeptides, the dosage can be in the range of about 5 µg to about 50 µg/kg of tissue to which the application is directed, also about 50 µg to about 5 mg/kg, also about 100 µg to about 500 µg/kg of tissue, and about 200 to about 250 µg/kg. For polynucleotide therapeutics, for example in a gene therapy administration protocol, depending on the expression strength the polynucleotide in the patient, for tissue targeted administration, vectors containing expressible constructs including PDGF, KGF, IGF, and IGFBP coding sequences can be administered in a range of about 100 ng to about 200 mg of DNA for local administration in a gene therapy protocol, also about 500 ng to about 50 mg, also about 1 µg to about 2 mg of DNA, about 5 µg of DNA to about 500 µg of DNA, and about 20 µg to about 100 µg during a local administration in a gene therapy protocol, and about 250 µg, per injection or administration. Factors such as method of action and efficacy of transformation and expression are therefore considerations that will effect the dosage required for ultimate efficacy for administration of DNA therapeutics. Where greater expression is desired, over a larger area of tissue, larger amounts of DNA or the same amounts re-administered in a successive protocol of administrations, or several administrations to different adjacent or close tissue portions of for example, a wound site may be required to effect a positive therapeutic outcome.

Therapeutic agents and gap junction modifying agents suitable for the preparation of the pharmaceutical compositions described herein may be formulated and administered using methods as known in the art. The initial and any subsequent dosages administered will depend upon the patient's age, weight, condition, and the disease, wound, disorder or biological condition being treated. Depending on the therapeutic, the dosage and protocol for administration will vary, and the dosage will also depend on the method of administration selected, for example, local or systemic administration.

As noted herein, the doses of either an anti-connexin agent or another agent administered in combination can be adjusted down from the doses administered when given alone.

The combined use of several agents may reduce the required dosage for any individual agent because the onset and duration of effect of the different agents may be complementary. In a preferred embodiment, the combined use of one or more anti-connexin agents and one or more therapeutic agents, agents useful for wound healing, and/or gap junction modifying agents has an additive, synergistic or super-additive effect.

In some cases, the combination of one or more anti-connexin agents and one or more therapeutic agents and/or one or more agents useful for wound healing, and/or one or more gap junction modifying agents have an additive effect. In other cases, the combination can have greater-than-additive effect. Such an effect is referred to herein as a "supra-additive" effect, and may be due to synergistic or potentiated interaction.

The term "supra-additive promotion of wound healing" refers to a mean wound healing produced by administration of a combination of an anti-connexin agent and one or more therapeutic agents, agents useful for wound healing and/or gap junction modifying agents, is statistically significantly higher than the sum of the wound healing produced by the individual administration of either any of the agents alone. Whether produced by combination administration of an anti-connexin agent and one or more therapeutic agents, agents useful for wound healing and/or gap junction modifying agents is "statistically significantly higher" than the expected additive value of the individual compounds may be determined by a variety of statistical methods as described herein and/or known by one of ordinary skill in the art. The term "synergistic" refers to a type of supra-additive inhibition in which both the anti-connexin agent and one or more therapeutic agents, agents useful for wound healing and/or gap junction modifying agents individually have the ability to promote wound healing or reduce fibrosis and scarring. The term "potentiated" refers to type of supra-additive effect in which one of the anti-connexin agent or one or more therapeutic agents, agents useful for wound healing and/or gap junction modifying agents individually has the increased ability to promote wound healing.

In general, potentiation may be assessed by determining whether the combination treatment produces a mean wound healing increase in a treatment group that is statistically significantly supra-additive when compared to the sum of the mean wound healing increases produced by the individual treatments in their treatment groups respectively. The mean wound healing increase may be calculated as the difference between control group and treatment group mean wound healing. The fractional increase in wound healing, "fraction affected" (Fa), may be calculated by dividing the treatment group mean wound healing increase by control group mean wound healing. Testing for statistically significant potentiation requires the calculation of Fa for each treatment group. The expected additive Fa for a combination treatment may be taken to be the sum of mean Fas from groups receiving either element of the combination. The Two-Tailed One-Sample T-Test, for example, may be used to evaluate how likely it is that the result obtained by the experiment is due to chance alone, as measured by the p-value. A p-value of less than 0.05 is considered statistically significant, that is, not likely to be due to chance alone. Thus, Fa for the combination treatment group must be statistically significantly higher than the expected additive Fa for the single element treatment groups to deem the combination as resulting in a potentiated supra-additive effect.

Whether a synergistic effect results from a combination treatment may be evaluated by the median-effect/combination-index isobologram method (Chou, T., and Talalay, P. (1984) Ad. Enzyme Reg. 22:27-55). In this method, combination index (CI) values are calculated for different dose-effect levels based on parameters derived from median-effect plots of the anti-connexin agent alone, the one or more agents useful for wound healing alone, and the combination of the two at fixed molar ratios. CI values of & It; 1 indicate synergy, CI-1 indicates an additive effect, and CP1 indicates an antagonistic effect. This analysis may be performed using computer software tools, such as CalcuSyn, Windows Software for Dose Effect Analysis (Biosoft(D, Cambridge UK).

Any method known or later developed in the art for analyzing whether a supra-additive effect exists for a combination therapy is contemplated for use in screening for suitable anti-connexin agents for use in combination with one or more therapeutic agents, agents useful for wound healing and/or gap junction modifying agents.

In another preferred embodiment, the combined use of one or more anti-connexin agents and one or more therapeutic agents, agents useful for wound healing, and/or gap junction modifying agents reduces the effective dose of any such agent compared to the effective dose when said agent administered alone. In certain embodiments, the effective dose of the agent when used in combination with one or more anti-connexin agents is about $1/15$ to about $1/2$, about $1/10$ to about $1/3$, about $1/8$ to about $1/6$, about $1/5$, about $1/4$, about $1/3$ or about $1/2$ the dose of the agent when used alone.

In another preferred embodiment, the combined use of one or more anti-connexin agents and one or more therapeutic agents, agents useful for wound healing, and/or gap junction modifying agents reduces the frequency in which said agent is administered compared to the frequency when said agent is administered alone. Thus, these combinations allow the use of lower and/or fewer doses of each agent than previously required to achieve desired therapeutic goals.

The doses may be administered in single or divided applications. The doses may be administered once, or application may be repeated.

One or more anti-connexin agents and one or more therapeutic agents, agents useful for wound healing and/or gap junction modifying agents may be administered by the same or different routes. The various agents of the invention can be administered separately at different times during the course of therapy, or concurrently in divided or single combination forms.

In one aspect of the invention the anti-connexin agent is administered in one composition and the therapeutic agent, wound healing agent and/or gap junction modifying agent is administered in a second composition. In one embodiment the first composition comprising one or more anti-connexin agents is administered before the second composition comprising one or more therapeutic agents, agents useful for wound healing and/or gap junction modifying agents. In one embodiment the first composition comprising one or more anti-connexin agents is administered after the second composition comprising one or more therapeutic agents, agents useful for wound healing and/or gap junction modifying agents. In one embodiment the first composition comprising one or more anti-connexin agents is administered before and after the second composition comprising one or more therapeutic agents, agents useful for wound healing and/or gap junction modifying agents. In one embodiment the first composition comprising one or more anti-connexin agents is administered about the same time as the second composition comprising one or more therapeutic agents, agents useful for wound healing and/or gap junction modifying agents.

Preferably one or more anti-connexin agents and one or more therapeutic agents, agents useful for wound healing and/or gap junction modifying agents are delivered by topical administration (peripherally or directly to a site), including but not limited to topical administration using solid supports (such as dressings and other matrices) and medicinal formulations (such as gels, mixtures, suspensions and ointments). In one embodiment, the solid support comprises a biocompatible membrane or insertion into a treatment site. In another embodiment, the solid support comprises a dressing or matrix. In one embodiment of the invention, the solid support composition may be a slow release solid support composition, in which the one or more anti-connexin agents and one or more therapeutic agents, agents useful for wound healing and/or gap junction modifying agents is dispersed in a slow release solid matrix such as a matrix of alginate, collagen, or a synthetic bioabsorbable polymer. Preferably, the solid support composition is sterile or low bio-burden. In one embodiment, a wash solution comprising one or more anti-connexin agents can be used.

The delivery of one or more anti-connexin agents and one or more therapeutic agents, agents useful for wound healing and/or gap junction modifying agents of the formulation over a period of time, in some instances for about 1-2 hours, about 2-4 hours, about 4-6 hours, about 6-8, or about 24 hours or longer, may be a particular advantage in more severe injuries or conditions. In some instances, cell loss may extend well beyond the site of a procedure to surrounding cells. Such loss may occur within 24 hours of the original procedure and is mediated by gap junction cell-cell communication. Administration of anti-connexin agent(s), e.g., for downregulation of connexin expression, or blockade of connexon opening, therefore will modulate communication between the cells, or loss into the extracellular space in the case of connexon regulation, and minimize additional cell loss or injury or consequences of injury.

While the delivery period will be dependent upon both the site at which the downregulation is to be induced and the therapeutic effect which is desired, continuous or slow-release delivery for about 1-2 hours, about 2-4 hours, about 4-6 hours, about 6-8, or about 24 hours or longer is provided. In accordance with the present invention, this is achieved by inclusion of the anti-connexin agents and/or one or more therapeutic agents, agents useful for wound healing and/or gap junction modifying agents in a formulation together with a pharmaceutically acceptable carrier or vehicle, particularly in the form of a formulation for continuous or slow-release administration.

As noted, the one or more agents of the invention may be administered before, during, immediately following wounding, for example, or within about 180, about 120, about 90, about 60, or about 30 days, but preferably within about 10, about 9, about 8, about 7, about 6, about 5, about 4, about 3, or about 2 days or less, and most preferably within about 24, about 12, about 10, about 9, about 8, about 7, about 6, about 5, about 4, about 3, about 2 hours or within about 60, about 45, about 30, about 15, about 10, about 5, about 4, about 3, about 2, about 1 minute following wounding, for example.

The routes of administration and dosages described herein are intended only as a guide since a skilled physician will determine the optimum route of administration and dosage for any particular patient and condition.

Any of the methods of treating a subject having or suspected of having or predisposed to, or at risk for, a disease, disorder, and/or condition, referenced or described herein may utilize the administration of any of the doses, dosage forms, formulations, and/or compositions herein described.

Dressings and Matrices

In one aspect, the one or more anti-connexin agents, one or more therapeutic agents, agents useful for wound healing and/or gap junction modifying agents are provided in the form of a dressing or matrix. In certain embodiments, the one or more agents of the invention are provided in the form of a liquid, semi solid or solid composition for application directly, or the composition is applied to the surface of, or incorporated into, a solid contacting layer such as a dressing gauze or matrix. The dressing composition may be provided for example, in the form of a fluid or a gel. The one or more anti-connexin agents and one or more therapeutic agents, agents useful for wound healing and/or gap junction modifying agents may be provided in combination with conventional pharmaceutical excipients for topical application. Suitable carriers include: Pluronic gels, Polaxamer gels, Hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols). Suitable carriers also include creams/ointments used for topical pharmaceutical preparations, e.g., creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilizers such as EDTA.

Suitable dressings or matrices may include, for example, the following with one or more anti-connexin agents with one or more therapeutic agents, agents useful for wound healing and/or gap junction modifying agents:

1) Absorptives:

suitable absorptives may include, for example, absorptive dressings, which can provide, for example, a semi-adherent quality or a non-adherent layer, combined with highly absorptive layers of fibers, such as for example, cellulose, cotton or rayon. Alternatively, absorptives may be used as a primary or secondary dressing.

2) Alginates:

suitable alginates include, for example, dressings that are non-woven, non-adhesive pads and ribbons composed of natural polysaccharide fibers or xerogel derived from seaweed. Suitable alginates dressings may, for example, form a moist gel through a process of ion exchange upon contact with exudate. In certain embodiments, alginate dressings are designed to be soft and conformable, easy to pack, tuck or apply over irregular-shaped areas. In certain embodiments, alginate dressings may be used with a second dressing.

3) Antimicrobial Dressings:

suitable antimicrobial dressings may include, for example, dressings that can facilitate delivery of bioactive agents, such as, for example, silver and polyhexamethylene biguanide (PHMB), to maintain efficacy against infection, where this is needed or desirable. In certain embodiments, suitable antimicrobial dressings may be available as for example, as sponges, impregnated woven gauzes, film dressings, absorptive products, island dressings, nylon fabric, non-adherent barriers, or a combination of materials.

4) Biological & Biosynthetics:

suitable biological dressings or biosynthetic dressings may include, for example, gels, solutions or semi-permeable sheets derived from a natural source. In certain embodiments, a gel or solution is applied to the treatment site and covered with a dressing for barrier protection. In another embodiment, a sheet is placed in situ which may act as membrane, remaining in place after a single application.

5) Collagens:

suitable collagen dressings may include, for example, gels, pads, particles, pastes, powders, sheets or solutions derived from for example, bovine, porcine or avian sources or other natural sources or donors. In certain embodiments, the collagen dressing may interact with treatment site exudate to form a gel. In certain embodiments, collagen dressing may be used in combination with a secondary dressing.

6) Composites:

suitable composite dressings may include, for example, dressings that combine physically distinct components into a single product to provide multiple functions, such as, for example, a bacterial barrier, absorption and adhesion. In certain embodiment, the composite dressings are comprised of, for example, multiple layers and incorporate a semi- or non-adherent pad. In certain embodiment, the composite may also include for example, an adhesive border of non-woven fabric tape or transparent film. In certain other embodiment, the composite dressing may function as for example, either a primary or a secondary dressing and in yet another embodiment, the dressing may be used in combination with topical pharmaceutical composition.

7) Contact Layers:

suitable contact layer dressings may include, for example, thin, non-adherent sheets placed on an area to protect tissue from for example, direct contact with other agents or dressings applied to the treatment site. In certain embodiments, contact layers may be deployed to conform to the shape of the area of the treatment site and are porous to allow exudate to pass through for absorption by an overlying, secondary dressing. In yet another embodiment, the contact layer dressing may be used in combination with topical pharmaceutical composition.

8) Elastic Bandages:

suitable elastic bandages may include, for example, dressings that stretch and conform to the body contours. In certain embodiment, the fabric composition may include for example, cotton, polyester, rayon or nylon. In certain other embodiments, the elastic bandage may for example, provide absorption as a second layer or dressing, to hold a cover in place, to apply pressure or to cushion a treatment site.

9) Foams:

suitable foam dressings may include, for example, sheets and other shapes of foamed polymer solutions (including polyurethane) with small, open cells capable of holding fluids. Exemplary foams may be for example, impregnated or layered in combination with other materials. In certain embodiment, the absorption capability may be adjusted based on the thickness and composition of the foam. In certain other embodiments, the area in contact with the treatment site may be non-adhesive for easy removal. In yet another embodiment, the foam may be used in combination with an adhesive border and/or a transparent film coating that can serve as an anti-infective barrier.

10) Gauzes & Non-Woven Dressings:

suitable gauze dressings and woven dressings may include, for example, dry woven or non-woven sponges and wraps with varying degrees of absorbency. Exemplary fabric composition may include, for example, cotton, polyester or rayon. In certain embodiment, gauzes and non-woven dressing may be available sterile or non-sterile in bulk and with or without an adhesive border. Exemplary gauze dressings and woven dressings may be used for cleansing, packing and covering a variety of treatment sites.

11) Hydrocolloids:

suitable hydrocolloid dressings may include, for example, wafers, powders or pastes composed of gelatin, pectin or carboxymethylcellulose. In certain embodiment, wafers are self-adhering and available with or without an adhesive border and in a wide variety of shapes and sizes. Exemplary hydrocolloids are useful on areas that require contouring. In certain embodiments, powders and pastes hydrocolloids may use used in combination with a secondary dressing.

12) Hydrogels (Amorphous):

suitable amorphous hydrogel dressings may include, for example, formulations of water, polymers and other ingredients with no shape, designed to donate moisture and to maintain a moist healing environments and or to rehydrate the treatment site. In certain embodiment, hydrogels may be used in combination with a secondary dressing cover.

13) Hydrogels:

Impregnated Dressings: suitable impregnated hydrogel dressings may include, for example, gauzes and non-woven sponges, ropes and strips saturated with an amorphous hydrogel. Amorphous hydrogels may include for example, formulations of water, polymers and other ingredients with no shape, designed to donate moisture to a dry treatment site and to maintain a moist healing environment.

14) Hydrogel Sheets:

suitable hydrogel sheets may include for example, three-dimensional networks of cross-linked hydrophilic polymers that are insoluble in water and interact with aqueous solutions by swelling. Exemplary hydrogels are highly conformable and permeable and can absorb varying amounts of drainage, depending on their composition. In certain embodiment, the hydrogel is non-adhesive against the treatment site or treated for easy removal.

15) Impregnated Dressings:

suitable impregnated dressings may include, for example, gauzes and non-woven sponges, ropes and strips saturated with a solution, an emulsion, oil, gel or some other pharmaceutically active compound or carrier agent, including for example, saline, oil, zinc salts, petrolatum, xeroform and scarlet red as well as the compounds described herein.

16) Silicone Gel Sheets:

suitable silicone gel sheet dressings may include, for example, soft covers composed of cross-linked polymers reinforced with or bonded to mesh or fabric.

17) Solutions:

suitable liquid dressings may include, for example, mixtures of multiprotein material and other elements found in the extracellular matrix. In certain embodiment, exemplary solutions may be applied to the treatment site after debridement and cleansing and then covered with an absorbent dressing or a nonadherent pad.

18) Transparent Films:

suitable transparent film dressings may include polymer membranes of varying thickness coated on one side with an adhesive. In certain embodiments, transparent films are impermeable to liquid, water and bacteria but permeable to moisture vapor and atmospheric gases. In certain embodiments, the transparency allows visualization of the treatment site.

19) Fillers:

suitable filler dressings may include, for example, beads, creams, foams, gels, ointments, pads, pastes, pillows, powders, strands or other formulations. In certain embodiment, fillers are non-adherent and may include a time-released antimicrobial. Exemplary fillers may be useful to maintain a moist environment, manage exudate, and for treatment of for example, partial- and full-thickness wounds, infected wounds, draining wounds and deep wounds that require packing.

Combination Wound Treatment

General Aspects

The present invention is directed to pharmaceutical compositions and their methods of use wherein the composition comprises therapeutically effective amounts of one or more anti-connexin agents and one or more therapeutic agents, agents useful for wound healing and/or gap junction modifying agents. The compositions are useful in enhancing or promoting healing of wounds, such wounds include wounds which may be slow to heal or refractory to conventional wound treatment or wound healing promoting therapies.

Equally, in instances of other tissue damage (particularly wounds) the methods and compositions of the invention are effective in promoting the wound healing process, reducing swelling and inflammation, and in minimizing scar formation. The formulations have clear benefit in the treatment of wounds, whether the result of external trauma (including burns), internal trauma, or surgical intervention, as well as chronic wounds.

Compositions

Accordingly, in one aspect, the invention provides compositions for use in therapeutic treatment, which comprises: at least one anti-connexin agent and at least one therapeutic agent, and/or wound healing agent and/or gap junction modifying agent. In a preferred embodiment, the composition further comprises a pharmaceutically acceptable carrier or vehicle.

In one preferred form, the composition contains one or more antisense polynucleotides to the mRNA of one connexin protein only. In another preferred form, the composition comprises one or more anti-connexin peptides or pepidomimetics. Most preferably, this connexin protein is connexin 43.

The compositions may comprise polynucleotides or anti-connexin peptides to more than one connexin protein. Preferably, one of the connexin proteins to which polynucleotides or anti-connexin peptides are directed is connexin 43. Other connexins to which the polynucleotides or anti-connexin peptides are directed may include, for example, connexins 26, 30, 30.3, 31.1, 32, 36, 37, 40, 40.1, 44.6, 45 and 46. Suitable exemplary polynucleotides (and ODNs) directed to various connexins are set forth in Table 1. Suitable anti-connexin peptides are also provided herein.

Exemplary Combinations

Exemplary combinations of an anti-connexin agent and a wound healing agent according to the compositions and methods of the present invention include the following:

(a) One of the Following Anti-Connexin Agents:
a connexin 43 antisense polynucleotide;
a connexin 43 antisense ODN;
a polynucleotide comprising SEQ. ID. NO: 2;
an ODN comprising SEQ. ID. NO: 2;
a polynucleotide comprising SEQ. ID. NO: 1;
an ODN comprising SEQ. ID. NO: 1:
a connexin 43 RNAi polynucleotide; or
a connexin 43 siRNA polynucleotide; and (b) One of the Following Agents Useful for Wound Healing:
Activin;
FGF-2 or fibroblast growth factor 2;

FGF-1 or fibroblast growth factor-1;
VEGF or vascular endothelial growth factor;
GM-SF or granulocyte monocyte stimulating factor;
Platelet factor 4;
EGF or epidermal growth factor;
TGF or transforming growth factor beta (e.g. TGF-1,2,3);
TNF alpha or tumor necrosis factor alpha;
IL-1 interleukin-1;
IL-4 interleukin-4;
IL-7 interleukin-7;
IL-8 interleukin-8;
IL-10 interleukin-10;
GMCSF or granulocyte-macrophage/colony-stimulating factor;
CTGF or Connective tissue growth factor;
Thymosin beta 4;
IGF-1 or insulin-like growth factor-1;
PDGF or platelet-derived growth factor;
PDGF-BB or platelet-derived growth factor BB;
Mannose-6-phosphate;
(aFGF) Acidic fibroblast growth factor
(bFGF) Basic fibroblast growth factor
(HB-EGF) Heparin binding epidermal growth factor
(hGH) Human growth hormone
(KGF) Keratinocyte growth factor
(KGF-2) Keratinocyte growth factor-2
(MMP) Matrix metalloproteinase
(PDECGF) Platelet-derived endothelial cell growth factor
(PDEGF) Platelet-derived epidermal growth factor
(rbbFGF) Recombinant bovine basic fibroblast growth factor
(rhbFGF) Recombinant human basic fibroblast growth factor
(rhPDGF-BB) Recombinant human platelet-derived growth factor (BB-dimer)
(TGF-alpha) Transforming growth factor-alpha
(TGF-beta) Transforming growth factor-beta
(TIMP) Tissue inhibitor of matrix metalloproteinase
(VEGF) Vascular endothelial growth factor
(IGFBP) Insulin-Like Growth Factor Binding Protein (e.g., IGFBP-2, IGFBP-3, IGFBP-4); and,
(FGF) or fibroblast growth factors (e.g. FGF-1, FGF-2).

This listing of combinations is exemplary in nature. Other combinations of anti-connexin agents and therapeutic agents described herein are also included. Other combinations of anti-connexin agents and agents useful for wound healing described herein are also included. Other combinations of anti-connexin agents and gap junction modifying agents described herein are also included.

Kits, Medicaments and Articles of Manufacturer

Optionally, one or more anti-connexin agents and one or more agents useful for wound healing, therapeutic agents, and/or gap junction modifying agents (e.g., peptides, proteolytic inhibitors, extracellular matrix components, fragments and peptides, steroids, cytokines, oxygen donators or vitamins) may also be used in the manufacture of the medicament.

In one aspect, the invention provides a kit comprising one or more compositions or formulations described. For example, the kit may include a composition comprising an effective amount of one or more anti-connexin agents and one or more therapeutic agents, agents useful for wound healing and/or gap junction modifying agents.

Articles of manufacturer are also provided, comprising a vessel containing a composition or formulation of the invention as described herein and instructions for use for the treatment of a subject. For example, In another aspect, the invention includes an article of manufacture comprising a vessel containing a therapeutically effective amount of one or more pharmaceutically acceptable anti-connexin agents and one or more pharmaceutically acceptable therapeutic agents for promotion or improvement of wound healing and instructions for use, including use for the treatment of a subject.

Treatment

The compositions and formulations of the invention may be used in conjunction or combination with a composition for promoting the healing of wounds or to reduce swelling, inflammation and/or scarring. The compositions and formulations of the invention may also be used in conjunction or combination with a composition for promoting and/or improving the healing of acute or chronic wounds. In one aspect, the wound will be the result of surgery or trauma.

Suitable therapeutic agents, agents useful for wound healing, and/or gap junction modifying agents used in combination with one or more anti-connexin agents for the treatment of wounds are described herein. In one aspect, the anti-connexin agent may be administered in combination with an agent useful for wound healing such as a chemokine, a cytokine, growth factor, or combination thereof. In one embodiment, the chemokine is a chemokine ligand 2 (Ccl2) antagonist. In another embodiment, the cytokine is a tumor necrosis factor alpha (TNF-α) antagonist. In another embodiment, the cytokine is IL-10. In one embodiment, the growth factor is TGF-beta-3. According to another embodiment the wound healing agent is thymosin β4. In yet another embodiment, the anti-connexin agent may be administered in combination with one or more of IGFBP-2, IGF-7, IGF-1 or modulators thereof, to increase hydroxyproline and collagen type 1α1 synthesis for the promotion of wound healing.

Suitable anti-connexin agents for use in combination with an agent useful for wound healing, a therapeutic agent or a gap-junction modifying agent are described herein and may include, for example, a polynucleotide such as an ODN, a blocker or other connexin binding agent such as, for example, receptor mimetic peptide; an absorber to remove activity, such as, for example, synthetically expressed receptor molecules or mimetics; or antibodies; as wells as, for examples, other agents useful to adjust gap junction closing/opening, such as compounds that phosphorylate or dephosphorylate gap junctions.

In one aspect the invention is directed to a method of promoting or improving wound healing in a subject, comprising administration a therapeutically effective amount of one or more anti-connexin agents and one or more therapeutic agents, agents useful for wound healing and/or a gap junction modifying agents or compounds useful for promoting or improving healing. In certain embodiments, the administration of one or more anti-connexin agents and one or more therapeutic agents, agents useful for wound healing and/or a gap junction modifying agents, is effective to reduce inflammation, reduce neutrophil and/or macrophage infiltration into the wound, reduce granulation tissue deposition, promote cell migration to accelerate wound closure and healing, to facilitate epitheliam growth, tissue engineering, and surface recovery for burns, or any combination thereof. In certain embodiments, the administration of one or more anti-connexin agents and one or more therapeutic agents, agents useful for wound healing and/or a gap junction modifying agents, is effective to reduce or prevent scar formation. In methods to promote or improve scar formation, the anti-connexin agent is preferably administered in combination with, or after or prior to, administration of TGF-beta-3 or IL-10 or mannose-6-phosphate.

In one aspect the invention is directed to a method of promoting or improving wound healing in a subject, comprising administration of one or more anti-connexin agents and one or more therapeutic agents, agents useful for wound healing and/or a gap junction modifying agents, in an amount effective to regulate epithelial basal cell division and growth. In one embodiment, the anti-connexin agent is a connexin antisense polynucleotide effective to regulate epithelial basal cell division and growth. In one embodiment, the connexin antisense polynucleotide is a connexin 26 antisense polynucleotide, a connexin 43 antisense polynucleotide, or a mixture thereof.

In one aspect the invention is directed to a method of promoting or improving wound healing, comprising administration of one or more anti-connexin agents and one or more therapeutic agents, agents useful for wound healing and/or a gap junction modifying agents, in an amount effective to regulate outer layer keratin secretion. In one embodiment, the anti-connexin agent is a connexin antisense polynucleotide effective to regulate outer layer keratin secretion. In one embodiment, the connexin antisense polynucleotide is a connexin 43 antisense polynucleotide, a 31.1 antisense polynucleotide, or a mixture thereof.

In yet a further aspect, the invention provides a method of decreasing scar formation and/or improving scar appearance in a patient who has suffered a wound, e.g., a surgical wound (such as in, for example, cosmetic and other surgeries), which comprises the step of administering one or more anti-connexin agents and one or more therapeutic agents, agents useful for wound healing and/or a gap junction modifying agents to said wound to downregulate expression of one or more connexin protein(s) at and immediately adjacent the site of said wound. Again, the wound may be the result of trauma or surgery, with the formulation being applied to the wound immediately prior to surgical repair and/or closure thereof. As noted herein, in methods to reduce or improve scar formation or appearance, the anti-connexin agent is preferably administered in combination with, or after or prior to, administration of a suitable amount of TGF-beta-3 or IL-10 or mannose-6-phosphate.

In one aspect the invention is directed to a method of reducing, preventing or ameliorating tissue damage in a subject, comprising administration of one or more anti-connexin agents and one or more therapeutic agents, agents useful for wound healing and/or a gap junction modifying agents.

In a further aspect, the invention is directed to a method of reducing swelling and/or inflammation as part of treating a wound and/or tissue subjected to physical trauma which comprises the step of administering an anti-connexin composition or formulation as defined above and one or more therapeutic agents, agents useful for wound healing, and/or gap junction modifying agents to or proximate to said wound or tissue. In one embodiment the wound is the result of physical trauma to tissue, including neuronal tissue such as the brain, spinal cord or optic nerve, or skin or eye.

In one aspect the invention is directed to sustained administration of one or more anti-connexin agents and one or more therapeutic agents, agents useful for wound healing, and/or gap junction modifying agents. In one embodiment, an anti-connexin agent is administered for at least about 1-24 hours, at least about 2, hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours or at least about 24 hours. In one embodiment, connexin expression is downregulated over a sustained period of time. Preferably connexin 43 expression is downregulated for a sustained period of time. Conveniently, connexin 43 expression is downregulated for at least about 2, 4, 6, 8, 10, 12, or 24 hours. According to one embodiment, the wound is a chronic wound. Suitable subjects include a diabetic subject.

In one aspect, the present invention provides a method of treating a subject having a wound which comprises sustained administration of an effective amount of an anti-connexin agent and one or more therapeutic agents, agents useful for wound healing, and/or gap junction modifying agents to the wound. In a further aspect, the present invention provides a method of promoting or improving wound healing in a subject which comprises sustained administration of one or more anti-connexin agents and one or more therapeutic agents, agents useful for wound healing, and/or gap junction modifying agents to a wound. In a further aspect, the present invention provides a method of reducing, preventing or ameliorating swelling and/or inflammation in a subject which comprises sustained administration of one or more anti-connexin agents and one or more therapeutic agents, agents useful for wound healing, and/or gap junction modifying agents to a wound. In a further aspect, the present invention provides a method of reducing, preventing or ameliorating scar formation in a subject which comprises sustained administration of one or more anti-connexin agents and one or more therapeutic agents, agents useful for wound healing, and/or gap junction modifying agents to a wound.

According to another further aspect, the present invention provides a method of promoting or improving wound healing in a subject having a wound which comprises sustained administration of an anti-connexin composition or formulation of the present invention and one or more therapeutic agents, agents useful for wound healing, and/or gap junction modifying agents to a wound area in an amount effective to increase re-epithlialization rates in the wound area. In one embodiment the method comprises sustained administration of a connexin 43 antisense polynucleotide and/or a connexin 31.1 antisense polynucleotide and one or more therapeutic agents, wound healing agents and/or gap junction modifying agents. In one embodiment, the composition or compositions are administered in a sustained release formulation. In another embodiment, the composition or compositions are administered for a sustained period of time. Conveniently, the composition is effective to decrease connexin 43 and/or 31.1 levels or activity (e.g., hemichannel or gap junction activity) for at least about 24 hours. According to one embodiment, the wound is a chronic wound. Subjects which may be treated include diabetic subjects.

In yet another aspect, the present invention provides invention provides a method of promoting or improving wound healing in a subject having a wound which comprises sustained administration of an anti-connexin composition or formulation of the present invention and one or more therapeutic agents, agents useful for wound healing, and/or gap junction modifying agents to a wound area in an amount effective to effective to regulate epithelial basal cell division and growth and/or effective to regulate outer layer keratin secretion. In one embodiment, the composition comprises a connexin antisense polynucleotide effective to regulate epithelial basal cell division or growth, preferably a connexin 26 antisense polynucleotide, a connexin 43 antisense polynucleotide, or a mixture thereof. In one embodiment, the composition comprises a connexin antisense polynucleotide effective to regulate outer layer keratinization, preferably, a connexin 31.1 antisense polynucleotide. In one embodiment, the composition or compositions are administered in a sustained release formulation. In another embodiment, the composition or compositions are administered for a sustained period of time. Conveniently, the composition is effective to decrease connexin 43, 26, and/or 31.1 levels for at least about 24 hours. According to one embodiment, the wound is a chronic wound. Subjects which may be treated include diabetic subjects.

In another aspect, methods for treating a subject having a chronic wound are provided. Such methods include administering to the subject an anti-connexin agent capable of inhibiting the expression, formation, or activity of a connexin, or a connexin hemichannel, in combination with one or more therapeutic agents, wound healing agents and/or gap junction modifying agents.

In one aspect the invention is directed to a method for treatment or prophylaxis of a chronic wound comprising administering to a subject in need thereof an effective amount of an anti-connexin agent administered to said chronic wound or a tissue associated with said chronic wound in combination with one or more therapeutic agents, agents useful for wound healing and/or gap junction modifying agents. In another embodiment, the chronic wound is a chronic skin wound and a composition of the present invention is administered to the skin or a tissue associated with the skin of said subject for an effective period of time. A chronic skin wound suitable for treatment may, for example, be selected from the group consisting of pressure ulcers, diabetic ulcers, venous ulcers, arterial ulcers, vasculitic ulcers, and mixed ulcers. The chronic wound may be an arterial ulcer which comprises ulcerations resulting from complete or partial arterial blockage. The chronic wound may be a venous stasis ulcer which comprises ulcerations resulting from a malfunction of the venous valve and the associated vascular disease. The chronic wound may be a trauma-induced ulcer.

In one embodiment, the anti-connexin agent is administered in combination with a growth factor. Preferably the growth factor is PDGF, EGF, or FGF (e.g., FGF-2).

When not administered as a fixed combination, preferred methods include the sequential administration of one or more anti-connexin agents and one or more growth factors. Preferably, the agents are administered sequentially within at least about one-half hour of each other. The agents may also be administered with about one hour of each other, with about one day to about one week of each other, or as otherwise deemed appropriate. Preferably, the anti-connexin agent is administered first. Preferably, where one or more anti-connexin agents are used, an anti-connexin peptide or anti-connexin peptidomimetic, e.g., an anti-connexin agent that can block or reduce hemichannel opening, is administered prior to the administration of an anti-connexin agent that blocks or reduce connexin expression or the formation of hemichannels or gap junctions, e.g., by downregulation of connexin protein expression. Preferably, the anti-connexin agent or agents is/are anti-connexin 43 agent(s).

In another embodiment for treatment of wounds, including chronic wounds, either or both of the one or more anti-connexin agents and one or more growth factors are provided in amounts or doses that are less that those used when the agent or agents are administered alone, i.e., when they are not administered in combination, either physically or in the course of treatment of a wound. Such lesser amounts of agents administered are typically from about one-twentieth to about one-tenth the amount or amounts of the agent when administered alone, and may be about one-eighth the amount, about one-sixth the amount, about one-fifth the amount, about one-fourth the amount, about one-third the amount, and about one-half the amount when administered alone.

In one embodiment the method for treatment or prophylaxis of a chronic wound comprises sustained administration of one or more anti-connexin agents and one or more therapeutic agents, agents useful for wound healing and/or gap junction modifying agents. In one embodiment, the composition or compositions are administered in a sustained release formulation. In another embodiment, the composition or compositions are administered for a sustained period of time. Conveniently, the composition is effective to decrease connexin 43 levels, or block or reduce connexin 43 hemichannel opening, for at least about 1-2 hours, about 2-4 hours, about 4-6 hours, about 4-8 hours, about 12 hours, about 18 hours, or about 24 hours. Subjects which may be treated include diabetic subjects, and patients with other ulcers, including venous ulcers and others described herein and known in the art.

The following examples which will be understood to be provided by way of illustration only and not to constitute a limitation on the scope of the invention.

EXAMPLES

Example 1

Wound healing was assessed using a model with 1.6 mm diameter full thickness excisional wounds on 8 week old mice. Followed by immunohistochemistry and histology, with RT-PCR analysis of gene expression.

Skin wounds repair by a combination of re-epithelializing action and, connective tissue contraction followed by an angiogenic response which leads to a dense network of blood vessels in the wound granulation tissue (Grose, R. and Werner, S. (2004). Wound-healing studies in transgenic and knockout mice. *Mol Biotechnol* 28, 147-66.). A robust inflammatory response commences soon after any tissue damage. This both protects the wound from microbial infection and produces many kinds of bioactive substances that act on the host cells at the wound site. A variety of inflammatory cells migrate into the wound fulfilling several different functions. Neutrophils are the earliest leukocytes to be recruited to the wound and their main role is to defend the host from invasion by microbes, which they do by releasing toxic free oxygen radicals and secreting proinflammatory cytokines. Subsequently, macrophages clear away spent neutrophils and other cell and extracellular matrix debris at the wound site. Macrophages are also the major producers of cytokines, chemokines and growth factors that will direct subsequent cell and tissue migration of the repair response. Whilst many of the signals regulating the inflammation and tissue repair process are clearly diffusible and operate over long distances, local cell-cell communication via cell adhesion molecules and cell-cell junctions appears also to play a significant role.

One junctional link between cells which may play a significant regulatory role is the gap junction which is a hexameric channel formed of proteins from the connexin family. Gap junctions are reported to be expressed by almost all cells in the body (Wei, C. J., Xu, X. and Lo, C. W. (2004). *Annu Rev Cell Dev Biol* 20, 811-38.) and have been reported to mediate changes in cell migration.

The level of connexin 43 (Cx43) protein at the epidermal wound edge has been reported to naturally decreases over 24-48 hours. Downregulating Cx43 protein levels by application of antisense oligodeoxynucleotides (asODN) to skin wound and burn injury sites has been reported to lead to significantly accelerated healing compared with control sense oligodeoxynucleotides (sODN) treated wounds (Qiu, C., Coutinho, P., Frank, S., Franke, S., Law, L. Y., Martin, P., Green, C. R. and Becker, D. L. (2003). Targeting connexin 43 expression accelerates the rate of wound repair. Curr Biol 13, 1697-703; Coutinho, P., Qiu, C., Frank, S., Wang, C. M., Brown, T., Green, C. R. and Becker, D. L. (2005). Limiting burn extension by transient inhibition of connexin 43 expression at the site of injury. Br J Plast Surg 58, 658-67).

The experiments showed that acute downregulation of Cx43 protein at a wound site led to an increase in keratinocyte proliferation and migration, and in the rate at which fibroblasts migrate into the wound and lay down collagen matrix. We noted a decrease in neutrophil infiltration and a concomitant reduction in chemokine ligand 2 (Ccl2) and cytokine tumor necrosis factor alpha (TNF-α) mRNA. Subsequently, we also noted a reduced recruitment of macrophages which may be a consequence of damping down of the initial inflammatory response, which is known to have downstream effects on the ensuing wound healing process. Together these modified responses resulted in significantly improved wound healing.

Wound Model and ODN Treatment

Male, 8 week old, ICR mice were used in the following experiments. All the mice were kept under specific pathogen-free conditions in an environmentally controlled clean room at University College London and all the experiments were carried out under UK Home Office regulations. Mice were anaesthetized by halothane inhalation. Four full-thickness excisional wounds of 6 mm diameter were made on the shaved back on either side of the dorsal midline with a 6 mm biopsy punch (Kai Industries). To each pair of wounds a single topical application of 50 μl of 1 μM Cx43 as ODN (SEQ. ID No. 2) (Sigma-Genosys) in 30% Pluronic F-127 gel (Sigma-Aldrich), chilled on ice, was made to one wound, and an identical application of 1 μM sense control sODNs was made to the other. Cx43 asODNs application results in a significant knockdown of Cx43 protein at the site of delivery within two hours (Becker, D. L., McGonnell, I., Makarenkova, H. P., Patel, K., Tickle, C., Lorimer, J. and Green, C. R. (1999). Roles for alpha 1 connexin in morphogenesis of chick embryos revealed using a novel antisense approach. Dev Genet 24, 33-42; McGonnell, I. M., Green, C. R., Tickle, C. and Becker, D. L. (2001). Connexin 43 gap junction protein plays an essential role in morphogenesis of the embryonic chick face. Dev Dyn 222, 420-38; Qiu, C., Coutinho, P., Frank, S., Franke, S., Law, L. Y., Martin, P., Green, C. R. and Becker, D. L. (2003). Targeting connexin 43 expression accelerates the rate of wound repair. Curr Biol 13, 1697-703). Each wound region was digitally photographed at the indicated time intervals, and the areas of the wounds were calculated. All wound areas were expressed as percentages of the initial wound areas. In some series of experiments, wounds and their surrounding area, including the scab and epithelial margins, were harvested with an 8 mm biopsy punch (Kai Industries) at the indicated time intervals after mice were killed with an overdose of chloroform. A minimum of eight mice were used for each time point examined.

Histology and Immunostaining

Wound tissues were fixed in 4% formaldehyde buffered with PBS, and embedded in paraffin. Sections (6 μm thick) were subjected to hematoxylin and eosin staining or immunostaining. Measurement of granulation tissue area in H&E was performed using Improvision Openlab™ 4.0.2 software (Improvision). For immunohistochemistry, deparaffinized sections were treated with endogenous peroxidase blocking reagent (Dako Cytomation A/S) and proteinase K (Dako Cytomation A/S) for 20 minutes and 6 minutes at room temperature, respectively. They were then incubated with rabbit antimyeloperoxidase (MPO) polyclonal antibody (NeoMarkers) diluted 1:200, rat anti-mouse F4/80 monoclonal antibody (mAb) (Abcom Limited) diluted 1:400 or rat antimouse CD31 (platelet endothelial cell adhesion molecule 1, PECAM-1) mAb (PharMingen) or rabbit anti-mouse TGF-β1 polyclonal antibody (Santa Cruz Biotechnology, Inc) both diluted 1:200 overnight at 4° C. after blocking with 15% skimmed milk for 1 hour at room temperature. In addition, some sections were reacted with phalloidin-tetramethylrhodamine B isothiocyanate (Sigma-Aldrich) diluted 1:500 for 1 hour at room temperature. The antibodies were appropriately diluted in Antibody Diluent with Background Reducing Components (Dako Cytomation A/S). The sections reacted with anti-MPO antibody and anti TGF-β1 antibody were stained with EnVision+™ (Dako Cytomation A/S) to enhance the signal, according to the manufacturer's instructions. The sections that had been reacted with anti-F4/80 and anti-CD31 antibodies were incubated with biotinylated rabbit anti-rat immunoglobulin (Dako Cytomation A/S) diluted 1:200 for 1 hour at 37° C. The signal was then enhanced using the Catalyzed Signal Amplification System® (Dako Cytomation A/S) according to the manufacturer's instructions. Thereafter, counterstaining was performed with methyl green (Dako Cytomation A/S) followed by MPO, TGF-β31, F4/80, and CD31 staining or 4',6-diamidino-2-phenylindole (DAPI) followed by phalloidin staining.

Immunostaining for connexin 43, blood vessels or α smooth muscle actin was carried out on cryostat sections of wounds. Sections were fixed in acetone at 4° C. for 5 minutes prior to blocking for 45 minutes. Incubation in primary antibody was for one hour at the following dilutions: rabbit anti-Cx43 (Sigma) 1:3,000; isoLectin B_FITC 1:2000; von Willebrand Factor (rabbit Dako) 1:400; anti-α smooth muscle actin (Sigma) 1:400 at room temperature. Sections were washed for 3×5 minutes in PBS before a one hour incubation in anti-rabbit-FITC secondary antibody (Dako) 1:200 at room temperature. Washing 3×5 minutes in PBS, in some cases with 1 μM bis-benzimide (Sigma) in the first wash as a nuclear counter stain, and mounted in Citifluor (Citifluor, London, UK). Sections were imaged by confocal microscopy with all parameters kept constant to allow direct comparison of digital images.

TUNEL Staining

Wound tissues were fixed in 4% formaldehyde buffered with PBS, and embedded in paraffin and sectioned. Deparaffinized sections were treated with proteinase K (Dako Cytomation A/S) for 5 minutes at room temperature. They were then stained using the In Situ Cell Death Detection Kit (Roche) according to the manufacture's instructions. Thereafter, counterstaining was performed with 4', 6-diamidino-2-phenylindole (DAPI). TUNEL stained section were imaged and positive cells were counted in the granulation tissue in three random fields, in the two sides and center of each wound (each field was 0.332 mm2).

Detection of Proliferating Cells by Labeling with 5'-bromo-2'-deoxy-uridine (BrdU)

In another experiment, wounded mice were injected intraperitoneally with 1 ml of BrdU (Sigma) in PBS solution (1 mg/ml) 2 hours before harvesting on days 1, 2, and 7. Wound tissues were fixed in 4% formaldehyde buffered with PBS, and embedded in paraffin. Deparaffinized sections (6 μm thick) were treated with a HistoMouse™-Plus Kit (ZYMED Laboratories, Inc) to reduce background signals according to manufacturer's instructions. Sections were stained with BrdU Detection Kit (BD Bioscience Pharmingen) according to manufacture's instruction. Thereafter, counterstaining was performed with methyl green (Dako Cytomation A/S).

Measurement of Neutrophils, Macrophages, Fibroblasts, BrdU-Positive Cells, and Angiogenesis A treatment-blinded observer counted MPO-positive neutrophils and F4/80-positive macrophages in the wound bed (defined as the area surrounded by unwounded skin, fascia, regenerated epidermis, and eschar) in 3 random high-power fields of 0.332 mm$^2$. BrdU-positive cells in the wound margin and the nascent epidermis regions of each immunohistochemically stained section were counted as described previously and expressed per 100 m of epidermis (Mori, R., Kondo, T., Nishie, T., Ohshima, T. and Asano, M. (2004). Impairment of skin wound healing in beta-1,4-galactosyltransferase-deficient mice with reduced leukocyte recruitment. *Am J Pathol* 164, 1303-14). Number of fibroblast like cells (phalloidin-positive cells with spindle-shape body) at the wound margin were counted in high-power fields also (each field was 0.332 mm$^2$). The neovascularization was followed using von Wildebrand factor fluorescent staining of endothelial cells at days 5, 7, 10 and 14 after wounding. Myofibroblasts were identified by anti-α smooth muscle actin staining. For quantification of both fluorescent stains a confocal microscope was used to take single section images from comparable zones from a minimum six animals per time point. All parameters of image acquisition were kept constant to allow comparison. Images were made binary at a standard threshold and positive pixels were counted using Image J (NIH Image).

Hydroxyproline Analysis

The collagen content of the wound area was assessed by determining the amount of hydroxyproline (HP), a major component of collagen. Samples were homogenized in 1 ml of T-PER® Tissue Protein Extraction Reagent (PIERCE Biotechnology Inc.) including Halt™ Protease Inhibitor Cocktail, EDTA-Free (PIERCE Biotechnology Inc.), and were centrifuged at 15,000 rpm for 20 minutes at 4° C. to remove the debris. Concentrations of protein were measured using a BCA™ Protein Assay Kit (PIERCE Biotechnology Inc.), and the amounts of HP were determined with Sircol™ Soluble Collagen Assay Kit (Biocolor Ltd.). The data were expressed as amounts of HP/total protein (ng/g) for each sample.

Cell Culture

Swiss 3T3 fibroblasts were grown in Dulbecco's modified Eagle's medium (DMEM; Gibco) supplemented with 10% fetal calf serum (Labtech) and 1% penicillinstreptomycin solution (Sigma, Poole) in a 5% CO2 incubator at 37° C. Unless otherwise stated, the cells were maintained in this medium for most experiments. The cells were passaged by trypsinization and used at passages 6-10 at a confluency of ≈90%. Cells were plated on 13 mm glass coverslips in 24-well dishes (Nunc) with 4-5×10$^5$ cells per well containing 1 ml of medium. Cells reached confluency after 72 hours and were then used for experimentation.

Cell Migration Assay by Wounding

The fibroblast cell assay involved creating a "wound" in a confluent monolayer of fibroblast cells. This widely used in vitro technique mimics the behaviour of migrating cells in vivo (Lampugnani, M. G. (1999) Cell Migration into a wounded area in vitro. *Methods Mol Biol* 96: 177-182). Wounding was performed by drawing a microelectrode across the coverslip, producing a lesion of standard width. Phase contrast images were acquired using a ×5 objective on a Zeiss inverted microscope with an incubation chamber at 370 and 5% CO2. An image of a defined area at the edge of a cover slip was taken immediately after wounding and a further image was taken of the same area 4 hours later, a time at which migration could be clearly seen to have taken place (FIG. 7E, 7F). A minimum of eight coverslips, were imaged in each of the control and treated groups. Migration was quantified by image analysis, measuring the change in wound area (pixels) using Image J software (NIH).

In order to knock down Cx43 expression in the fibroblasts the media was replaced with serum-free DMEM containing either 20 μM asODNs or 20 μM control sODNs. This was incubated for two hours before being replaced with serum containing DMEM. The wounding assay was then carried out as above. Previous experience has shown that two hours is sufficient to achieve significant knockdown of Cx43 protein (Qiu, C., Coutinho, P., Frank, S., Franke, S., Law, L. Y., Martin, P., Green, C. R. and Becker, D. L. (2003). Targeting connexin 43 expression accelerates the rate of wound repair. *Curr Biol* 13, 1697-703) and the knockdown process continues during the wound migration assay.

Isolation of RNA and Quantitative Gene Expression Level with Real-Time PCR

Total RNA was extracted from skin wound samples using TRIzol Reagent (Invitrogen), according to the manufacturer's instructions. Ten micrograms of total RNA was reverse-transcribed into cDNA using the SuperScript First-Strand Synthesis System for RT-PCR (Invitrogen).

Gene specific primers and probe were obtained as Taq-Man® Gene Expression Assays (Applied Biosystems) for Cx43, Ccl2, Colα1, TNFα and TGFβ1. The enzyme and buffer system was purchased as TaqMan® Universal PCR Master Mix (Applied Biosystems). Each sample was analyzed in duplicate. Amplification and real-time detection was performed in the DNA Engine Opticon®2 (MJ Research Inc.). Expression of target genes was compared with GAPDH expression.

Statistical Analysis

Statistical differences were determined using the unpaired Student's t test or the Mann Whitney U test as appropriate. All data are presented as the mean±s.e.m. Criterion levels for the individual tests are given in Results.

Downregulation of Cx43 at Wound Sites with Cx43 asODN

Cx43 was found to be predominantly expressed in the lower and middle spinous cell layers of the epidermis and in fibroblasts, blood vessels and dermal appendages of intact skin. Six hours after the injury Cx43 was expressed in hyperproliferative epidermis but began to be downregulated in the leading edge keratinocytes. Delivery of Cx43 asODN from the time of injury markedly reduced protein levels of Cx43 in the epidermis and dermis within two hours of treatment. Such a rapid knockdown is possible because Cx43 protein is turned over rapidly, sometimes within 1.5-2 hours. In order to quantify the extent of Cx43 protein and mRNA knockdown and recovery after asODN treatment more precisely, we compared expression levels of Cx43 mRNA at treated versus untreated wound sites with real-time PCR (RT-PCR; FIG. 1). One day after injury, expression of Cx43 mRNA at Cx43 asODN treated wounds was significantly reduced by comparison with control sODN-treated wounds (2.95 versus 4.7 units, respectively, a 37% reduction; P<0.05). By 7 days after the injury, however, expression levels were similar in the two wound regimes (4.6 versus 5.2 units for asODN and control sODN-treated, respectively). Immunostaining of wounds for Cx43 at 1 day, 2 days and 7 days after wounding revealed very low levels of Cx43 protein in the epidermis and dermis of the Cx43 asODN-treated wound edge at day 1 compared to controls (FIG. 1). By day 2, some Cx43 staining had returned to the dermis of the Cx43 asODN-treated wound but the level was still very low in the epidermis. By day 7, in agreement with the RT-PCR findings, there was no obvious difference in Cx43 staining between treated and untreated. These results confirm that this Cx43 asODN, when delivered by Pluronic gel, does indeed inhibit expression of Cx43 mRNA at early time points after wounding.

Accelerated Closure and Increased Proliferation in Cx43 asODN Treated Wounds

Figure 2F:
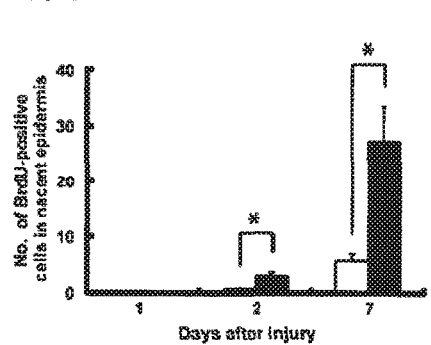
Figure 2G:
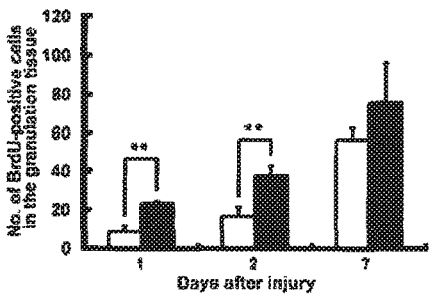
Figure 2H:
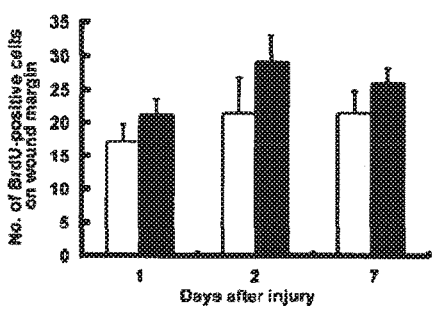

Wounds were identically photographed macroscopically and their areas measured digitally. As we have reported previously (Qiu, C., Coutinho, P., Frank, S., Franke, S., Law, L. Y., Martin, P., Green, C. R. and Becker, D. L. (2003). Targeting connexin 43 expression accelerates the rate of wound repair. Curr Biol 13, 1697-703), Cx43 asODN-treated wounds were significantly smaller, drier, less inflamed and closed faster than control wounds at days 1 and 2. By day 7, scabs covered the wounds and made it impossible to give accurate measurements of wound closure. Reepithelialization from the wound edge commenced soon after injury in order to cover the denuded site. Cx43 asODN treatment of both excisional and incisional wounds results in wounds that re-epithelialise more rapidly than control ODN treated wounds. We therefore examined whether this might be partially due to enhanced proliferation of keratinocytes and fibroblasts in the healing skin of Cx43 asODN treated wounds (FIGS. 2A to 2H). Whilst there was little difference in keratinocyte proliferation between control and treated groups in the epidermal wound margin (FIG. 2E), we showed that, indeed, there are significantly increased numbers of BrdU-positive cells in the nascent epidermis of Cx43 asODN-treated wounds after both 2 days and 7 days (FIG. 2F). Similarly, counts of BrdU-positive cells in the dermal wound margin revealed slightly more cells following asODN-treatment and significantly more in the granulation tissue at days 1 and 2 (FIGS. 2G and 2H). These results are consistent with our gross microscopic observations, and suggest that acute downregulation of Cx43 at wound sites leads to a surge of proliferation of wound-edge keratinocytes that continues as they re-epithelialize the wound. This enhanced proliferation may contribute to the accelerated re-epithelialization and enhanced granulation tissue maturation in asODN treated wounds.

Figure 3A:
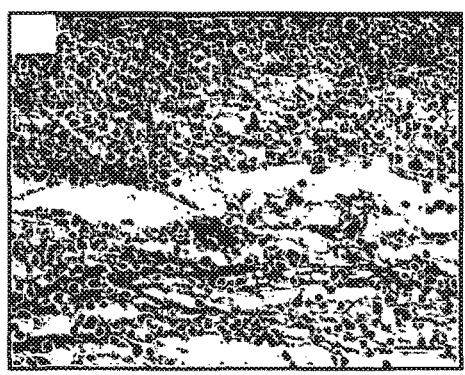
FIG. 3A to FIG. 3C depict neutrophil recruitment into a wound site.
Figure 3B:
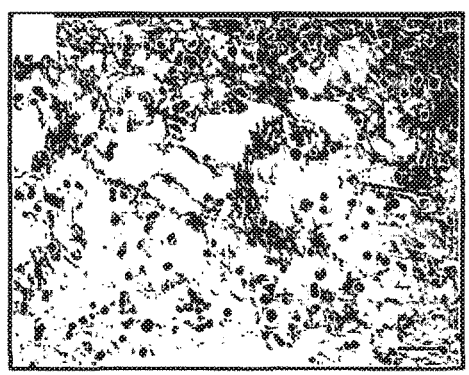
Figure 3C:
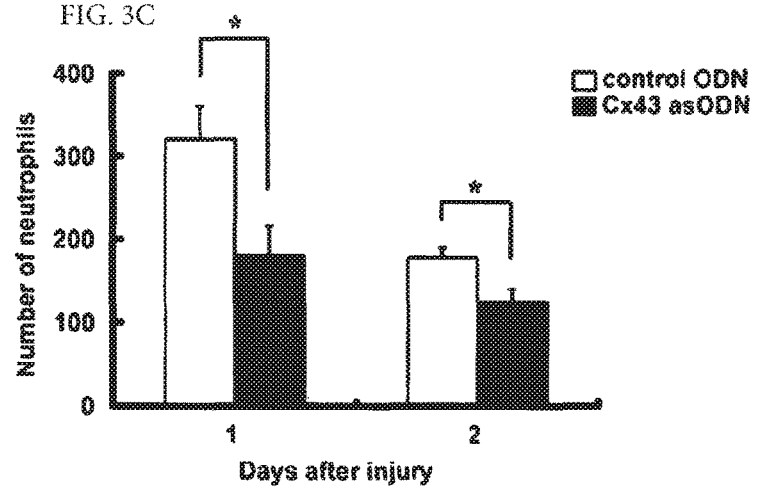
Figure 4A:
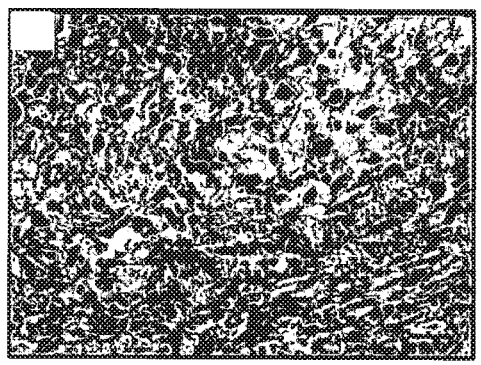
FIG. 4A to FIG. 4C depict macrophage recruitment into a wound site.
Figure 4B:
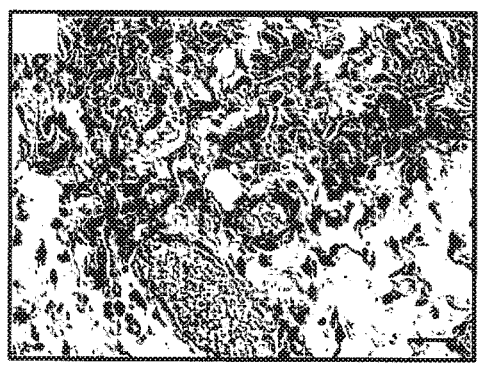
Figure 4C:
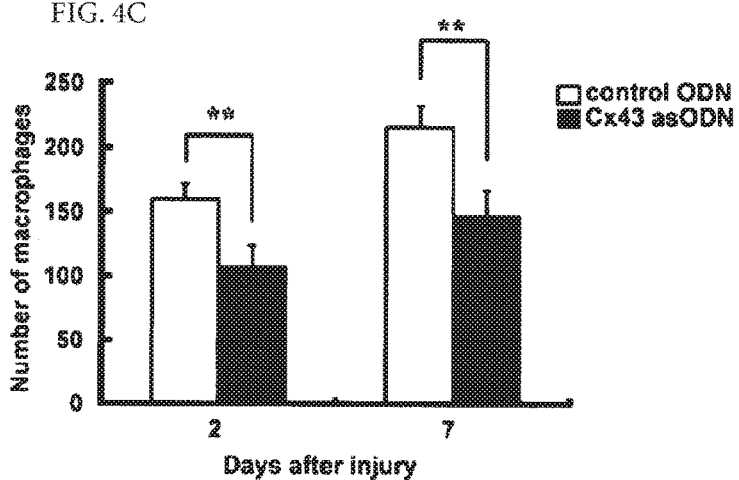

Reduced Influx of Inflammatory Cells in Cx43 asODN-Treated Wounds—Neutrophils and Macrophages Several leukocyte lineages infiltrate the wound site with varying time courses during the inflammatory response to tissue damage. The two primary cell lineages are neutrophils and macrophages both of these can exert profound effects on various aspects of the repair process. We have previously evaluated neutrophil influx in Cx43 asODN-treated wounds and here we confirm with an anti-MPO antibody that their numbers are significantly reduced on day 1 and 2, at a stage when neutrophil numbers are peaking in control treated wounds (FIG. 3). There is now clear evidence that the macrophage influx at a wound site may be linked to the rate of re-epithelialization and to the eventual extent of scarring at the wound site, so we have investigated macrophage numbers using F4/80 immunohistochemistry (FIGS. 4A to 4C). We found that the number of macrophages at Cx43 asODN treated wound sites was significantly reduced at 2 and 7 days after the injury compared with control sODN-treated wounds, this being a reduction of 33% on day 2 and 32% on day 7 (FIG. 4C). These data clearly indicate that acute knockdown of Cx43 at the time of wounding leads to a dramatic subsequent reduction in both the early neutrophil and later, macrophage, and inflammatory phases.

Reduced Expression of Ccl2 and TNF-α in Cx43 asODN-Treated Wounds

Figure 5A:
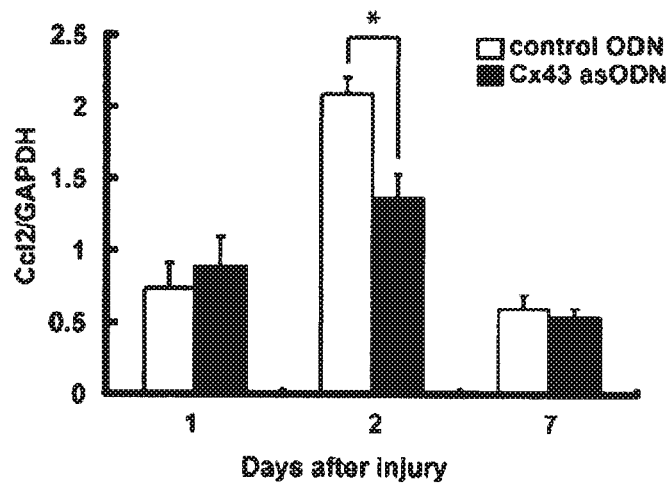
FIG. 5A to FIG. 5B depict expression of Ccl2 and TNF-α at wound sites.
Figure 5B:
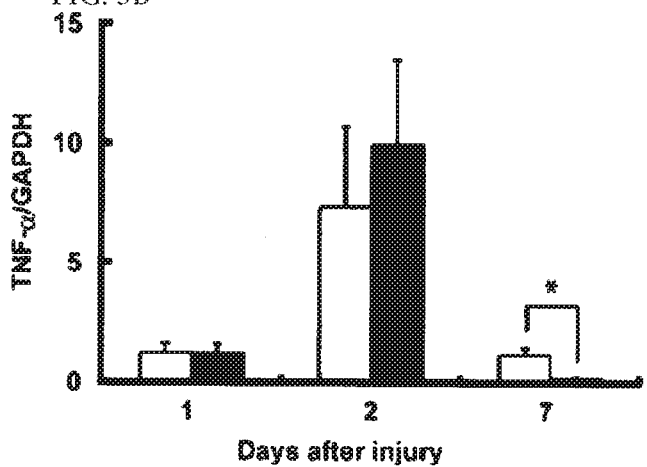
Figure 8A:
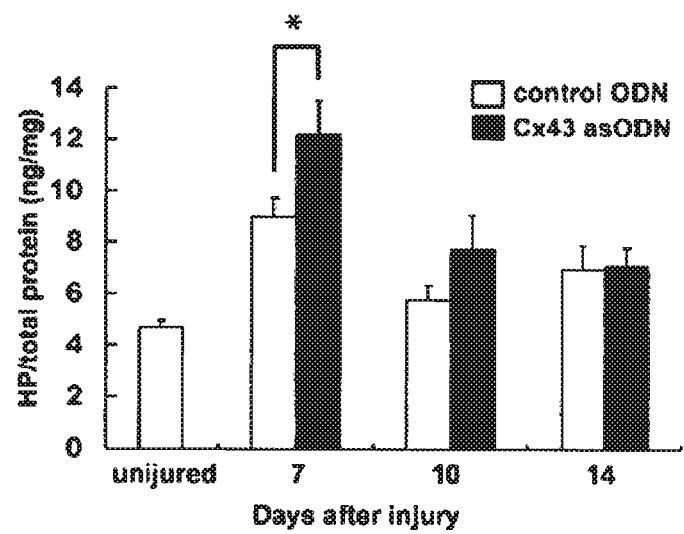
FIG. 8A to FIG. 8B depict collagen expression in a wound site.
Figure 8B:
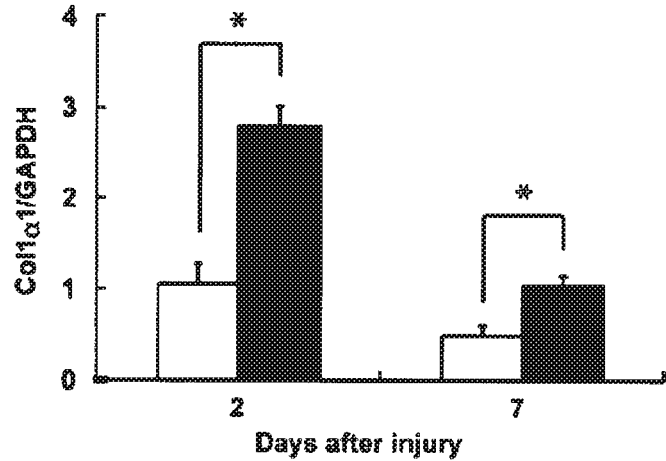

Neutrophils and macrophages at the wound site release a large variety of proinflammatory cytokines and chemokines that act directly on cells in that site (keratinocytes, fibroblasts and endothelial cells) and amplify the wound inflammatory response. To examine how the reduced influx of inflammatory cells, after Cx43 knockdown, influences the level of these signals, we analysed Ccl2 and TNF-α as a representative chemokine and cytokine, respectively. To quantify expression levels of Ccl2 and TNF-α we performed RT-PCR analysis on wound tissue on days 1, 2, and 7 (FIGS. 5A and 5B). Both mRNAs were robustly upregulated in control sODN-treated wound sites on day 1, and both peaked in expression levels at day 2, after which their levels decreased. By comparison, expression levels of Ccl2 and TNF-α in Cx43 asODN treated wounds were significantly reduced ($P<0.05$) on day 2 (Ccl2) and 7 (TNF-α). These results indicate that reduced recruitment of neutrophils and macrophages in Cx43 asODN treated wounds was indeed accompanied by diminished expression of these signaling molecules without compensation by other cell types.

To quantify expression levels of Ccl2 and TNF-α RT-PCR analysis was performed on wound tissue on days 1, 2, and 7. Both mRNAs were robustly upregulated in control sODN-treated wound sites on day 1, and both peaked in expression levels at day 2, after which their levels decreased. By comparison, expression levels of Ccl2 and TNF-α in Cx43 asODN treated wounds were significantly reduced ($P<0.05$) on day 2 (Ccl2) and 7 (TNF-α). These results indicate that reduced recruitment of neutrophils and macrophages in Cx43 asODN treated wounds was indeed accompanied by diminished expression of these signalling molecules without compensation by other cell types.

Increased TGF-β1 Expression at Cx43 asODN-Treated Wound Sites

The wound-associated growth factor, TGF-β1 has been reported to play a wide variety of roles at many stages of the wound-healing process. Therefore, we analyzed the expression levels of TGF-β1 at control sODN and Cx43 asODN treated wound sites with RT-PCR at 1 day, 2 days and 7 days after wounding (FIG. 6). TGF-β1 was at low levels on days 1 and 7 with no difference between control and treated wounds. However, on day 2 after the injury, the expression of TGF-β1 in asODN-treated wounds was significantly increased ($P<0.05$) compared with control sODN-treated wounds. Immunostaining for TGF-β1 at 2 days revealed TGF-β1 positive cells in the dermis both at the wound site and in the adjacent tissues. Most of the cells were round and had the appearance of leucocytes. However, in the Cx43 asODN-treated tissue an additional TGF-β1 positive cell type could be seen in large numbers at the dermal margins of the wound. These cells appeared to be elongated and more fibroblast like in their morphology. Interestingly, in the epidermis of Cx43 asODN treated wounds TGF-β1 appeared to stain much more strongly than in control wound epidermis (FIG. 6.) These results raise the possibility that increased expression of TGF-β1 might contribute to some of the changes we see in wound healing following Cx43 asODN treatment.

Granulation Tissue Formation and Maturation

Connective-tissue wound contraction has been said to be a key component of the skin repair process. This step is closely associated with migration of fibroblasts into the wound bed and their differentiation into contractile myofibroblasts followed by their loss (Martin, P. (1997). *Science* 276, 75-81). Using rhodamine phalloidin combined with DAPI nuclear counter stain we found a significant increase (means of 39.4 in control and 99.2 in asODN; P<0.01) in the number of elongated fibroblast like cells at the margin of 2 day Cx43 asODN-treated, by comparison to control wounds (FIGS. 7A and B). These data suggest that the influx of fibroblasts to form wound granulation tissue is enhanced in wounds when Cx43 protein has been reduced. This may be due to both enhanced migration and the significantly greater cell proliferation that we see in the granulation tissue of asODN-treated wounds.

To investigate whether the enhanced rate of fibroblast migration was due to a reduction in Cx43 protein expression we used a fibroblast wound-healing assay. Here we knocked down Cx43 protein by applying Cx43 asODNs to confluent cultures of fibroblasts two hours prior to a scrape wound assay. Because Cx43 protein is rapidly turned over (with a half life as short as 1.5-2 hours) this is sufficient to produce a 95% knockdown of the protein within two hours, which can last between eight and 48 hours depending on the cell type. Fibroblast cultures that were treated with the Cx43 asODNs exhibited a significantly (P=0.02) enhanced rate of wound closure, compared to controls (FIG. 7D) which is entirely consistent with our in vivo findings. This strongly suggests that knockdown of Cx43 protein enhances the rate of migration of fibroblasts both in vitro and in vivo, and thereby promotes the rate of granulation tissue formation.

When measuring granulation tissue areas, we found that treated tissue was slightly smaller than untreated tissue at day 5, but this difference was not significant. However, we found that on days 7, 10 and 14 after wounding Cx43 asODN treated wounds exhibit significantly (*P<0.05; **P<0.01) smaller areas of granulation tissue than control sODN treated wounds.

Figure 9A:
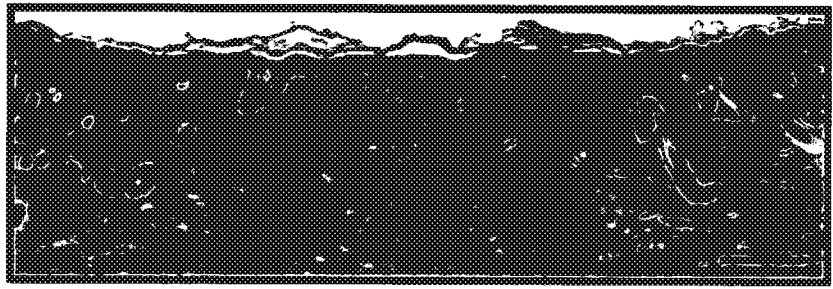
FIG. 9A to FIG. 9C depict granulation tissue contraction.
Figure 9B:
Figure 9C:
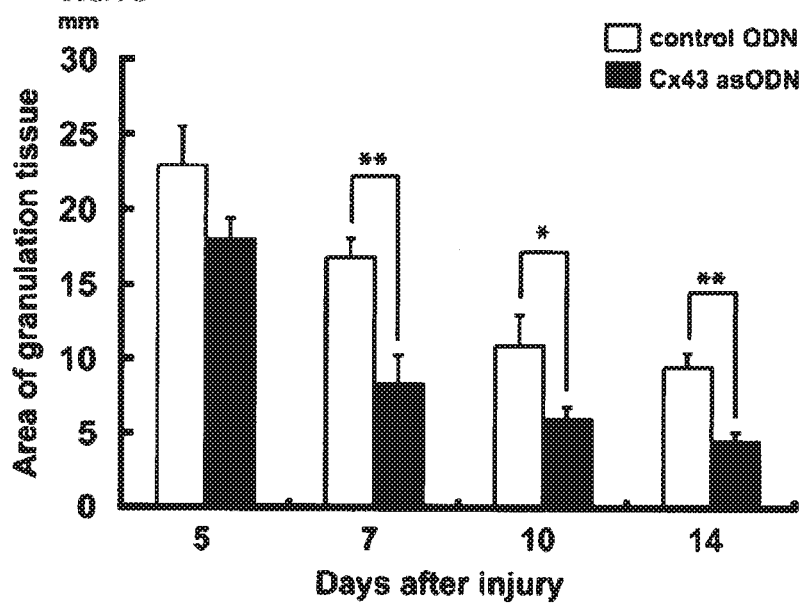
Figure 10A:
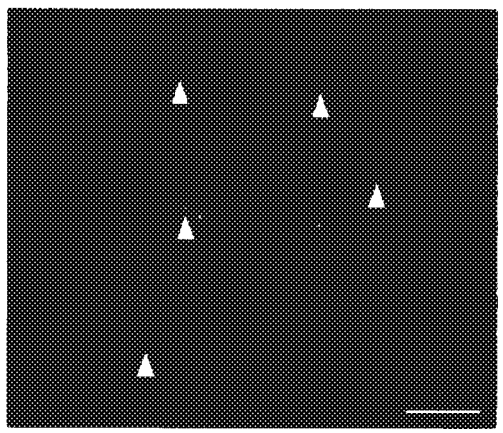
FIG. 10A to FIG. 10C depict apoptosis at wound sites.
Figure 10B:
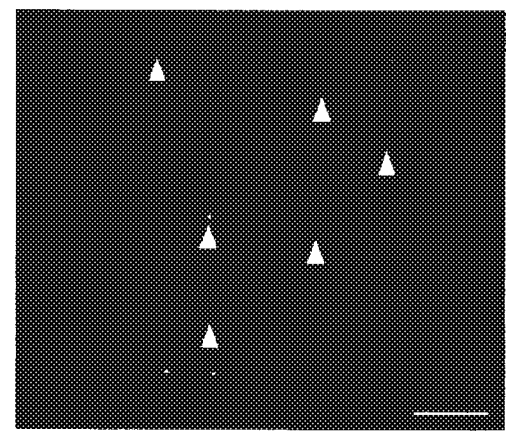
Figure 10C:
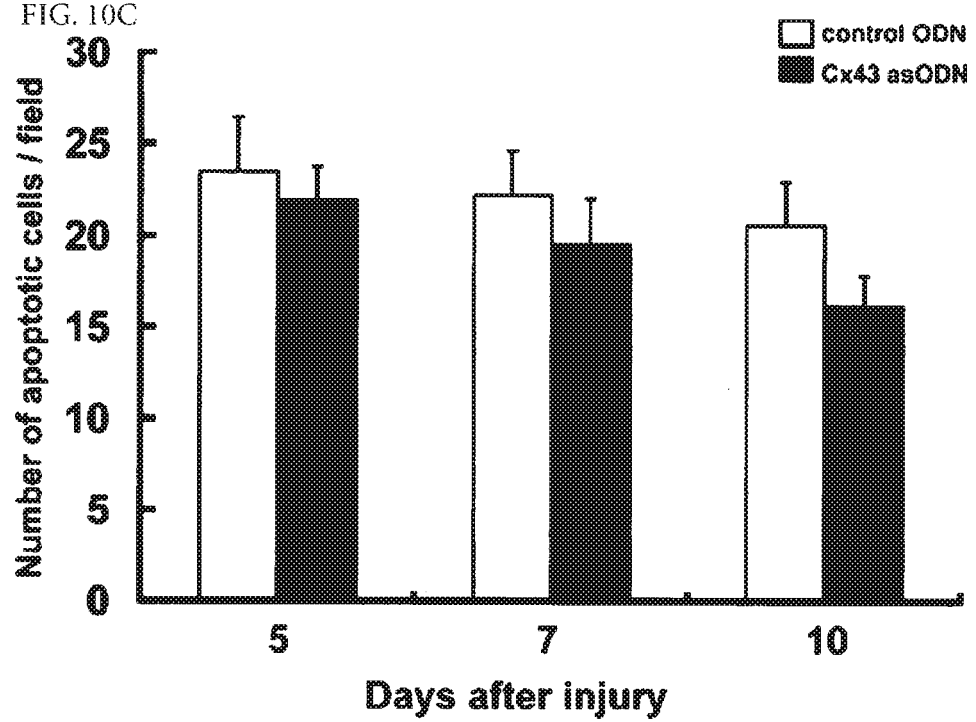

When measuring granulation tissue areas, we found that treated tissue was slightly smaller than untreated tissue at day 5, but this difference was not significant. However, we found that on days 7, 10 and 14 after wounding Cx43 asODN treated wounds exhibit significantly (*P<0.05; **P<0.01) smaller areas of granulation tissue than control sODN treated wounds (FIG. 9). To investigate how the more rapid contraction of the granulation tissue was brought about we stained sections with a TUNEL labeling kit, to look for apoptotic cell death, or with anti-smooth muscle actin (SMA) as a marker of myofibroblasts. Although there were always slightly fewer apoptotic cells in treated granulation tissue, we found no significant differences in the numbers of TUNEL positive cells between control and treated animals at 5, 7 and 10 days after wounding (FIG. 10). However, we observed a highly significant difference in the expression of SMA staining between the two groups at all of these time points (FIG. 11). At day 5, staining for SMA could be detected at the edges of the granulation tissue of Cx43 asODN-treated wounds but no staining could be seen as yet in control wounds. By day 7 staining for SMA could be detected at the edges of the granulation tissue of control wounds and throughout the granulation tissue of Cx43 asODN-treated wounds (FIGS. 11 A and 11B). Quantification of the staining at the edges of the granulation tissue revealed that it was significantly higher (P=0.004) in Cx43 asODN-treated wounds (FIG. 11 E). At 10 days after wounding most of the staining for SMA had gone from the edges of the granulation tissue of Cx43 asODN treated wounds, just a little remained in the center of the wound. This was significantly different (P=0.000002) from control wounds, which showed strong SMA expression throughout the granulation tissue (FIGS. 11 C and 11D). These findings imply that differentiation of fibroblasts into myofibroblasts occurs earlier in Cx43 asODN treated wounds and that these cells go on to contract the wound and are lost much faster than in control wounds. It would appear that Cx43 asODN-treated wounds are 2-3 days more advanced than controls in the maturation of their granulation tissue.

Angiogenesis

Figure 12A:
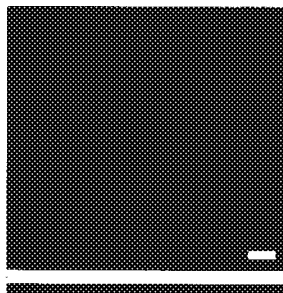
FIG. 12A to FIG. 12H depict angiogenesis at wound sites.
Figure 12B:
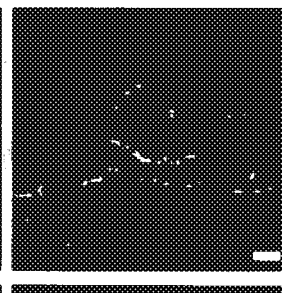
Figure 12C:
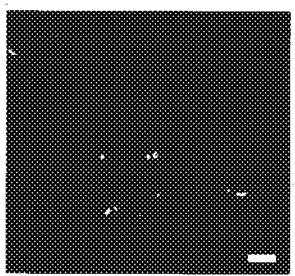
Figure 12D:
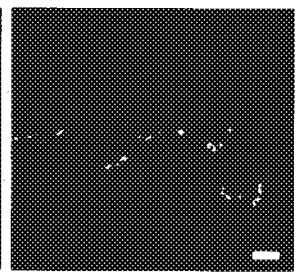
Figure 12E:
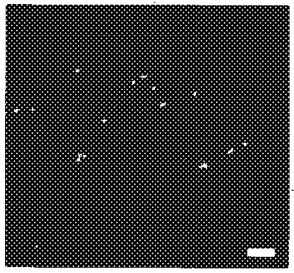
Figure 12F:
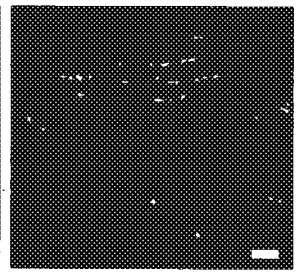
Figure 12G:
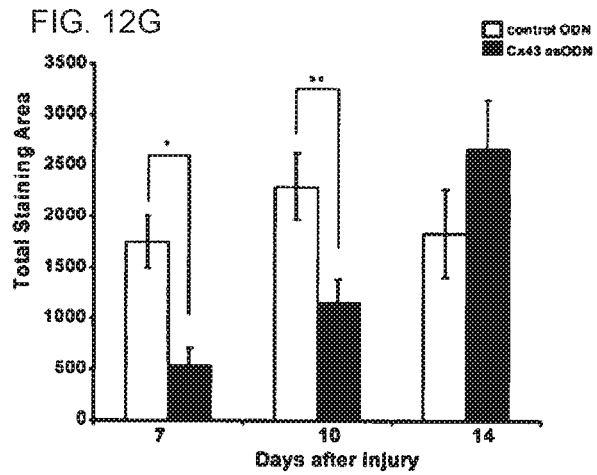
Figure 12H:
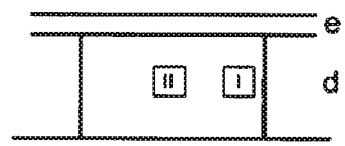

Besides the influx of fibroblasts, the other major cellular components of wound granulation tissue are the endothelial cells of new blood vessels. We therefore performed immunohistochemical staining using anti-CD31 and von Willebrand factor antibodies or isolectinB-FITC in order to evaluate angiogenesis at treated wound sites at 5, 7, 10 and 14 days after wounding (FIGS. 12A to 12H). At 5 days, no blood vessel staining could be seen in the granulation tissue of control wounds whereas staining was seen in the edges of the granulation tissue of all Cx43 asODN treated wounds. At day 7, fine blood vessels were found throughout the entire granulation tissue in five out of six Cx43 asODN-treated wounds but they had only just started to enter the edges of the granulation tissue of controls. However, whilst the blood vessels of asODN-treated wounds were more pervasive they appeared to be significantly smaller or thinner than those of controls at this time point (FIG. 12A). This meant that, when blood vessel staining was quantified at 7 and 10 days there was significantly more staining in controls (7 days P=0.0019; 10 days P=0.015) where the vessels were bigger. At 14 days, the size of blood vessels and extent of staining were very similar in both treated and control groups (FIG. 12E, 12F). These findings suggest that angiogenesis takes place much earlier after Cx43 asODN treatment. Taken with our other findings relating to granulation tissue maturation it would seem that the treatment enhances the rate of wound maturation by 2-3 days.

As shown in the results, exemplary pathological and biological consequences of acute downregulation of Cx43 at sites of skin wound healing using Cx43 asODN delivered from a Pluronic F-127 slow-release gel are presented herein. The treatment rapidly down-regulates Cx43 protein in the woundsite epidermis and dermis for at least 24 hours with some return of dermal expression by 48 hours and no obvious differences between groups after 7 days. We show that Cx43 asODN treatment leads to markedly accelerated skin wound healing, coincident with reduced leukocyte infiltration, reduced cytokines, increased re-epithelialization and enhanced wound contraction.

Inflammation

The initial response to wounding is typically the formation of a blood clot, which, together with local damaged tissue, releases proinflammatory signals, which trigger inflammatory cell infiltration in the form of neutrophils and then macrophages into the wound site. These signals and those from the invading inflammatory cells influence both re-epithelialisation and connective tissue contraction of the wound (Martin, P. (1997). *Science* 276, 75-81). The migration and infiltration of inflammatory cells into the wound is associated with cell-cell and cell-matrix interactions and with vasodilation of blood vessels in the proximity of the wound. It has recently been reported that Cx43 is expressed in activated leukocytes, and at leukocyte-leukocyte and leukocyte-endothelial cell contact sites during their extravasation under inflammatory conditions, and that functional Cx43 channels are involved in release of cytokines and immunoglobulins (reviewed by: Oviedo-Orta, E. and Evans, W. H. (2004). *Biochim Biophys Acta* 1662, 102-12). The results reported here show that numbers of both neutrophils and macrophages were significantly reduced in Cx43 asODN-treated wounds which is in keeping with the requirement for Cx43 expression for neutrophil extravasation and release of proinflammatory cytokines. In addition, the results show that the chemokine Ccl2 and cytokine TNF-α, which are reported to be chemoattractants for neutrophils and monocytes/macrophages (Rossi, D. and Zlotnik, A. (2000). *Annu Rev Immunol* 18, 217-42), are also both reduced after Cx43 asODN treatment on day 2 and 7, respectively. Clearly, the reduced levels of these and other growth factors, chemokines, and cytokines at the wound site are indicative of that these agents useful for wound healing are important mediators (both upstream and downstream) of the reduced influx of neutrophils and other inflammatory cells.

Several recent reports have postulated that a normal inflammatory response is not essential for skin wound healing (Martin, P. and Leibovich, S. J. (2005). *Trends Cell Biol.*). PU.1 null mice, which are genetically missing neutrophils and macrophages, have been said to repair skin lesions without scarring and at a similar rate to, or faster than, their wild type siblings (Martin, P., D'Souza, D., Martin, J., Grose, R., Cooper, L., Maki, R. and McKercher, S. R. (2003). *Curr Biol* 13, 1122-8). Similarly, decreasing the numbers of neutrophils at wound sites by applying antineutrophil sera has been reported to lead to faster re-epithelialization (Dovi, J. V., He, L. K. and DiPietro, L. A. (2003). *J Leukoc Biol* 73, 448-55). Correlation between the increase in the epidermal migration and proliferative capacity and the reduced inflammatory response and the possible role of Cx43 knockdown in the leading-edge keratinocytes and fibroblasts. Furthermore, Cx43 knockdown may lead to reduced leukocyte influx. The target tissue for Cx43 asODN action may include endothelial cells or leukocytes, both of which have been reported to require Cx43 expression for effective extravasation and a robust inflammatory response (Oviedo-Orta, E., Hoy, T. and Evans, W. H. (2000). *Immunology* 99, 578-90; Oviedo-Orta, E., Gasque, P. and Evans, W. H. (2001). *FASEB J* 15, 768-74). Based on these results, alteration of Cx43 protein expression in endothelial cells or leukocytes may also regulate the inflammatory response.

TGF-β1

In Cx43 asODN treated wounds we found that mRNA for TGF-β1 is significantly increased on day 2 compared with controls but is found at relatively low levels in both treated and control wounds on day 1 and day 7. Expression of TGF-11 has been reported as being associated with many key events in the wound healing process. Its reported activities include being an immunosuppressive, promoting fibroblast migration and proliferation, enhancing wound contraction, enhancing granulation tissue formation, enhancing collagen synthesis and deposition, stimulating angiogenesis and promoting re-epithelialization. The effect of TGF-β1 on the wound has been reported to be somewhat dependent on dosage and wounding model. Various results have also been reported based on perturbation of different parts of the TGF-β1 signaling pathway and experiments using genetically modified. For example, in TGF-β1 knockout mice that are deficient in T cells and B cells (Scid$^{-/-}$ mice) wound healing is delayed (Crowe, M. J., Doetschman, T. and Greenhalgh, D. G. (2000) *J. Invest. Dermatol* 115: 3-11). However, when the TGF-β1 signaling pathway is disrupted, as it is in Smad3 knockout mice, wound healing is accelerated (Ashcroft, G. S., Yang, X, Glick, A. B., Weinstein, M., Letterio, J. L., Mizel, D. E., Anzano, M., Greenwell-Wild, T., Wahl, S. M., Deng, C. and Roberts, A. B. (1999) *Nat Cell Biol.* 1:260-6). Similarly, the expression of a dominant-negative type II TGF-β receptor in keratinocytes leads to re-epithelialization being again accelerated. Transgenic mice with over expression of TGF-β1 show a better quality of wound healing with reduced scar formation (Shah, M., Revis, D., Herrick, S., Baillie, R., Thorgeirson, S., Ferguson, M. and Roberts, A. (1999) *Am. J. Pathol.* 154:1115-24). Similarly, transgenic mice lacking beta 3-integrin show elevated levels of TGF-β1 that are associated with enhanced healing and faster fibroblast migration into the wounds (Reynolds, L. E., Conti, F. J., Lucas, M., Grose, R., Robinson, S., Stone, M., Saunders, G., Dickson, C., Hynes, R. O., Lacy-Hulbert, A. and Hodivala-Dilke, K. (2005) *Nat. Med.* 11:167-74). CD18 knockout mice exhibit reduced TGF-131 expression and have delayed wound healing which can be rescued by injecting TGF-β1 into the wound margins (Peters, T., Sindrilaru, A., Hinz, B., Hinrichs, R., Menke, A., Al-Azzeh, E. A., Holzwarth, K., Oreshkova, T., Wang, H., Kess, D., Walzog, B., Sulyok, S., Sunderkotter, C., Friedrich, W., Wlaschek, M., Krieg, T. and Scharffetter-Kochanek, K. (2005) *EMBO J.* 24:3400-10).

The elevated levels of TGF-β1 staining that we see on day 2 appear to be largely in elongated fibroblast-like cells at the edge of the wound and in the keratinocytes at the edge of the wound. This is consistent with previously-described effects of TGF-β1 on enhanced proliferation and migration (Postlethwaite, A. E., Keski-Oja, J., Moses, H. L. and Kang, A. H. (1987) *J Exp Med* 165:251-6), both of which we see in the early stages of tissue repair. Indeed, the TGF-β1 elevation may be one of the factors that in these conditions contribute to the promotion of healing, in terms of the increased rate of proliferation and migration of fibroblasts and the enhanced rate of collagen synthesis that we see at these early time points.

Both the active downregulation of Cx43 protein and the action of the wound-associated growth factor TGF-β1 have been reported to activate Col1a1 expression (Cutroneo, K. R. (2003). How is Type I procollagen synthesis regulated at the gene level during tissue fibrosis. *J Cell Biochem* 90, 1-5; Waggett, A. D., Benjamin, M. and Ralphs, J. R. (2006) *Eur J Cell Biol.* 2006 Jul. 19; [Epub ahead of print]). The enhanced Col1α1 expression and collagen deposition that we see following treatment may be related to the increased expression of TGF-β1 at 2 days, or to the Cx43 protein downregulation or both.

The wound-associated growth factor, TGF-31, plays a wide variety of roles at many stages of the wound-healing process. TGF-β1 was at low levels on days 1 and 7 with no difference between control and treated wounds. However, on day 2 after the injury, the expression of TGF-β1 in asODN-treated wounds was significantly increased ($P<0.05$) compared with control sODN-treated wounds. Immunostaining for TGF-β1 at 2 days revealed TGF-β1 positive cells in the dermis both at the wound site and in the adjacent tissues. Most of the cells were round and had the appearance of leucocytes. However, in the Cx43 asODN-treated tissue an additional TGF-β1 positive cell type could be seen in large numbers at the dermal margins of the wound. These cells appeared to be elongated and more fibroblast like in their morphology. Interestingly, in the epidermis of Cx43 asODN treated wounds TGF-β1 appeared to stain much more strongly than in control wound epidermis (FIG. 6.) These results raise the possibility that increased expression of TGF-β1 might contribute to some of the changes we see in wound healing following Cx43 asODN treatment.

Whilst TGF-β1 has been suggested to suppress inflammation, it is unlikely to be the main factor leading to the reduced inflammation that we observe, as that is already evident on day 1 before the TGF-β1 becomes elevated. Similarly, whilst TGF-β1 has been shown to promote angiogenesis and granulation-tissue maturation at later stages of the wound-healing process we see no elevation of TGF-β1 at these later time points; rather it is then at a similar low level to controls. So other factors must promote the enhanced maturation of granulation tissue that we see following treatment.

These experiments support the implication of TGF-β1 has been implicated in the in the suppression of inflammation, promotion of angiogenesis and granulation-tissue maturation of the wound-healing process and indicates that modulation of TGF-β1 in combination with other wound treatment modalities may be useful in promoting the wound healing process.

Migration and Proliferation

Migration and proliferation of fibroblasts and keratinocytes are indispensable for skin wound healing contributing to both wound contraction and wound closure. In this study we show enhanced migration of fibroblasts into the wound site and faster reepithelialisation following Cx43 asODN treatment. These results indicate that Cx43 may play an important role in modulating cell movement. Contradictory results have been reported on the role of Cx43 in cell movement by others who reported that in embryonic development, Cx43-deficient proepicardial cells migrated faster than those expressing Cx43 (Li, W. E., Waldo, K., Linask, K. L., Chen, T., Wessels, A., Parmacek, M. S., Kirby, M. L. and Lo, C. W. (2002). *Development* 129, 2031-42). However, the same group also previously reported that Cx43 deficient neural crest cells showed decreased rates of migration (Huang, G. Y., Cooper, E. S., Waldo, K., Kirby, M. L., Gilula, N. B. and Lo, C. W. (1998). *J Cell Biol* 143, 1725-34). This latter finding is consistent with slowed rates of migration of retinal neuroepithelial cells that have had communication perturbed or Cx43 expression diminished (Pearson R., Luneborg, N., Becker, D. L. and Mobbs P. (2005) *J. Neurosci* 25 (46), 10803-10814). These differences in the effects of communication on migration may perhaps reflect the different cell types involved and whether the cells migrate independently or in a communicating group.

Faster re-epithelialization and an enhanced rate of granulation tissue formation could also be attributed to the enhanced proliferation in the asODN-treated group, which we find in nascent epidermis and granulation tissue at both 2 days and 7 days after wounding. As with migration rates there are mixed reports relating Cx43 expression and proliferation. Cx43-deficient proepicardial cell proliferation is increased, but this is not seen Cx43-deficient cardiac neural crest cells or in the developing neural retina treated with Cx43 asODNs where proliferation is reduced (Huang, G. Y., Cooper, E. S., Waldo, K., Kirby, M. L., Gilula, N. B. and Lo, C. W. (1998). *J Cell Biol* 143, 1725-34; Becker, D. L. and Mobbs, P. (1999) *Exp. Neurology*, 156, 326-332; Li, W. E., Waldo, K., Linask, K. L., Chen, T., Wessels, A., Parmacek, M. S., Kirby, M. L. and Lo, C. W. (2002). *Development* 129, 2031-42). It is interesting that the effects of Cx43 reduction on proepicardial cells promotes both proliferation and migration, whereas the effect on neural crest and retinal neuroepithelial cells is to perturb proliferation and migration. Our experiment here show that reducing Cx43 expression with asODNs in a fibroblast wound healing assay significantly accelerates their rate of migration. The Cx43 protein down regulation may therefore aid the faster re-epithelialization and fibroblast migration into granulation tissue that we see here. Alternatively the influence may come from the elevated levels of TGF-β1, that we see on day 2 in Cx43 asODN-treated wounds, which has been suggested to enhance cell proliferation and increase rates of fibroblast migration (Mustoe, T. A., Pierce, G. F., Thomason, A., Gramates, P., Sporn, M. B. and Deuel, T. F. (1987). *Science* 237, 1333-6: Postlethwaite, A. E., Keski-Oja, J., Moses, H. L. and Kang, A. H. (1987) *J Exp Med* 165:251-6) or perhaps a combination of both.

Angiogenesis

Angiogenesis is another central feature of granulation tissue formation and maturation, involving invasion, expansion and then remodeling. In this study, blood vessels growing into Cx43 asODN-treated wound granulation tissue were much more advanced than the controls. On day 5 fine blood vessels could be seen entering the granulation tissue of all treated wounds but no vessels were seen in any control granulation tissue. By day 7 fine blood vessels could be seen throughout the granulation tissue in the majority of treated wounds but were only seen at the edges of control wounds. Interestingly, the blood vessels in control wounds appeared to be thicker at these early stages and so gave a significantly greater area of staining at both 7 and 10 days. By 14 days the blood vessels in treated wounds had developed to a greater size and appeared to be very similar to controls. Cx43 is known to be involved in coronary vasculogenesis and angiogenesis (Walker, D. L., Vacha, S. J., Kirby, M. L. and Lo, C. W. (2005). *Dev Biol* 284, 479-98). However, the observation that Cx43 protein levels were similar in control and treated wounds by day 7 after injury suggests that angiogenesis in Cx43 asODN-treated wounds at this stage was most likely to have been indirectly influenced by the antisense-mediated changes that we saw at early stages. It is possible that angiogenesis is promoted by the early elevation in TGF-β1, as this growth factor has been reported to promote angiogenesis (Roberts, A. B., Sporn, M. B., Assoian, R. K., Smith, J. M., Roche, N. S., Wakefield, L. M., Heine, U. I., Liotta, L. A., Falanga, V., Kehrl, J. H. et al. (1986). *Proc Natl Acad Sci USA* 83, 4167-71), but the time frames for this do not match.

Granulation Tissue Maturation, Contraction and Cell Death

The area of granulation tissue following Cx43 asODN treatment is consistently smaller than that of control wounds. This is likely to be due to several factors. The reduced inflammatory response has several knock-on effects on subsequent stages of the healing process. Reduced neutrophil invasion will result in reduced damage in surrounding tissue, and most excisional wounds expand in size over the first few days of healing as the inflammatory process kicks in whereas treated wounds contract dramatically in the same period. Therefore, reduced inflammation would be expected to result in a significantly smaller area for the fibroblasts to fill. Because one of the other key effects that we have seen is and enhancement of fibroblast proliferation and migration the smaller wound can be filled much faster and the granulation tissue can begin to mature significantly faster.

In summary, these studies report our first data led analysis of the mechanism underlying the cell biology downstream of Cx43 protein reduction at wound sites. The local downregulation strongly influences very early events in wound healing. In particular, it limits the extent of the inflammatory response and advances the onset and rate of re-epithelialization and the level and rate of granulation tissue formation. The granulation tissue then has a smaller area to fill and does this faster, leading to earlier wound contraction and maturation. This approach clearly offers the potential for new therapies for improving wound healing in a variety of clinical situations.

Based on these results, experimental downregulation of connexin 43 expression at skin wound sites markedly improve the rate and quality of healing. The physiological and cell biological aspects of the repair process are compared in treatment with and without an exemplary anti-connexin agent—connexin 43 antisense oligodeoxynucleotide. Treated wounds exhibited accelerated skin healing with significantly increased keratinocyte and fibroblast proliferation and migration. In vitro knockdown of connexin 43 in a fibroblast wound-healing model also resulted in significantly faster healing, associated with increased mRNA for transforming growth factor beta 1, and collagen alpha1 and general collagen content at the wound site. Treated wounds showed enhanced granulation tissue formation and maturation with more rapid angiogenesis, myofibroblast differentiation and wound contraction was apparently advanced by 2-3 days. Recruitment of both neutrophils and macrophages was markedly reduced within treated wounds, concomitant with reduced leukocyte infiltration. In turn mRNA levels of chemokine ligand 2 and tumor necrosis factor alpha were reduced in the treated wound. These data indicate that under these conditions, reducing connexin 43 protein with connexin 43-specific antisense at wound sites early in the skin healing process enhances repair, at least in part, by accelerating cell migration and proliferation and by attenuating inflammation and the additional damage it can cause.

Acute downregulation of Cx43 protein at the wound site led to an increase in keratinocyte proliferation and migration, and in the rate at which fibroblasts migrate into the wound and lay down collagen matrix. This correlated with a decrease in neutrophil infiltration and a concomitant reduction in chemokine ligand 2 (Ccl2) and cytokine tumor necrosis factor alpha (TNF-α) mRNA. Subsequently, a reduced recruitment of macrophages was seen, perhaps as a consequence of damping down of the initial inflammatory response. In contrast, increased expression of TGF-β1 with increased hydroxyproline and collagen type 1α1 was observed in Cx43AsODN treated wounds. Together these modified responses resulted in significantly improved wound healing.

Example 2

Wound Healing in a Human Corneal Limbal Rim Model

Cell denuded pig stroma chimeras were cultured for two weeks and then assessed using a growth factor/cytokine antibody array (measures protein levels of 120 different growth factors/cytokines.

Figure 14:
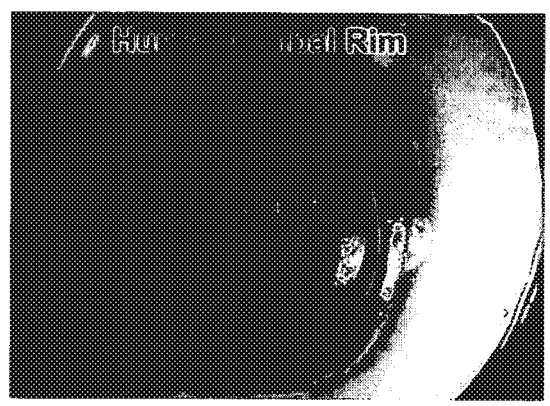
FIG. 14 depicts a Human Limbal rim—denuded pig stromal matrix chimera.

Human limbal rims returned from surgery after excision of the central corneas for keratoplasty (transplant) were placed into air liquid interface organotypic culture and a denuded pig stromal extracellular matrix inserted into the central region (FIG. 14). The pig stromal matrix was denuded (cells removed) by freeze-thawing in liquid nitrogen.

The chimeras were grown for up to 2 weeks at which time the human limbal epithelial cells have re-epithelialised the pig stroma with a normal 5-7 cell layer fully differentiated epithelium. In addition, human limbal stromal keratocytes have proliferated and migrated across the limbal rim—stromal insert to repopulate the pig stromal matrix with human keratocytes.

In a further experiment the chimeras were treated with connexin 43 specific antisense ODNs at day one. This resulted in a significant increase in the rate of re-epithelialisation with full epithelial covering of the pig stroma within 3 days compared with 7 to 14 days for the controls.

Figure 15:
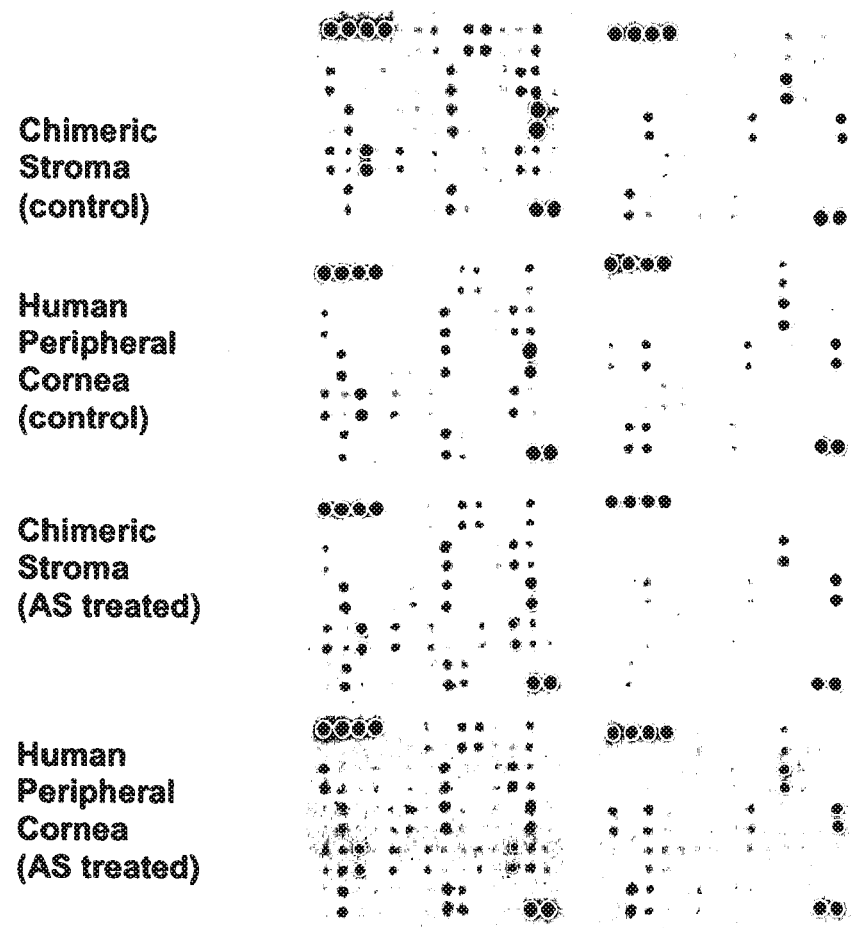
FIG. 15 depicts examples of growth factor and cytokines binding to the antibody arrays used to detect protein levels for 120 different growth factors and cytokines. Four samples were run on each of the two array membranes (60 growth factors/cytokines per membrane with repeats and both positive and negative controls).

After two weeks in culture the chimeras were cut in half: one half for histological analysis, and the other for growth factor and cytokine array analysis. For growth factor and cytokine analysis the central stromal region (with fully recovered human cell epithelium) and partially repopulated stroma (human keratocytes) was removed and homogenised separately from the human limbal rim which contains stem cell populations. The homogenates were run on a growth factor/cytokine array (FIG. 15) and analysis of growth factor levels performed using densitometry analysis of the array membranes. Analysis of key growth factors revealed a number of interest (FIG. 16 and FIG. 17).

Figure 16:
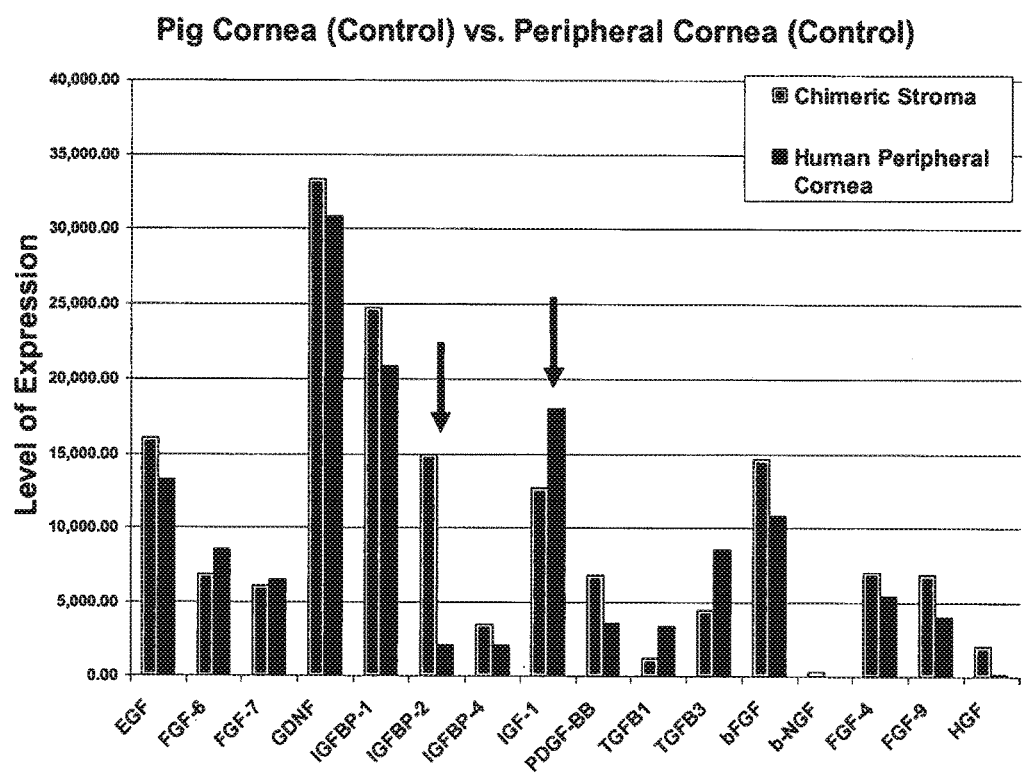
FIG. 16 depicts analysis of growth factor levels in chimeric stroma compared with limbal rim regions of the chimera after two weeks in culture. This is a control cornea (not antisense treated). Two growth factors are of particular interest (arrows). These are the very high levels of IGFBP-2 in the chimeric stroma and higher levels of IGF-1 in the limbal rim. The former has been reported to be important in promoting cellular migration (which may be important for the stromal keratocytes to repopulate the stoma from the limbal rim) and the latter has been reported to be important in promoting cell proliferation (which may be important in the limbal rim to provide the source of cells repopulating the stroma).

Analysis of growth factor levels in chimeric stroma compared with limbal rims regions of the chimera after two weeks in culture (control corneas—not antisense treated) revealed two growth factors of particular interest (FIG. 16). These were very high levels of IGFBP-2 in the chimeric stroma and higher levels of IGF-1 in the limbal rim. The former is said to promote cellular migration (needed for the stromal keratocytes to repopulate the stoma from the limbal rim) and the latter is said to promote cell proliferation (necessary in the limbal rim to provide the source of cells repopulating the stroma).

Figure 17:
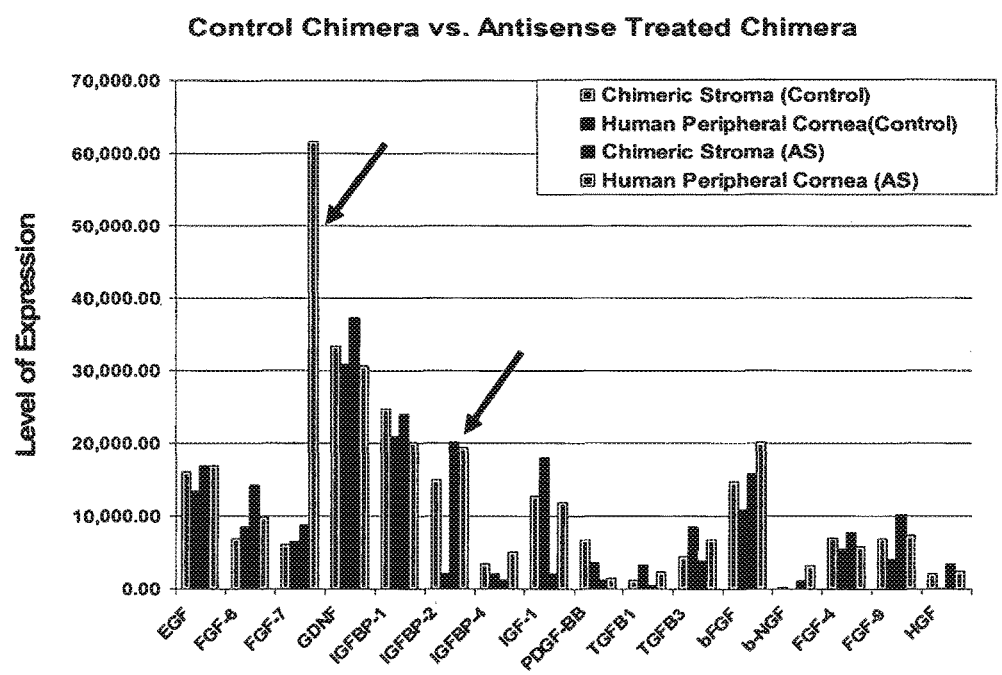
FIG. 17 depicts analysis of growth factor levels in chimeric stroma compared with limbal rim regions of the chimera after two weeks in culture (based on data from a Cx43As ODN treated cornea). Two growth factors are of particular interest (arrows). These are the high levels of IGF-7 in the antisense treated chimeric stroma compared with the untreated controls and higher levels of IGFBP-2 in both the limbal rim and stroma compared with untreated controls, especially control limbal rims. The former has been reported to be important in promoting epithelial growth (consistent with the increased re-epithelialistaion seen in antisense treated chimeras) and the latter has been reported to be important in promoting cell migration (consistent with the increased epithelial repopulation from the limbal rim with antisense treatment).

Analysis of growth factor levels in chimeric stroma compared with limbal rims regions of the Cx43As ODN treated chimeras after two weeks in culture revealed two growth factors of particular interest (FIG. 17). These were very high levels of IGF-7 in the antisense treated chimeric stroma compared with the untreated controls, and higher levels of IGFBP-2 in both the limbal rim and stroma compared with untreated controls, especially control limbal rims. The former is said to promote epithelial growth (consistent with the increased re-epithelialisation seen in antisense treated chimeras) and the latter is said to promote cell migration (consistent with the increased epithelial repopulation from the limbal rim with antisense treatment).

Example 3

Second degree burns are treated with a spray formulation including anti-connexin agent, 10 ug/ml of KGF, 30 ng/ml of a PDGF isoform, 10 ng/ml IGF-1, and 30 ng/ml of IGFBP-1. The spray is allowed to dry in the air. Re-application is suggested every couple of hours.

Example 4

A suture wound is closed and a topical salve made up of anti-connexin agent, 10% KGF and/or 5% PDGF is applied on the suture before bandaging. Re-application of the salve may be as needed in order to facilitate or improve wound healing, for example, up to 2-3 times daily for about 4-7 days, or as appropriate.

Example 5

A 20% zinc oxide formulation containing an anti-connexin agent and one or more of 5% KGF, 2.5% PDGF, 10% IGFBP is applied to minor abrasions, sunburns and chafing for faster healing of these wounds.

Example 6

A formulation containing an anti-connexin agent and one or more active antibiotic ingredients, for example, one or more of bacitracin, neomycin, and polymyxin is prepared. In one such formulation, each gram contains Polymyxin B Sulfate (5,000 units), Bacitracin Zinc (400 units), and/or Neomycin (3.5 mg). Inactive ingredients of the formulation may include cocoa butter, cottonseed oil, olive oil, sodium pyruvate, tocopheryl acetate, and white petrolatum, in desired amounts. Preferably, the anti-connexin agent is an anti-connexin 43 agent. Such formulations are applied, for example, to minor cuts, abrasions, sunburns and chafing for faster/improved healing of these wounds.

Example 7

A formulation containing an anti-connexin agent as provided in Example 6 is prepared to also contain a topical analgesic (e.g., pramoxine).

Example 8

A formulation containing an anti-connexin agent as provided in Example 6 or Example 7 is prepared to contain gramicidin.

Example 9

A formulation containing an anti-connexin agent and one or more active antifungal ingredients, for example, miconazole nitrate one is prepared. One such formulation contains 2% miconazole nitrate. Inactive ingredients may include propylene glycol 300, polysorbate 20 (and), SD alcohol 40B. The product may formulated as a cream, gel, spray or liquid. Suitable propellants for spray formulations include dimethyl ether. Preferably, the anti-connexin agent is an anti-connexin 43 agent. Such formulations are applied, for example, to treat athlete's foot, jock itch, and ringworm.

Example 10

This example demonstrates a method for identifying potential cytokines useful in the treatment of wounds using a corneal model. The cornea contains dendritic cells known as Langerhans cells, which are activated in response to injury. Additional inflammatory cells are then recruited from the blood vessels at the limbus. Our model corneas are cultured in isolation from a blood supply, therefore, recruitment of macrophages, T-cells and polymorphonuclear cells is impossible.

The model coreneas were used to determine if the presence of Langerhans cells would be sufficient to illicit an inflammatory response and whether that response could be distinguished from the healing response. Two matched human corneas were wounded using different techniques. One cornea was ablated to a depth of 80 μm over a 7 mm diameter using an excimer laser phototherapeutic keratectomy ablation, a technique which stimulates very low levels of inflammation. The other cornea was wounded using a 7 mm circle of filter paper soaked in sodium NaOH for 1 minute, a technique known to induce inflammation. After culturing for 24 hours, the corneas were divided in half (one for immunohistochemistry and one for cytokine analysis. The cornea was further divided into portions within the healing zone and outside the healing zone before processing for cytokine array analysis.

Figure 18:
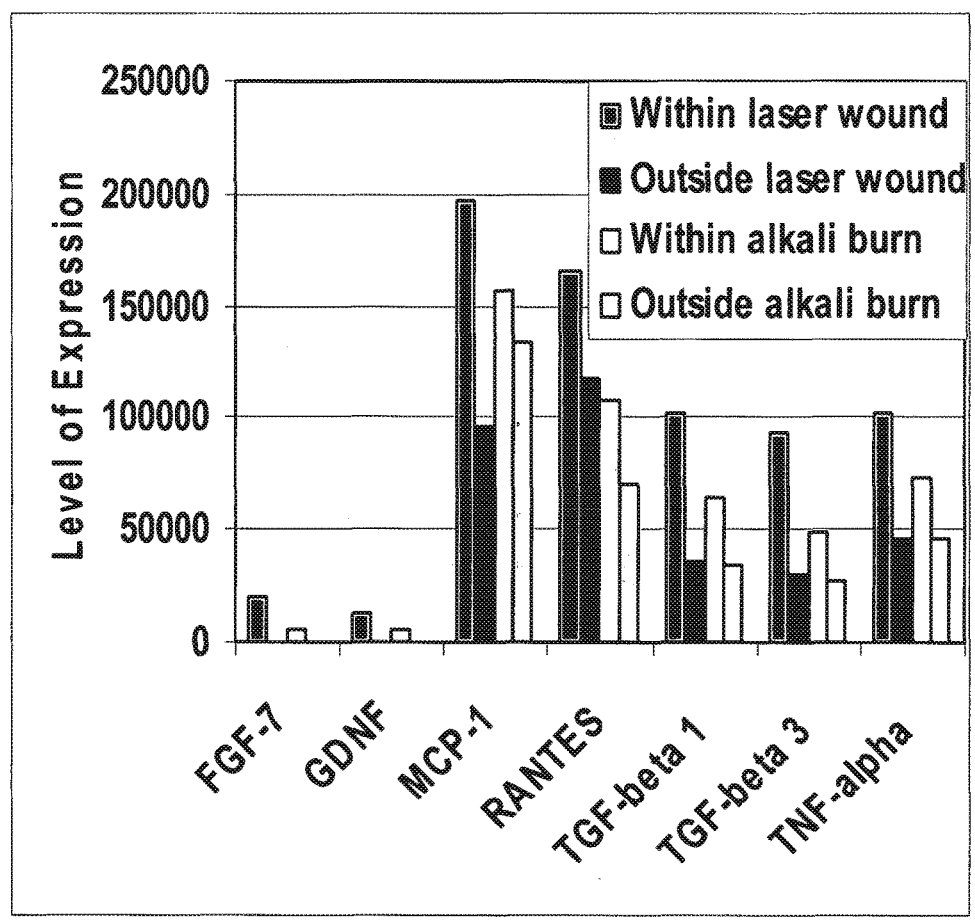
FIG. 18 illustrates a group of representative cytokines which were identified based on their increased levels of expression in an inflammatory compared to low inflammatory wound models. These representative cytokines can serve as suitable targets for modulation of wound healing.
Figure 19:
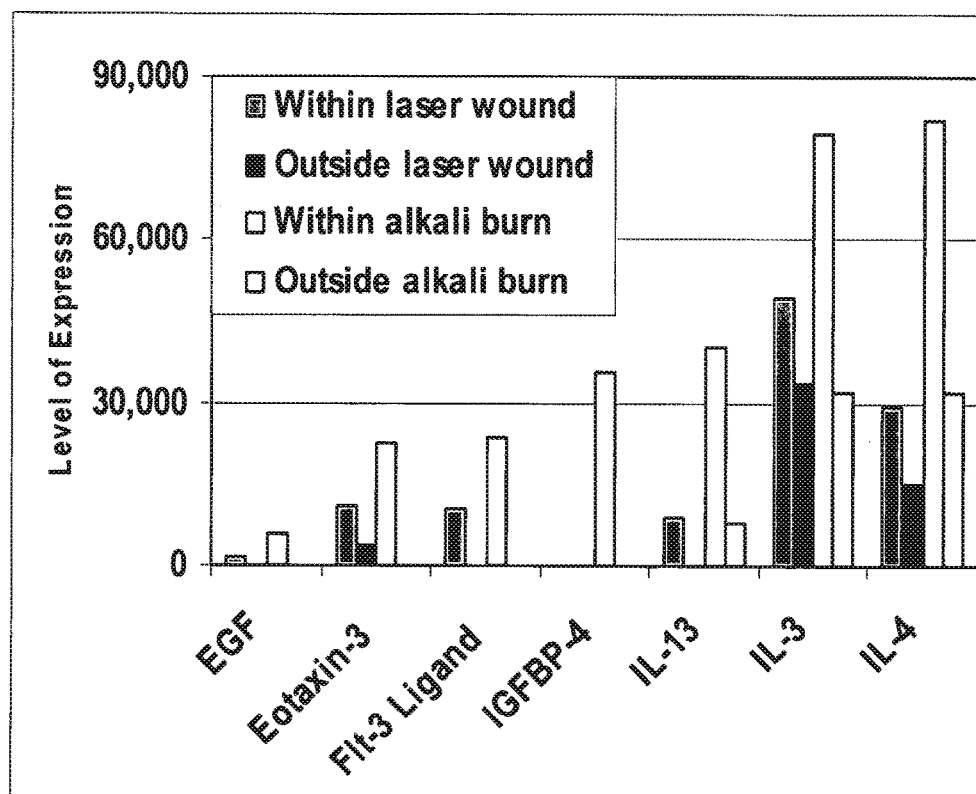
FIG. 19 illustrates a group of representative cytokines which were identified based on their increased levels of expression in low inflammatory wound model compared to the inflammatory model. These representative cytokines can serve as suitable targets for modulation of wound healing.

An inflammatory response was identified in both corneas but it was enhanced within the alkali burn. Cytokine profiles between the two groups due to the greater inflammation within the alkali burn sample and because healing commenced faster in the lasered cornea as less removal of necrotic tissue is required. FIG. 18 shows a group of cytokines increased in both wounds but far more so in the inflammatory wound model. This group included interleukins. FIG. 19 shows a set of cytokines which were increased in both models but more so in the low inflammation model and thus represent cytokines to target for improved healing.

Efficacy of various cytokines in the wound healing model is determined by assessing the effect of the cytokines augmentation in a wound healing model. In addition, the abilities of various cytokines of interest to increase the rate of wound healing and to improve quality of healing are assessed.

Example 11

This example demonstrates a method for dertermining cytokines for therapeutic use. Cytokines may be selected for use herein based on their altered levels as induced by Cx43AsODN treatment. These cytokines can have an effect on corneal wound healing, for example, when they are administered exogenously in a keratoplasty model of wound healing.

Model: Paired human limbal rims with inserted pig stromal implants are tested in cultured keratoplasty model for alterations in the cytokine levels. The tissue level of the added cytokine is gauged by array data. For temporal study, cytokines are added at the onset of the healing process. Optimal treatment periods are determined with additional data points if needed. In the case wherein the healing follows the same time course as the Cx43AsODNs model, then the culture times are assessed for 3 and 7 days. Healing time course is determined using dark field microscopy and adjusted as necessary.

Technique: 5 pairs of limbal rims per cytokine are used in escalating doses to establish a dose response curve.

The same methods for investigation of corneal wound healing are employed as stated above in Example 9, except that the epithelial plug that forms in unsutured corneal wound healing are used to isolate epithelial wound healing from stromal wound healing. Factors that influence epithelial recovery are assessed independently of the influence of stromal cells. In some instances it might be preferable to increase corneal epithelial wound healing to preserve the barrier protection, but not to increase stromal wound healing which might induce haze.

Cytokines of interest in corneal wound healing are identified. Candidates include, for example, IGF and IGFBP2 from normal tissue studies and FGF-7 from antisense studies.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

We claim:

1. A method for promoting or improving healing of optic nerve or eye tissue in a subject, comprising administering to the subject an anti-connexin agent simultaneously with, separately from or sequentially with a medicament comprising a therapeutically effective amount of an antagonist of VEGF, wherein the connexin agent is an anti-connexin 43 polynucleotide or an anti-connexin 43 peptide or peptidomimetic.

2. A method according to claim 1, wherein the anti-connexin agent and the VEGF antagonist are administered simultaneously.

3. A method according to claim 1, wherein the anti-connexin agent and the VEGF antagonist are not administered simultaneously.

4. A method according to claim 1, wherein the anti-connexin agent and the VEGF antagonist are administered sequentially.

5. A method according to claim 1, wherein the anti-connexin agent is administered first.

6. A method according to claim 1, wherein the VEGF antagonist is administered first.

7. The method according to any one of claim 1, or 2-5, wherein the anti-connexin agent is formulated in a matrix.

8. A method for promoting or improving healing of eye tissue in a subject, comprising administering to the subject an anti-connexin 43 peptide or peptidomimetic simultaneously with, separately from or sequentially with a medicament comprising a therapeutically effective amount of an antagonist of VEGF.

9. A method according to claim 8, wherein the antagonist of VEGF is an antagonist of VEGF-A.

10. A method according to claim 8, wherein the anti-connexin 43 peptide or peptidomimetic is from 8 to about 15 amino acids and comprises SRPTEKT (SEQ ID NO:35).

11. A method according to claim 8, wherein the anti-connexin 43 peptide or peptidomimetic is from 11 to about 13 amino acids and comprises SRPTEKT (SEQ ID NO:35).

12. A method according to claim 10, wherein the anti-connexin 43 peptide or peptidomimetic is VDCFLSRPTEKT (SEQ.ID.NO: 18).

13. A method according to claim 10, wherein the anti-connexin 43 peptide or peptidomimetic is SRPTEKTIFII (SEQ.ID.NO: 19).

14. A method according to claim 11, wherein the anti-connexin 43 peptide or peptidomimetic is VDCFLSRPTEKT (SEQ.ID.NO:18).

15. A method according to claim 11, wherein the anti-connexin 43 peptide or peptidomimetic is SRPTEKTIFII (SEQ.ID.NO:19).

16. The method according to any one of claim 1, or 2-5, wherein the anti-connexin agent is formulated in a delayed release preparation, a slow release preparation, an extended release preparation, a controlled release preparation.

17. The method according to any one of claims 8-13, 14, or, 15 wherein the anti-connexin agent is formulated in a matrix.

18. The method according to any one of claims 8-13, 14, or, 15 wherein the anti-connexin agent is formulated in a delayed release preparation, a slow release preparation, an extended release preparation, a controlled release preparation.

* * * * *